(12) United States Patent
Keren et al.

(10) Patent No.: US 8,790,267 B2
(45) Date of Patent: Jul. 29, 2014

(54) DYNAMICALLY VARIABLE FILTER

(75) Inventors: Hanan Keren, Kfar-Saba (IL); Yoav Avidor, Tel-Aviv (IL); Pierre Squara, Enghien-les-Bains (FR); Daniel Burkhoff, West Harrison, NY (US); Baruch Levy, Tel Aviv (IL)

(73) Assignee: Cheetah Medical, Inc., Wilmington, DE (US)

( * ) Notice: Subject to any disclaimer, the term of this patent is extended or adjusted under 35 U.S.C. 154(b) by 639 days.

(21) Appl. No.: 12/673,037

(22) PCT Filed: Aug. 11, 2008

(86) PCT No.: PCT/IL2008/001105
§ 371 (c)(1),
(2), (4) Date: Feb. 11, 2010

(87) PCT Pub. No.: WO2009/022330
PCT Pub. Date: Feb. 19, 2009

(65) Prior Publication Data
US 2011/0218419 A1      Sep. 8, 2011

Related U.S. Application Data

(63) Continuation of application No. 11/889,395, filed on Aug. 13, 2007.

(51) Int. Cl.
*A61B 5/02*         (2006.01)
*A61B 5/026*        (2006.01)
*A61B 5/029*        (2006.01)

(52) U.S. Cl.
USPC .......................................... 600/528; 600/508

(58) Field of Classification Search
USPC ................................................ 600/508, 526
See application file for complete search history.

(56) References Cited

U.S. PATENT DOCUMENTS

| | | |
|---|---|---|
| 3,340,867 A | 9/1967 | Kubicek et al. |
| 3,851,641 A | 12/1974 | Toole et al. |
| 3,874,368 A | 4/1975 | Asrican |
| 3,914,999 A | 10/1975 | Grandchamp |
| 4,094,309 A | 6/1978 | Grzenia |
| 4,153,048 A | 5/1979 | Magrini |
| RE30,101 E | 9/1979 | Kubicek et al. |
| 4,437,469 A | 3/1984 | Djordjevich et al. |
| 4,450,527 A | 5/1984 | Sramek |
| 4,537,200 A | 8/1985 | Widrow |
| 4,610,254 A | 9/1986 | Morgan et al. |

(Continued)

FOREIGN PATENT DOCUMENTS

| | | |
|---|---|---|
| WO | WO 82/00581 | 3/1982 |
| WO | WO 96/32883 | 10/1996 |

(Continued)

OTHER PUBLICATIONS

Communication Pursuant to Article 94(3) EPC Dated Jan. 26, 2011 From the European Patent Office Re.: Application No. 04731993.4.

(Continued)

*Primary Examiner* — Tammie K Heller

(57) ABSTRACT

A method of processing a signal pertaining to at least one electrical property of an organ of a subject is disclosed. The method comprises determining a physiological condition of the subject, selecting a frequency band, filtering the signal according to the frequency band, and dynamically adapting the frequency band in response to a change in the physiological condition.

27 Claims, 63 Drawing Sheets

(56) References Cited

U.S. PATENT DOCUMENTS

| | | |
|---|---|---|
| 4,705,049 A | 11/1987 | John |
| 4,781,201 A | 11/1988 | Wright et al. |
| 4,803,431 A | 2/1989 | Sano et al. |
| 4,805,621 A | 2/1989 | Heinze et al. |
| 4,852,580 A | 8/1989 | Wood |
| 4,870,578 A | 9/1989 | Vysin et al. |
| 4,888,558 A | 12/1989 | Hereikson |
| 4,926,868 A | 5/1990 | Larsen |
| 4,953,556 A | 9/1990 | Evans |
| 5,058,583 A | 10/1991 | Geddes et al. |
| 5,158,093 A | 10/1992 | Shvartz et al. |
| 5,178,154 A | 1/1993 | Ackmann et al. |
| 5,309,917 A | 5/1994 | Wang et al. |
| 5,316,004 A | 5/1994 | Chesney et al. |
| 5,423,326 A | 6/1995 | Wang et al. |
| 5,469,859 A | 11/1995 | Tsoglin et al. |
| 5,503,157 A | 4/1996 | Sramek |
| 5,505,209 A | 4/1996 | Reining |
| 5,529,072 A | 6/1996 | Sramek |
| 5,615,689 A | 4/1997 | Kotler |
| 5,642,734 A | 7/1997 | Ruben et al. |
| 5,685,316 A | 11/1997 | Schookin et al. |
| 5,817,030 A | 10/1998 | Tarjan et al. |
| 5,913,826 A | 6/1999 | Blank |
| 6,015,393 A | 1/2000 | Hovland et al. |
| 6,053,873 A | 4/2000 | Govari et al. |
| 6,073,039 A | 6/2000 | Berson |
| 6,076,015 A | 6/2000 | Hartley et al. |
| 6,142,941 A | 11/2000 | Benhalima et al. |
| 6,298,267 B1 | 10/2001 | Rosborough et al. |
| 6,304,773 B1 | 10/2001 | Taylor et al. |
| 6,339,722 B1 | 1/2002 | Heethaar et al. |
| 6,413,223 B1 | 7/2002 | Yang et al. |
| 6,440,082 B1 | 8/2002 | Joo et al. |
| 6,485,431 B1 | 11/2002 | Campbell |
| 6,496,732 B1 | 12/2002 | Wallace |
| 6,511,438 B2 | 1/2003 | Bernstein et al. |
| 6,577,897 B1 | 6/2003 | Shurubura et al. |
| D625,823 S | 10/2010 | Schneider et al. |
| 8,414,498 B2 | 4/2013 | Keren et al. |
| 2002/0143368 A1 | 10/2002 | Bakels et al. |
| 2002/0193689 A1 | 12/2002 | Bernstein et al. |
| 2003/0083702 A1 | 5/2003 | Stadler et al. |
| 2003/0109790 A1 | 6/2003 | Stickney et al. |
| 2003/0120170 A1 | 6/2003 | Zhu et al. |
| 2003/0158584 A1 | 8/2003 | Cates et al. |
| 2003/0187341 A1 | 10/2003 | Sackner et al. |
| 2003/0199779 A1 | 10/2003 | Muhlenberg et al. |
| 2004/0102908 A1 | 5/2004 | Larson et al. |
| 2004/0133123 A1 | 7/2004 | Leonhardt et al. |
| 2005/0043763 A1 | 2/2005 | Marcovecchio et al. |
| 2005/0124901 A1 | 6/2005 | Misczynski et al. |
| 2005/0143634 A1 | 6/2005 | Baker, Jr. et al. |
| 2005/0192488 A1 | 9/2005 | Bryenton et al. |
| 2005/0202789 A1 | 9/2005 | Tanabe et al. |
| 2005/0217674 A1 | 10/2005 | Burton et al. |
| 2006/0085048 A1 | 4/2006 | Cory et al. |
| 2006/0122540 A1 | 6/2006 | Zhu et al. |
| 2006/0200033 A1 | 9/2006 | Keren et al. |
| 2007/0088221 A1 | 4/2007 | Stahmann |
| 2007/0191688 A1 | 8/2007 | Lynn |
| 2008/0154116 A1 | 6/2008 | Duensing et al. |
| 2008/0255433 A1 | 10/2008 | Prough et al. |
| 2009/0048497 A1 | 2/2009 | Keren |
| 2010/0069765 A1 | 3/2010 | Keren |
| 2013/0144177 A1 | 6/2013 | Keren et al. |

FOREIGN PATENT DOCUMENTS

| | | |
|---|---|---|
| WO | WO 97/11638 | 4/1997 |
| WO | WO 2004/098376 | 11/2004 |
| WO | WO 2004/112606 | 12/2004 |
| WO | WO 2006/087696 | 8/2006 |
| WO | WO 2007/096054 | 8/2007 |
| WO | WO 2008/102362 | 8/2008 |
| WO | WO 2008/107899 | 9/2008 |
| WO | WO 2008/129535 | 10/2008 |
| WO | WO 2009/022330 | 2/2009 |

OTHER PUBLICATIONS

Response Dated Jan. 30, 2011 to Communication Pursuant to Article 94(3) EPC of Oct. 20, 2010 From the European Patent Office Re. Application No. 08719934.5.
Communication Pursuant to Article 94(3) EPC Dated Feb. 13, 2012 From the European Patent Office Re. Application No. 08789780.7.
Requisition by the Examiner Dated Jan. 9, 2012 From the Canadian Intellectual Property Office Re. Application No. 2,525,443.
Communication Pursuant to Article 94(3) EPC Dated Feb. 13, 2012 From the European Patent Office Re. : Application No. 08710233.1.
Communication Pursuant to Article 94(3) EPC Dated Feb. 13, 2012 From the European Patent Office Re. Application No. 08719934.5.
Communication Pursuant to Article 94(3) EPC Dated Jul. 8, 2009 From the European Patent Office Re.: Application No. 04731993.4.
Communication Pursuant to Article 94(3) EPC Dated Feb. 12, 2010 From the European Patent Office Re.: Application No. 08738211.5.
Communication Pursuant to Article 94(3) EPC Dated Dec. 29, 2009 From the European Patent Office Re.: Application No. 08710233.1.
Communication Relating to the Results of the Partial International Search Dated Dec. 5, 2008 From the International Searching Authority Re.: Application No. PCT/IL2008/001105.
International Preliminary Report on Patentability Dated Aug. 16, 2007 From the International Preliminary Examining Authority Re.: Application No. PCT/IL06/00075.
International Preliminary Report on Patentability Dated Sep. 17, 2009 From the International Bureau of WIPO Re.: Application No. PCT/IL2008/000309.
International Preliminary Report on Patentability Dated Nov. 18, 2008 From the International Preliminary Examing Authority Re.: Application No. PCT/IL04/00395.
International Preliminary Report on Patentability Dated Aug. 26, 2009 From the International Bureau of WIPO Re.: Application No. PCT/IL2008/000233.
International Preliminary Report on Patentability Dated Oct. 29, 2009 From the International Bureau of WIPO Re.: Application No. PCT/IL2008/000509.
International Search Report Dated Aug. 5, 2008 From the International Searching Authority Re.: Application No. PCT/IL2008/000309.
International Search Report Dated Dec. 6, 2006 From the International Searching Authority Re.: Application No. PCT/IL06/00075.
International Search Report Dated Mar. 22, 2005 From the International Searching Authority Re.: Application No. PCT/IL04/00395.
International Search Report Dated Mar. 27, 2009 From the International Searching Authority Re.: Application No. PCT/IL2008/001105.
International Search Report Dated Jul. 28, 2008 From the International Searching Authority Re.: Application No. PCT/IL2008/000233.
Office Action Dated Dec. 12, 2008 From the State Intellectual Property Office of the People's Republic of China Re.: Application No. 200680012560.2.
Office Action Dated Apr. 24, 2009 From the State-Intellectual Property Office of the People's Republic of China Re.: Application No. 200480019436.X.
Office Action Dated Jul. 24, 2009 From the State Intellectual Property Office of the People's Republic of China Re.: Application No. 200680012560.2 and Its Translation Into English.
Official Action Dated Oct. 6, 2009 From the US Patent and Trademark Office Re.: U.S. Appl. No. 10/556,483.
Official Action Dated Feb. 18, 2009 From the US Patent and Trademark Office Re.: U.S. Appl. No. 10/556,483.
Response Dated Apr. 6, 2010 to Official Action of Oct. 6, 2009 From the US Patent and Trademark Office Re.: U.S. Appl. No. 10/556,483.
Response Dated Nov. 8, 2009 to Communication Pursuant to Article 94(3) EPC of Jul. 8, 2009 From the European Patent Office Re.: Application No. 04731993.4.

(56) References Cited

OTHER PUBLICATIONS

Supplementary Partial European Search Report Dated Apr. 9, 2009 From the European Patent Office Re.: Application No. 04731993.4.
Translation of the Official Action Dated Dec. 12, 2008 From the State Intellectual Property Office of the People's Republic of China Re.: Application No. 200680012560.2.
Written Opinion Dated Aug. 5, 2008 From the International Searching Authority Re.: Application No. PCT/IL2008/000309.
Written Opinion Dated Dec. 6, 2006 From the International Searching Authority Re.: Application No. PCT/IL06/00075.
Written Opinion Dated Mar. 22, 2005 From the International Searching Authority Re.: Application No. PCT/Il04/00395.
Written Opinion Dated Mar. 27, 2009 From the International Searching Authority Re.: Application No. PCT/IL2008/001105.
Written Opinion Dated Jul. 28, 2008 From the International Searching Authority Re.: Application No. PCT/IL2008/000233.
Bakshi et al. "Circulatory Response in Sleep Apnea Patients During Sleep Before and After CPAP Treatment", Sleep, XO008094214, 28(Suppl.S): A194: 0576, 2005. 19th Annual Meeting of the Associated-Professional-Sleep-Societies, Denver, CO, USA, Jun. 18-23, 2005. Abstract.
Goovaerts et al. "A Wideband High Common Mode Rejection Ratio Amplifier for Multifrequency Impedance Measurement", Medical and Biological Engineering and Computing, XP000784850, 36(6): 761-767, Nov. 1, 1998. Section 2.2 'Lock-in Measurement', p. 761, p. 763, col. 2, Figs.2, 3.
Jellinek et al. "Right Atrial Pressure Predicts Hemodynamic Response to Apneic Positive Airway Pressure", Critical Care Medicine, XP002488470, 28(3): 672-678, Mar. 2000. Database MEDLINE[Online], US National Library of Medicine, Database Accession No. NLM10752813. Abstract.
Kubicek et al. "The Minnesota Impedance Cardiograph—Theory and Applications", Biomedical Engineering, XP001051054, 9(9): 410-416, Sep. 1, 1974. p. 411, Middle Col., Figs.1, 2.
Lele et al. "Exercise Capacity in Hypertrophic Cardiomyopathy: Role of Stroke Volume Limitation, Heart Rate, and Diastolic Filling Characteristics", Circulation, XP002487808, 92(10): 2886-2894, 1995.
Lin et al. "Effects of Hypercapnia, Hypoxia, and Rebreathing on Circulatory Response to Apnea", Journal of Applied Physiology Respiratory Environmental and Exercise Physiology, XP008094195, 54(1): 172-177, 1983.
Miyamoto et al. "Cardiorespiratory Dynamics During Sinusoidal and Impulse Exercise in Man", Japanese Journal of Physiology, XP008094022, 33(6): 971-986, 1983.
Myers et al. "Cardiac Output and Cardiopulmonary Responses to Exercise in Heart Failure: Application of a New Bio-Resistance Device", Journal of Cardiac Failure, XP0022287174, 13(8): 629-636, Oct. 6, 2007.
Newman et al. "The Non-Invasive Assessment of Stroke Volume and Cardiac Output by Impedance Cardiography: A Review", Aviation Space and Environmental Medicine, XP008093991, 70(8): 780-789, Aug. 1999.
Raza et al. "Filtering Respiration and Low-Frequency Movement Artefacts From the Cardiogenic Electrical Impedance Signal", Medical and Biological Engineering and Computing, XP000323425, 30(5): 556-561, Sep. 1, 1992. p. 556, r-h Col., § 3-p. 557, r-h Col., § 1, p. 557, l-h Col., § 3, p. 558, l-h Col., § 2-r-h Col., § 1, Fig.3.
Saarelainen et al. "Whole-Body Impedance Recording—A Practical Method for the Diagnosis of Sleep Apnoea", Clinical Physiology and Functional Imaging, XO002488466, 23(2): 110-113, Mar. 2003.
Schumacker et al. "Oxygen Delivery and Uptake Relationships in Patients With Aortic Stenosis", American Journal of Respiratory and Critical Care Medicine, XP002488468, 149(5): 1123-1131, May 1994. Database EMBASE [Online], Database Accession No. EMB-1994152503, 1994. Abstract.
Stoohs et al. "Cardiovascular Changes Associated With Obstructive Sleep Apnea Syndrome", Journal of Applied Physiology, XP002488467, 72(2): 583-589, 1992. Database Biosis [Online], Biosciences Information Service, Database Accession No. PREV199293105800, 1992. Abstract.
Tolle et al. "Reduced Stroke Volume Related to Pleural Pressure in Obstructive Sleep Apnea", Journal of Applied Physiology Respiratory Environmental and Exercise Physiology, XP002488469, 55(6): 1718-1724, 1983. Database BIOSIS [Online], Biosciences Information Service, Database Accession No. PREV198477063246, 1883. Abstract.
Communication Pursuant to Article 94(3) EPC Dated May 14, 2012 From the European Patent Office Re. : Application No. 04731993.4.
Requisition by the Examiner Dated May 30, 2012 From the Canadian Intellectual Property Office Re. Application No. 2,597,264.
Response Dated Jun. 3, 2010 to Communication Pursuant to Article 94(3) EPC of Feb. 12, 2010 From the European Patent Office Re.: Application No. 08738211.5.
Restriction Official Action Dated Jun. 7, 2012 From the US Patent and Trademark Office Re. U.S. Appl. No. 11/889,395.
Invitation Pursuant to Rule 62a(1) EPC Dated Jun. 10, 2010 From the European Patent Office Re. Application No. 06700959.7.
Official Action Dated Jun. 22, 2010 From the US Patent and Trademark Office Re.: U.S. Appl. No. 10/556,483.
Response Dated Jun. 28, 2010 to Communication Pursuant to Article 94(3) EPC of Dec. 29, 2009 From the European Patent Office Re.: Application No. 08710233.1.
Response Dated Jul. 4, 2010 to Invitation Pursuant to Rule 62a(1) EPC of Jun. 10, 2010 From the European Patent Office Re. Application No. 06700959.7.
Official Action Dated Jul. 10, 2012 From the US Patent and Trademark Office Re. U.S. Appl. No. 12/527,697.
Translation of Official Querry Dated Jul. 1, 2011 From the Japanese Patent Office Re. Application No. 2006-507622.
Response Dated Jul. 21, 2010 to Notice of Reason for Rejection of Apr. 6, 2010 From the Japanese Patent Office Re. Application No. 2006-507622.
Translation of Notice of Reason for Rejection Dated Apr. 6, 2010 From the Japanese Patent Office Re. Application No. 2006-507622.
Response Dated Jul. 25, 2011 to Communication Pursuant to Article 94(3) EPC of Jan. 26, 2011 From the European Patent Office Re.: Application No. 04731993.4.
Official Action Dated Aug. 2, 2012 From the US Patent and Trademark Office Re. U.S. Appl. No. 11/884,227.
Official Action Dated Jul. 24, 2012 From the US Patent and Trademark Office Re. U.S. Appl. No. 12/596,483.
Patent Examination Report Dated Aug. 1, 2012 From the Australian Government, IP Australia Re. Application No. 2008242145.
Official Action Dated Aug. 9, 2012 From the US Patent and Trademark Office Re. U.S. Appl. No. 11/889,395.
Official Action Dated Aug. 31, 2011 From the US Patent and Trademark Office Re. U.S. Appl. No. 11/884,227.
Response Dated Sep. 11, 2011 to Official Querry Dated Jul. 1, 2011 From the Japanese Patent Office Re. Application No. 2006-507622.
Requisition by the Examiner Dated Jul. 24, 2012 From the Canadian Intellectual Property Office Re. Application No. 2,525,443.
Response Dated Sep. 12, 2011 to Official Action of Aug. 31, 2011 From the US Patent and Trademark Office Re. U.S. Appl. No. 11/884,227.
Communication Under Rule 71(3) EPC Dated Oct. 7, 2011 From the European Patent Office Re. : Application No. 08738211.5.
Response Dated Sep. 21, 2010 to Official Action of Jun. 22, 2010 From the US Patent and Trademark Office Re.: U.S. Appl. No. 10/556,483.
Translation of Notice of Reason for Rejection Dated Sep. 17, 2010 From the Japanese Patent Office Re. Application No. 2006-507622.
Communication Pursuant to Article 94(3) EPC Dated Oct. 20, 2010 From the European Patent Office Re. Application No. 08719934.5.
Official Action Dated Nov. 2, 2011 From the US Patent and Trademark Office Re. U.S. Appl. No. 11/884,227.
Delpierre et al. "Doppler Effect With Sound", Electronic Science Tutor, Retrieved From the Internet, 5 P., Oct. 18, 2011.
Ellis "Introduction to Mixers", Retrieved From the Internet, 9 P., 1999.
Written Opinion Dated Mar. 22, 2005 From the International Searching Authority Re.: Application No. PCT/Il04/00395.

(56) References Cited

OTHER PUBLICATIONS

Bakshi et al. "Circulatory Response in Sleep Apnea Patients During Sleep Before and After CPAP Treatment", Sleep, XO008094214, 28(Suppl.S): A194: 0576, 2005. 19th Annual Meeting of the Associated-Professional-Sleep-Societies, Denver, CO, USA, Jun. 18-23, 2005. Abstract.
Saarelainen et al. "Whole-Body Impedance Recording—A Practical Method for the Diagnosis of Sleep Apnoea", Clinical Physiology and Functional Imaging, XO002488466, 23(2): 110-113, Mar. 2003.
Examiner's Report Dated Nov. 15, 2010 From the Australian Government, IP Australia Re. Application No. 2006215274.
Response Dated Dec. 29, 2010 to Notice of Reason for Rejection of Sep. 17, 2010 From the Japanese Patent Office Re. Application No. 2006-507622.
Response Dated Nov. 17, 2011 to Examiner's Report of Nov. 15, 2010 From the Australian Government, IP Australia Re. Application No. 2006215274.
International Preliminary Report on Patentability Dated Nov. 4, 2009 From the International Preliminary Examining Authority Re.: Application No. PCT/IL2008/001105.
Notice of Allowance Dated Jan. 30, 2013 From the US Patent and Trademark Office Re.: U.S. Appl. No. 10/556,483.
Official Action Dated Apr. 9, 2013 From the US Patent and Trademark Office Re. U.S. Appl. No. 12/527,697.
Notice of Allowability Dated Nov. 21, 2012 From the US Patent and Trademark Office Re. U.S. Appl. No. 11/884,227.
Notice of Allowance Dated May 10, 2013 From the US Patent and Trademark Office Re. U.S. Appl. No. 12/596,483.
Official Action Dated Jun. 17, 2013 From the US Patent and Trademark Office Re. U.S. Appl. No. 12/450,022.
Applicant-Initiated Interview Summary Dated Sep. 17, 2012 From the US Patent and Trademark Office Re. U.S. Appl. No. 11/884,227.
Communication Under Rule 71(3) EPC Dated Oct. 17, 2012 From the European Patent Office Re. Application No. 08789780.7.
Notice of Allowance Dated Oct. 25, 2012 From the US Patent and Trademark Office Re. U.S. Appl. No. 11/884,227.
Official Action Dated Oct. 23, 2012 From the US Patent and Trademark Office Re. U.S. Appl. No. 12/450,022.
Patent Examination Report Dated Nov. 30, 2012 From the Australian Government, IP Australia Re. Application No. 2008288084.
Official Action Dated Apr. 30, 2013 From the US Patent and Trademark Office Re. U.S. Appl. No. 11/889,395.
Brief Communication for Oral Proceedings on Dec. 10, 2013 Dated Dec. 3, 2013 From the European Patent Office Re. Application No. 04731993.4.
Scofield "A Frequency-Domain Description of a Lock-in-Amplifier", American Journal of Physics, XP009097728, 62(2): 129-133, Feb. 1, 1994.
Requisition by the Examiner Dated Dec. 6, 2013 From the Canadian Intellectual Property Office Re. Application No. 2,597,264.
Official Action Dated Aug. 12, 2013 From the US Patent and Trademark Office Re. U.S. Appl. No. 13/757,920.
Summons to Attend Oral Proceedings Pursuant to Rule 115(1) EPC Dated Sep. 5, 2013 From the European Patent Office Re. Application No. 04731993.4.
Official Action Dated Jun. 26, 2013 From the US Patent and Trademark Office Re. U.S. Appl. No. 12/527,697.
Restriction Official Action Dated Jul. 3, 2013 From the US Patent and Trademark Office Re. U.S. Appl. No. 13/757,920.
Official Action Dated Mar. 10, 2014 From the US Patent and Trademark Office Re. U.S. Appl. No. 11/889,395.
Official Action Dated May 2, 2014 From the US Patent and Trademark Office Re. U.S. Appl. No. 13/757,920.

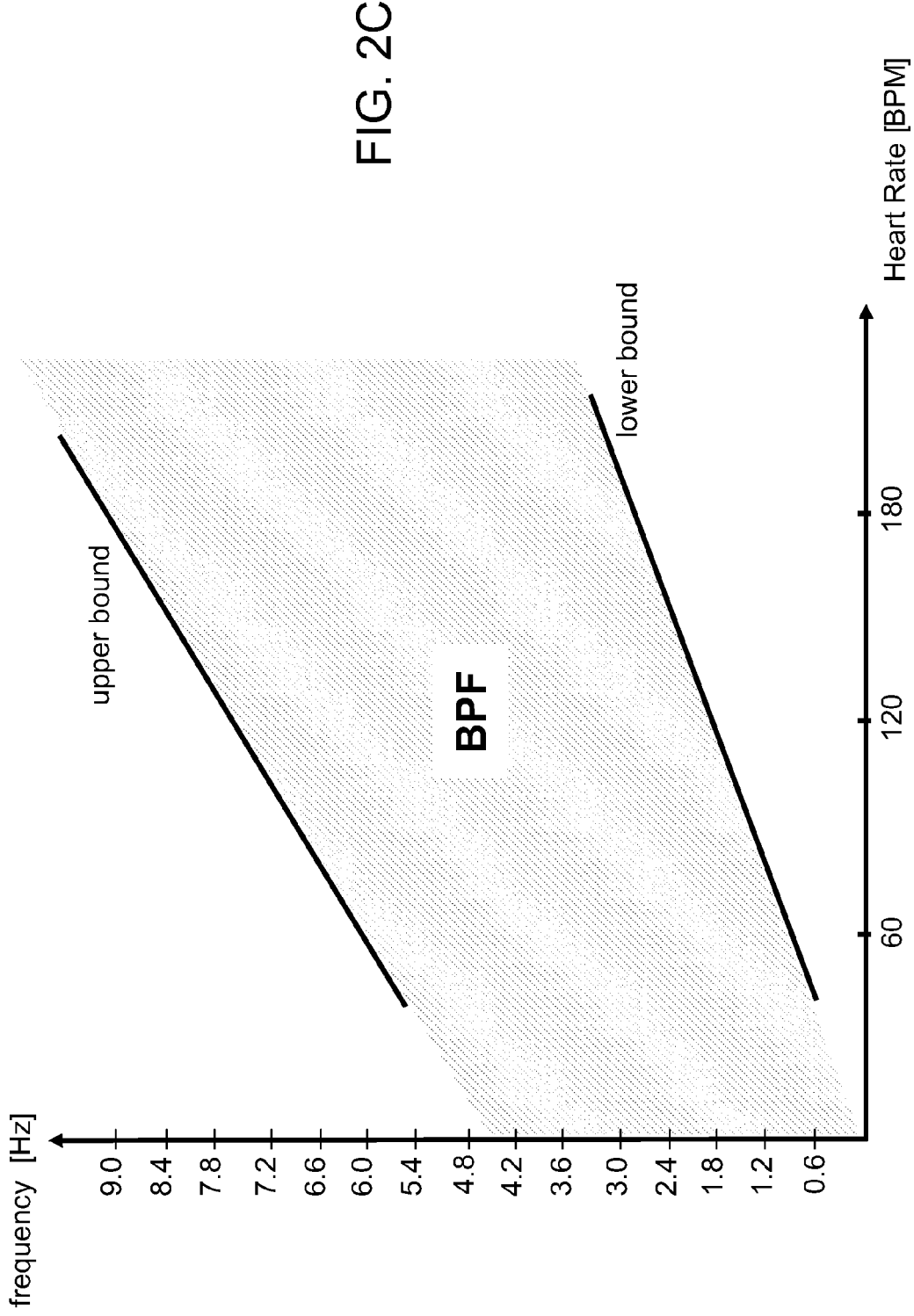

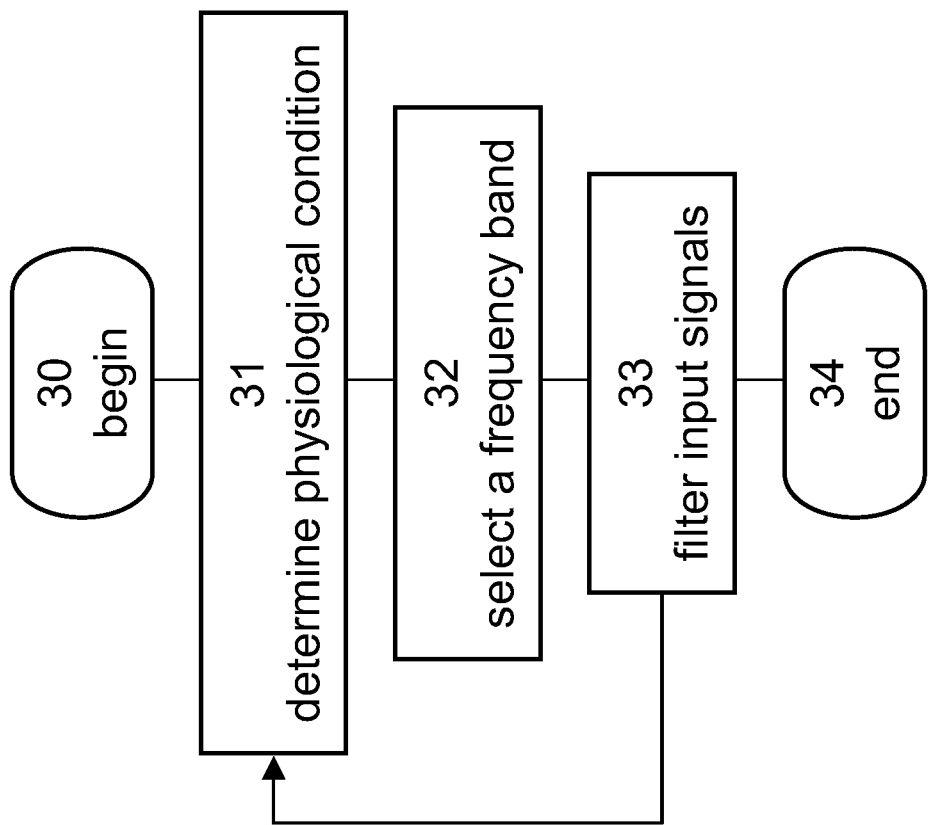

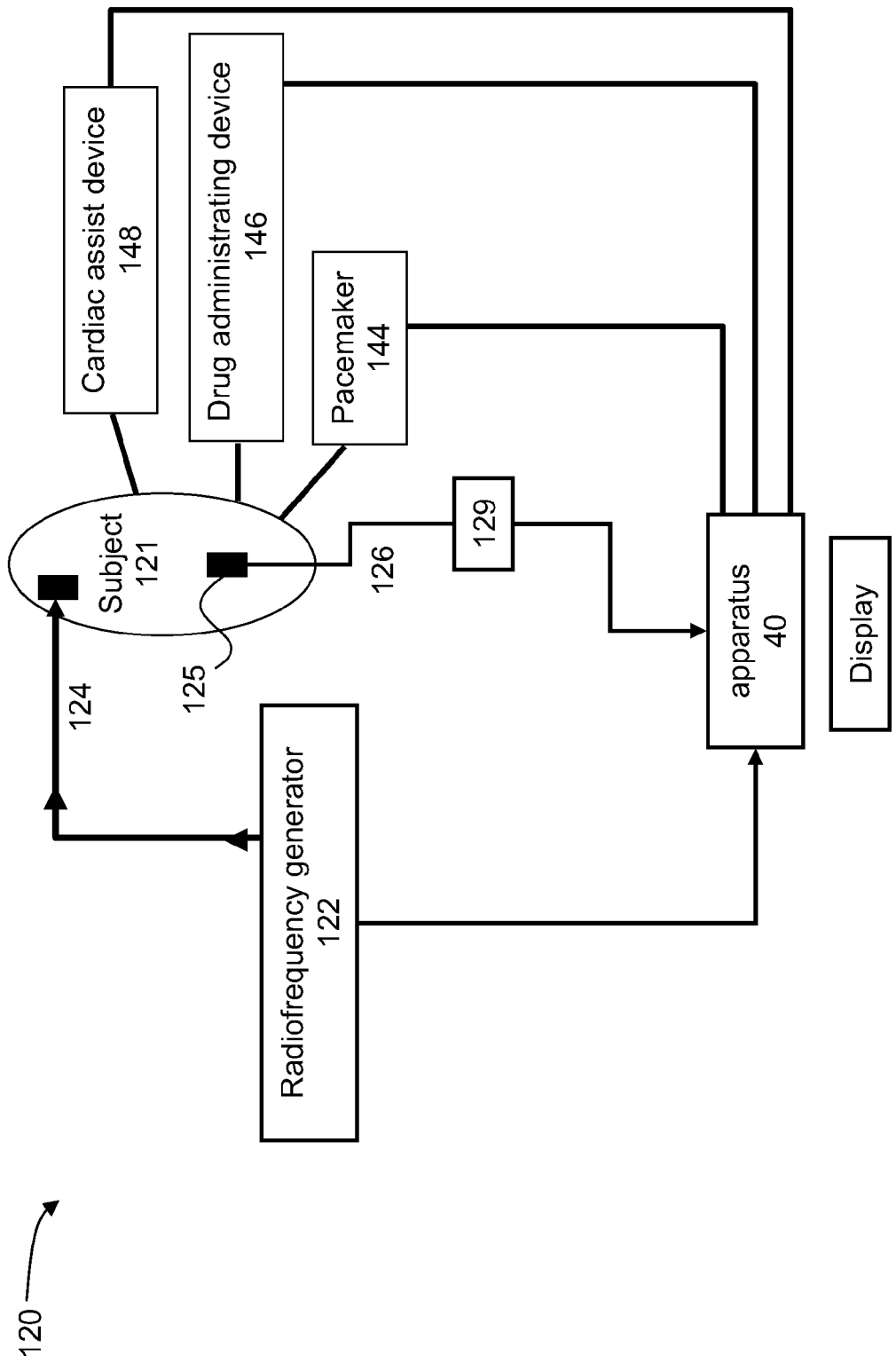

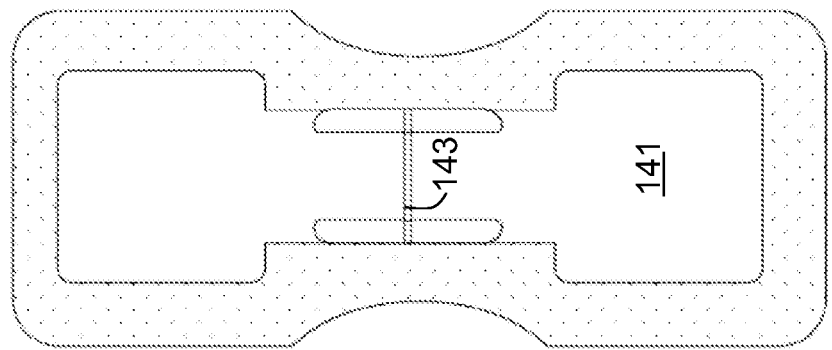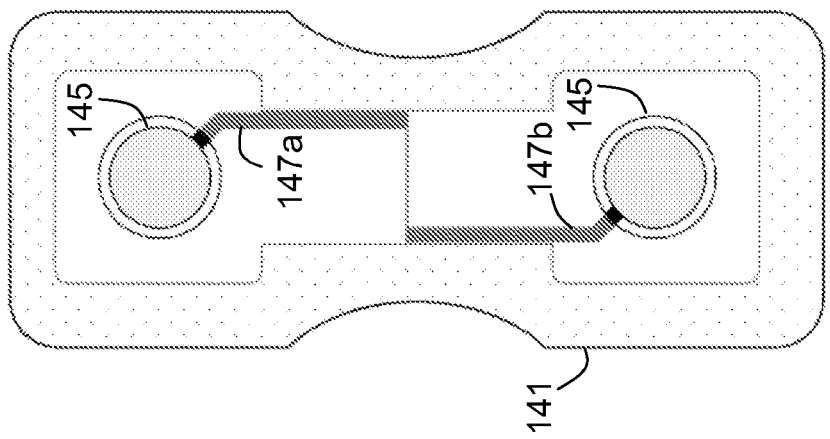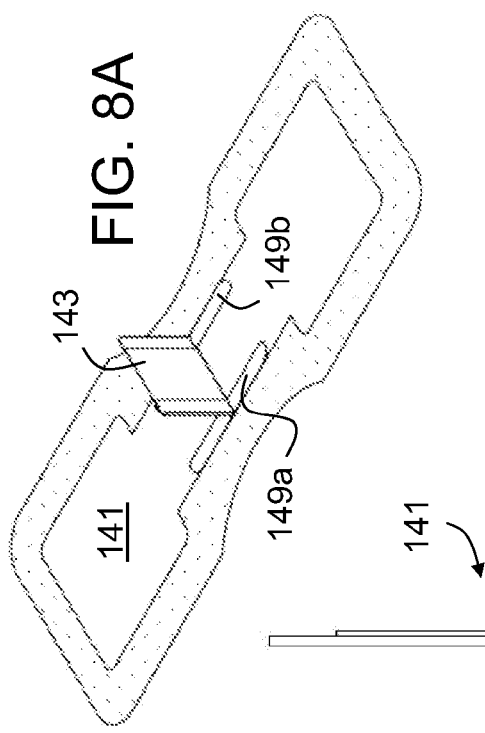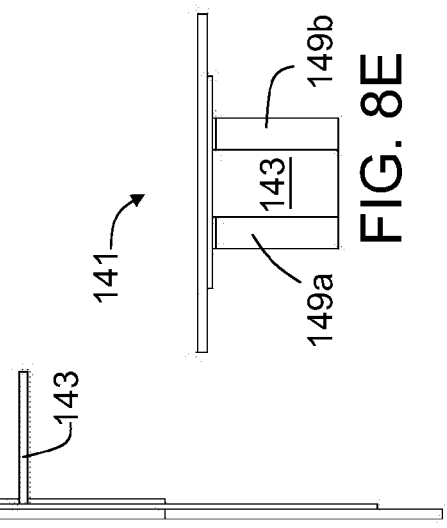

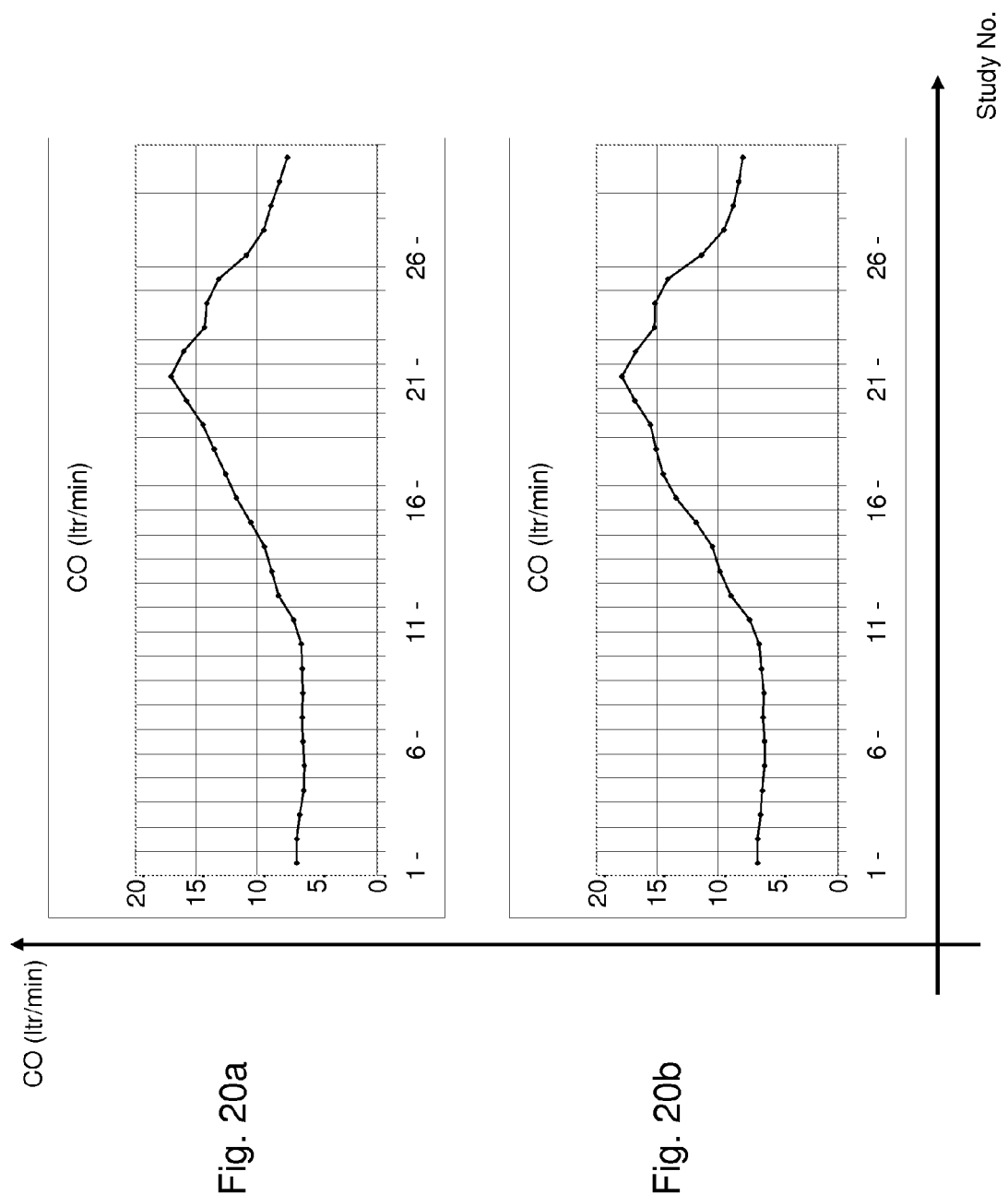

DYNAMICALLY VARIABLE FILTER

RELATED APPLICATIONS

This Application is a National Phase of PCT Patent Application No. PCT/IL2008/001105 having International filing date of Aug. 11, 2008, which is a continuation of pending U.S. patent application Ser. No. 11/889,395 filed on Aug. 13, 2007. The contents of the above Applications are all incorporated herein by reference.

FIELD AND BACKGROUND OF THE INVENTION

The present invention relates to processing of electrical signals, and more particularly to the filtering of a signal pertaining to at least one electrical property of an organ of a subject.

Technologies related to measurement of electrical properties of organs, such as the measurement of bioimpedance are generally known. Typically, such technologies relate to the monitoring of physiological parameters by extracting physiologically significant characteristics from electrical measurements, see, e.g., U.S. Pat. No. 6,577,897. Characteristics may include measures that aid in the discernment of physiological indications pertaining directly or indirectly to the state of organs (e.g., blood vessels, heart, lungs and the like), and reveal measures of various physiological conditions including critical life-threatening conditions.

For example, heart diseases may be caused by (i) a failure in the autonomic nerve system where the impulses from the central nervous system control to the heart muscle fail to provide a regular heart rate and/or (ii) an insufficient strength of the heart muscle itself where even though the patient has a regular heart rate, its force of contraction is insufficient. Either way, the amount of blood or the rate at which the blood is supplied by a diseased heart is abnormal and it is appreciated that an assessment of the state of a patient's circulation is of utmost importance.

The simplest measurements, such as heart rate and blood pressure, may be adequate for many patients, but if there is a cardiovascular abnormality then more detailed measurements are needed.

Cardiac output (CO) is the volume of blood pumped by the heart during a time interval, which is typically taken to be a minute. Cardiac output is the product of heart rate (HR) and the amount of blood which is pumped with each heartbeat, also known as the stroke volume (SV). For example, the stroke volume at rest in the standing position averages between 60 and 80 ml of blood in most adults. Thus, at a resting heart rate of 80 beats per minute the resting cardiac output varies between 4.8 and 6.4 L per min.

A common clinical problem is that of hypotension (low blood pressure); this may occur because the cardiac output is low and/or because of low systemic vascular resistance. This problem can occur in a wide range of patients, especially those in intensive care or postoperative high dependency units. In these high risk patients, more detailed monitoring is typically established including measuring central venous pressure via a central venous catheter and continuous display of arterial blood pressure via a peripheral arterial catheter.

In addition to the above measurements, the measurement of cardiac output is useful. For example, when combined with arterial pressure measurements, cardiac output can be used for calculating the systemic vascular resistance. The measurement of cardiac output is useful both for establishing a patient's initial cardiovascular state and for monitoring the response to various therapeutic interventions such as transfusion, infusion of inotropic drugs, infusion of vasoactive drugs (to increase or reduce systemic vascular resistance) or altering heart rate either pharmacologically or by adjusting pacing rate.

Several methods of measuring cardiac output are presently known, representative Examples include the Fick method, described by Adolf Fick in 1870, the amount of oxygen taken up by the body during respiration and the difference in oxygen concentration between venous and arterial blood is used to calculate the cardiac output; the transoesophageal echocardiography (see, e.g., U.S. Pat. No. 6,142,941) in which cardiac output is derived from blood flow velocity (recorded via Doppler shift) cross-sectional area of the blood vessel and heart rate; and the compliance based method (see, e.g., U.S. Pat. No. 6,485,431) in which the compliance of the arterial system is determined from measured arterial pressure and used for calculating the cardiac output as the product of the mean arterial pressure and compliance divided by a time constant. Also known are catheter based methods such as thermodilution (see, e.g., U.S. Pat. No. 4,153,048).

A non-invasive method, known as thoracic electrical bioimpedance, was first disclosed in U.S. Pat. No. 3,340,867 and has recently begun to attract medical and industrial attention [U.S. Pat. Nos. 3,340,867, 4,450,527, 4,852,580, 4,870,578, 4,953,556, 5,178,154, 5,309,917, 5,316,004, 5,505,209, 5,529,072, 5,503,157, 5,469,859, 5,423,326, 5,685,316, 6,485,431, 6,496,732 and 6,511,438; U.S. Patent Application No. 20020193689]. The thoracic electrical bioimpedance method has the advantages of providing continuous cardiac output measurement at no risk to the patient.

Various methods employing bioimpedance are found in: International Patent Application Publication Nos. WO2004098376 and WO2006087696, U.S. Pat. Nos. 6,022,322, 5,615,689 and 5,642,734, and U.S. Published Application Nos. 20030120170, 20060085048 and 20060122540, the contents of which are hereby incorporated by reference.

SUMMARY OF THE INVENTION

According to one aspect of embodiments the present invention there is provided a method of processing a signal pertaining to at least one electrical property of an organ of a subject. The method comprises determining a physiological condition of the subject, selecting a frequency band, filtering the signal according to the frequency band, and dynamically adapting the frequency band in response to a change in the physiological condition, thereby processing the signal.

According to another aspect of embodiments of the present invention there is provided a filtering device. The filtering device comprises a first input unit for receiving an input pertaining to at least one electrical property of an organ of a subject, a second input unit for receiving data pertaining to a physiological condition of the subject, and a filtering unit configured for filtering the input signal according to a frequency band which is dynamically adapted in response to a change in the physiological condition.

According to yet another aspect of embodiments of the present invention there is provided a system for monitoring cardiac output, comprising the filtering device.

According to still another aspect of embodiments of the present invention there is provided a system for predicting at least one of: a body cell mass, a fat free mass and total body water of a subject, comprising the filtering device.

According to an additional aspect of embodiments of the present invention there is provided a system for determining hematocrit of blood in a body part of a subject, comprising the filtering device.

According to yet an additional aspect of embodiments of the present invention there is provided a system for monitoring hydration status of a subject, comprising the filtering device.

According to still an additional aspect of embodiments of the present invention there is provided a system for discriminating tissue, comprising the filtering device.

According to a further aspect of embodiments of the present invention there is provided a system for calculating the circumference of a body segment, comprising the filtering device.

According to yet a further aspect of embodiments of the present invention there is provided a method of monitoring at least one electrical property of an organ of a subject. The method comprises: sensing an input radiofrequency signal from the organ, processing the input radiofrequency signal to provide a processed input signal, filtering the input signals using a dynamically variable filter to provide a filtered signal, and using the filtered signal for monitoring the at least one electrical property of the organ.

According to still a further aspect of embodiments of the present invention there is provided apparatus for monitoring at least one electrical property of an organ of a subject. The apparatus comprises an input unit for receiving an input radiofrequency signal sensed from the organ; a signal processing unit for processing the input radiofrequency signal to provide processed input signal; a filtering unit configured for filtering the input signal using dynamically variable filter to thereby provide a filtered signal; and a monitoring unit for monitoring the at least one electrical property of the organ based on the filtered signal.

According to still a further aspect of embodiments of the present invention there is provided a system for monitoring at least one electrical property of an organ of a subject. The system comprises a radiofrequency generator for generating an output radiofrequency signal and a plurality of electrodes, designed to be connectable to the skin of the subject, and configured for transmitting the output radiofrequency signal to the organ and sensing an input radiofrequency signal from the organ. The system further comprises a monitoring apparatus, e.g., the apparatus described herein.

According to further features in preferred embodiments of the invention described below, the dynamically variable filter is adapted in response to a change in a physiological condition of the subject. The filter is typically a band pass filter characterized by a frequency band defined by, e.g., a lower frequency bound and an upper frequency bound.

According to some embodiments of the present invention the physiological condition is a heart rate of the subject.

According to some embodiments of the present invention at least one of a lower bound of the frequency band and an upper bound of the frequency band parameter is a linear function of the heart rate.

According to further features in preferred embodiments of the invention described below, a lower bound of the frequency band is about $F_L(HR)$ where $F_L(HR)=0.9\times(HR/60)$ Hz and HR is a heart rate of the subject in units of beats per minute.

According to some embodiments of the present invention an upper bound of the frequency band is about $F_U(HR)$, where $F_U(HR)=6+1.5\times[(HR/60)-1]$ Hz.

According to some embodiments of the present invention the heart rate is determined from an ECG signal received from the subject.

According to some embodiments of the present invention the upper frequency bound is determined using an iterative process.

According to some embodiments of the present invention the iterative process is based on a comparison between a value of a physiological parameter as extracted from the filtered input signal and a value of the physiological parameter as extracted from a reference signal. According to some embodiments of the present invention the reference signal comprises the ECG signal. According to some embodiments of the present invention the physiological parameter is a ventricular ejection time (VET).

According to some embodiments of the present invention each iteration of the iterative process comprises: if the comparison meets a predetermined criterion, then updating the upper frequency bound by calculating an average between a low threshold for the upper bound and a high threshold for the upper bound. The thresholds can be predetermined or they can be set in a previous iteration of the iterative process.

According to some embodiments of the present invention the physiological According to some embodiments of the present invention the iterative process is terminated if a value of the VET as extracted from the filtered input signal is higher than a value of the VET as extracted from the reference signal.

According to some embodiments of the present invention the VET is averaged over a plurality of heart beats.

According to some embodiments of the present invention the VET is extracted from an average heart beat morphology of the subject.

According to some embodiments of the present invention an initial value of the upper frequency bound in the iterative process is a linear function of the heart rate. According to some embodiments of the present invention the linear function is $F_U(HR)$.

According to some embodiments of the present invention the radiofrequency signal is filtered using an analog filter.

According to some embodiments of the present invention at least one quantity is calculated using the electrical property. The quantity can be a stroke volume, a cardiac output, a brain intra luminal blood volume, a blood flow and the like.

According to some embodiments of the present invention the blood flow comprises at least one of: an external carotid blood flow rate, an internal carotid blood flow rate, an ulnar blood flow rate, a radial blood flow rate, a brachial blood flow rate, a common iliac blood flow rate, an external iliac blood flow rate, a posterior tibial blood flow rate, an anterior tibial blood flow rate, a peroneal blood flow rate, a lateral plantar blood flow rate, a medial plantar blood flow rate and a deep plantar blood flow rate.

According to some embodiments of the present invention a phase shift of the input radiofrequency signal relative to an output radiofrequency signal transmitted to the organ is determined. The phase shift can be used for calculating the quantity or quantities.

According to some embodiments of the present invention the amplitude modulation of the input radiofrequency signal is reduced or eliminated so as to provide signals of substantially constant envelope.

According to some embodiments of the present invention a phase modulation of the input radiofrequency signal is maintained while reducing or eliminating the amplitude modulation.

According to some embodiments of the present invention the input radiofrequency signal and the output radiofrequency signal are mixed so as to provide a mixed radiofrequency signal. According to some embodiments of the present invention the mixed radiofrequency signal comprises a radiofrequency sum and a radiofrequency difference.

According to some embodiments of the present invention the input radiofrequency signal is indicative of impedance the organ. According to some embodiments of the present invention the input radiofrequency signal is indicative of hemodynamic reactance of the organ.

Embodiments of the present invention successfully address the shortcomings of the presently known configurations by providing techniques for processing a signal pertaining to one or more electrical property of an organ of a subject.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 2c show a representative example of a dynamically varying frequency band, employed according to embodiments of the present invention;

FIG. 3a is a flowchart diagram of a method suitable for processing an input signal, according to various exemplary embodiments of the present invention;

FIG. 7 is a schematic illustration of a system for monitoring at least one electrical property of an organ of a subject, according to a preferred embodiment of the present invention;

FIGS. 8a-e are schematic illustrations showing perspective (FIG. 8a), front (FIG. 8b), rear (FIG. 8c), side (FIG. 8d) and top (FIG. 8e) views of a sticker which can be used for transmitting and sensing the radiofrequency signal, according to one embodiment of the present invention;

FIGS. 18a-18b, 19a-19b and 20a-20b are plots of cardiac output as calculated from a signal filtered according to various exemplary embodiments of the present invention.

DESCRIPTION OF EXEMPLARY EMBODIMENTS

Figure 1:
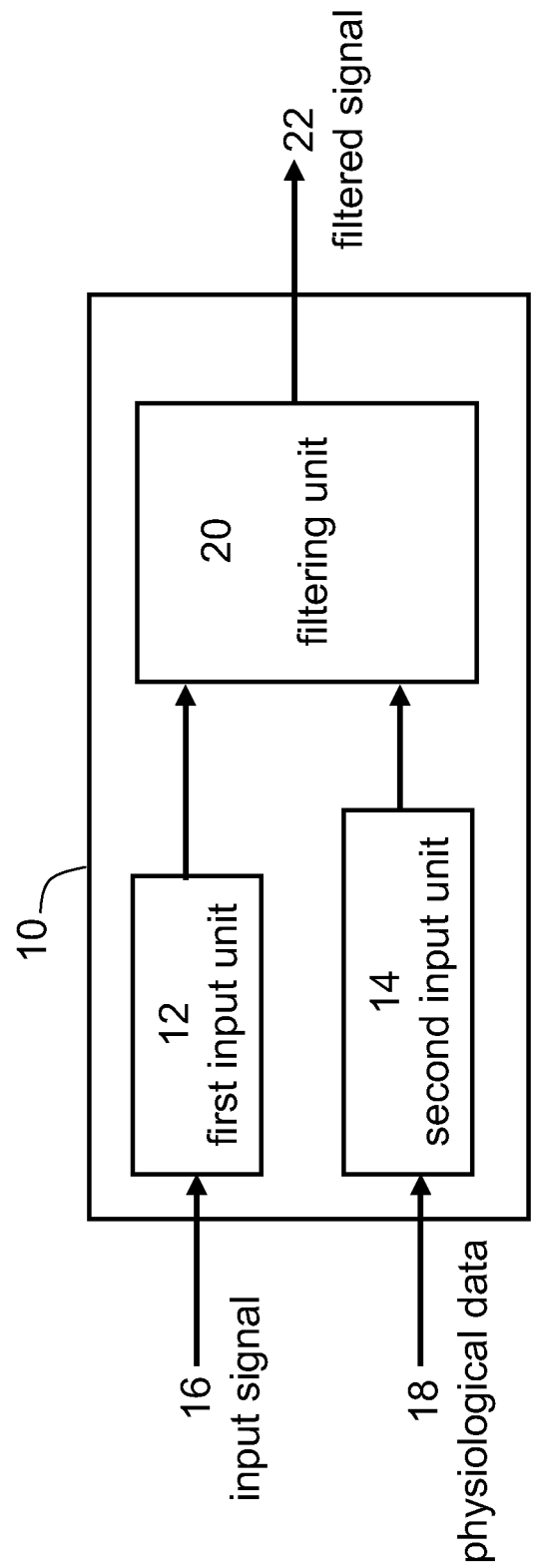
FIG. 1 is a schematic illustration of a filtering device, according to various exemplary embodiments of the present invention.

The present embodiments comprise a method, device apparatus and system which can be used for processing a signal. Specifically, but not exclusively, the present embodiments can be used for processing a radiofrequency signal sensed from an organ of a subject and for monitoring one or more electrical properties of an organ, e.g., for the purpose of determining one or more quantities which are related to electrical properties. Thus, for example, exemplary embodiments of the present invention can be used for calculating stroke volume, cardiac output, brain intra luminal blood volume and/or blood flow. Embodiments of the present invention can also be used for discriminating tissue and/or determining at least one of: body cell mass, fat free mass, total body water, hematocrit of blood, hydration status and circumference of a body segment.

The principles and operation of a method, device apparatus and system according to the present embodiments may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Computer programs implementing the method according to embodiments of the present invention can commonly be distributed to users on a distribution medium such as, but not limited to, a floppy disk, CD-ROM and flash memory cards. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

A typical system for monitoring electrical properties of a body section, such as a bioimpedance system, includes a tetrapolar array of circumferential band electrodes connected to the subject at the base of the neck and surrounding the circumference of the lower chest, at the level of the xiphoid process. When a constant magnitude alternating current flows through the upper cervical and lower thoracic band electrodes, a voltage, proportional to the thoracic electrical impedance (or reciprocally proportional to the admittance), is measured between the inner cervical and thoracic band electrodes. The portion of the cardiac synchronous impedance change, temporally concordant with the stroke volume, is ascribed solely and uniquely to volume changes of the aorta during expansion and contraction over the heart cycle. A typical printed circuit board of such system comprises one or more band pass filters, a half-wave rectification circuit and one or more low pass filters.

The present Inventor discovered techniques for reducing the noise associated with conventional systems. As demonstrated in the Examples section that follows, the present Inventor succeeded in reducing noise introduced due to patient agitation or other physiological phenomena like breathing. The present Inventor discovered techniques for separating and differentiating between a cardiovascular bioreactance signal and a respiratory bioreactance signal, where the latter is typically much larger than the former.

The present Inventor has realized that the noise level is proportional to the bandwidth of the band pass filter and that a considerable portion of the noise passes the band pass filter hence being folded into the half-wave rectification circuit.

The present Inventor also discovered techniques for reducing or eliminating AM noise hence significantly improving the ability to provide accurate measurement.

Referring now to the drawings, FIG. 1 illustrates a filtering device 10, according to various exemplary embodiments of the present invention. Device 10 comprises a first input unit 12 which receives an input signal 16 pertaining to one or more electrical properties of an organ of a subject. For example, signal 16 can relate to the hemodynamic reactance of the organ.

As used herein, "hemodynamic reactance" refers to the imaginary part of the impedance. Techniques for extracting the imaginary part from the total impedance are known in the art. Typically, such extraction is performed at hardware level but the use of algorithm at a software level is not excluded from the scope of the present invention. Signal 16 can be provided, for example, by processing a radiofrequency signal sensed from the organ, as further detailed hereinunder.

In various exemplary embodiments of the invention device 10 further comprises a second input unit 14 which receives data 18 pertaining to a physiological condition of the subject. The physiological condition is preferably, but not obligatorily, the heart rate of the subject, and the data pertaining to the physiological condition can be analog data or digital data, as desired. While the embodiments below are described with a particular emphasis to physiological condition which is a heart rate, it is to be understood that more detailed reference to the heart rate is not to be interpreted as limiting the scope of the invention in any way. For example, in exemplary embodiments of the present invention the physiological condition is a ventilation rate of the subject, a repetition rate of a particular muscle unit and/or one or more characteristics of an action potential sensed electromyography.

Device 10 further comprises a filtering unit 20 which filters the input signal 16 to provide a filtered signal 22. In various exemplary embodiments of the invention the filtering is according to a frequency band which is dynamically adapted in response to a change in the physiological condition of the subject. It was found by the Inventor of the present invention that the dynamical adaptation of the frequency band to the physiological condition of the subject can significantly reduce the influence of unrelated signals on the measured or monitoring of electrical properties of the body section.

The adaptation of the frequency band to the physiological condition can be according to any adaptation scheme known in the art. For example, one or more parameters of the frequency band (e.g., lower bound, upper bound, bandwidth, central frequency) can be a linear function of a parameter characterizing the physiological condition. Such parameter can be, for example, the number of heart beats per minute.

Figure 2A:
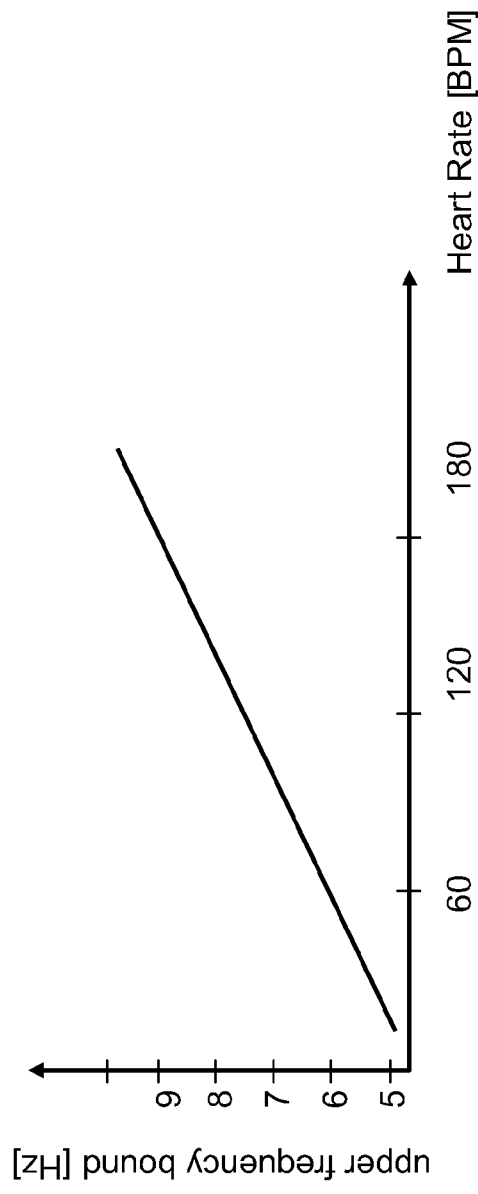
FIGS. 2a-b show a representative example of dynamically varying frequency bounds, employed according to embodiments of the present invention.
Figure 2B:
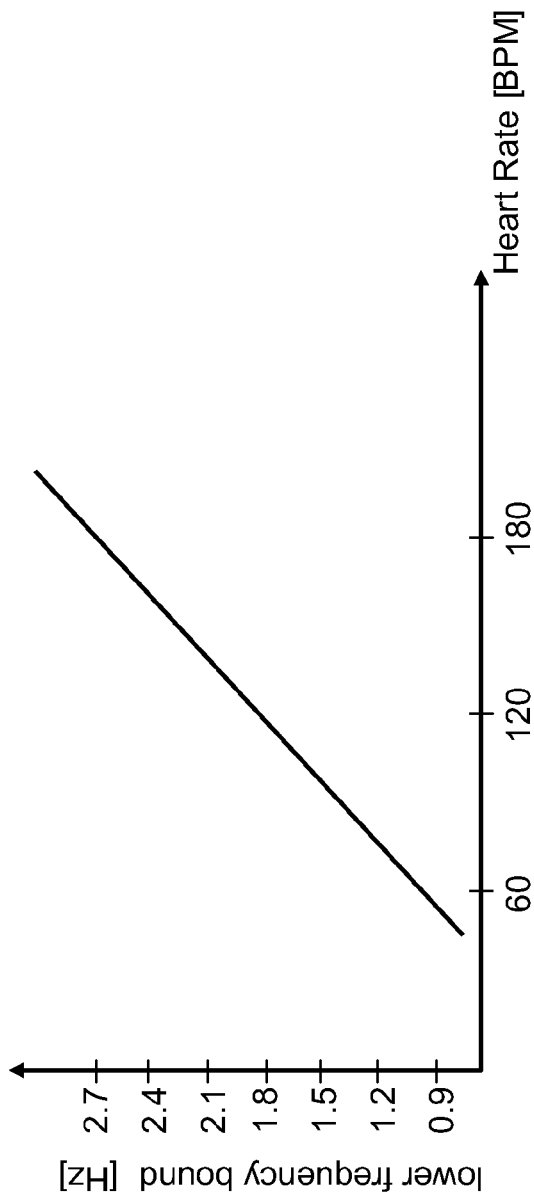

A representative example of a dynamically varying frequency bounds, employed according to some embodiments of the present invention by unit 20, is illustrated in FIGS. 2a-b. Shown in FIGS. 2a-b is the functional dependence of the frequency bounds (upper bound in FIG. 2a and lower bound in FIG. 2b) on the heart rate of the subject. As shown in FIG. 2a, the upper bound of the frequency band varies linearly such that at a heart rate of about 60 beats per minute (bpm) the upper bound is about 6 Hz, and at a heart rate of about 180 bpm the upper bound is about 9 Hz. As shown in FIG. 2b, the lower bound of the frequency band varies linearly such that at a heart rate of about 60 the lower bound is about 0.9 Hz bpm and at a heart rate of about 180 bpm the lower bound is about 2.7 Hz.

As used herein the term "about" or "approximately" refers to ±10%.

In some embodiments of the present invention the upper bound approximately equals the function $F_U(HR)$ defined as $F_U(HR)=6+1.5\times[(HR/60)-1]$ Hz, where HR is the heart rate of the subject in units of bpm. In some embodiments, the upper bound equals $F_U(HR)$ at all times, while in other embodiments, the upper bound is set using an iterative process.

In some embodiments of the present invention the lower bound approximately equals the function $F_L(HR)$ defined as $F_L(HR)=0.9\times(HR/60)$ Hz. In some embodiments, the lower bound equals $F_L(HR)$ at all times while in other embodiments the lower bound is set by an iterative process.

Representative examples of iterative process suitable for some embodiments of the present invention are provided hereinunder.

A dynamically varying band pass filter (BPF) characterized by a dynamically varying upper frequency bound and a dynamically varying lower frequency bound, according to some embodiments of the present invention is illustrated in FIG. 2c. As shown, each heart rate is associated with a frequency band defined by a lower bound and an upper bound. For example, for a heart rate of 60 bpm, FIG. 2c depicts a BPF in which the lower bound is about 0.9 Hz and the upper bound is about 6 Hz.

It is to be understood that the values presented above and the functional relations illustrated in FIGS. 2a-b are exemplary embodiments and should not be considered as limiting the scope of the present invention in any way. In other exemplary embodiments, the functional relations between the frequency band and the physiological condition can have different slopes and/or offsets, or they can be non-linear.

FIG. 3a is a flowchart diagram of a method suitable for processing an input signal, according to various exemplary embodiments of the present invention. The method can be executed by activating filtering device 10 or using any other filtering device supplemented by appropriate circuitry. Selected steps of the method can be embodied in many forms. For example, the selected steps can be embodied in on a tangible medium such as a computer for performing the selected steps. The selected steps can be embodied on a computer readable medium, comprising computer readable instructions for carrying out the selected steps. The selected steps can also be embodied in electronic device having digital computer capabilities arranged to run the computer program on the tangible medium or execute the instruction on a computer readable medium.

The method begins at step 30 and continues to step 31 in which the physiological condition of the subject is determined. The physiological condition can be, as stated, a heart rate and it can be determined using any procedure known in the art, such as, but not limited to, analysis of an electrocardiogram (ECG) signal or the like. The method continues to step 32 in which a frequency band is selected based on the physiological condition of the subject, and proceeds to step 33 in which the input signal is filtered according to frequency band. In various exemplary embodiments of the invention the method loops back to step 31 so as to dynamically adapt the frequency band in response to a change in the physiological condition.

The selection of frequency band can be according to any adaptation scheme, including, without limitation, the use of one or more linear functions (e.g., the functions $F_U$ and $F_L$) as further detailed hereinabove, and/or an iterative process as further detailed hereinbelow.

The method ends at step 34.

Following is a description of an iterative process for determining the frequency band of the band pass filter which filters the input signal according to some embodiments of the present invention. The iterative process can, in some embodiments, based a comparison between a value of a physiological parameter as extracted or calculated from the filtered input signal and a value of the same physiological parameter as extracted or calculated from a reference signal, for example, an ECG signal.

The term physiological parameter refers to any variable parameter which is measurable or calculable and is representative of a physiological activity, particularly, but not necessarily, activity of the heart. In various exemplary embodiments of the invention the physiological parameter is other than the heart rate per se. The physiological parameter can be a time-related parameter, amplitude-related parameters or combination thereof.

Typically, the filter signal and the reference signal are expressed in terms of amplitude as a function of the time. Thus, time-related parameters are typically calculated using abscissa values of the signals and amplitude-related parameters are is typically calculated using ordinate values of the signals.

Representative of time-related physiological parameters suitable for the present embodiments include, without limitation, systolic time, diastolic time, pre-ejection period and ejection time. A representative example of amplitude-related physiological parameter suitable for the present embodiments includes, without limitation, cardiac contractility, maximal amplitude above zero during a single beat, maximal peak-to-peak amplitude during a single beat, and RMS level during a single beat. Also contemplated are various slopes parameters, such as, but not limited to, the average slope between two points over the signal.

In various exemplary embodiments of the invention the physiological parameter is a ventricular ejection time (VET).

While the embodiments below are described with a particular emphasis to VET as the physiological parameter, it is to be understood that more detailed reference to VET is not to be interpreted as limiting the scope of the invention in any way.

The present inventors discovered that a significant amount of the biological information for a particular subject can be obtained from a frequency range between $F_L(HR)$ and 5.5 Hz, where HR is the heart rate of the subject. It was further discovered by the present inventors that for some medical conditions some of the information can reside between 5.5 Hz and $F_U(HR)$.

The advantage of the comparison between two different techniques for extracting or calculating the same physiological parameter, is that it allows to substantially optimize the upper frequency bound of the of the band pass filter. In various exemplary embodiments of the invention in each iteration of the iterative process, the comparison is repeated. If the comparison meets a predetermined criterion, the upper frequency bound is updated by calculating an average between a low threshold for the upper bound and a high threshold for the upper bound. The lower frequency bound can be a constant bound, e.g., a constant frequency which is from about 0.9 Hz to about 2.7 Hz), or it can be dynamic, e.g., $F_L(HR)$, HR being the heart rate of the subject before or during the respective iteration.

The low and high thresholds for the upper bound can be set in more than one way. In some embodiments, the low and high thresholds are predetermined (namely they determined a priori before the iterative process), in some embodiments, the thresholds are set in a previous iteration of iterative process, in some embodiments one of the thresholds is predetermined and the other threshold is set in a previous iteration of iterative process. In any event, the first iteration is based on two thresholds which are determined a priori before the iterative process. It was found by the inventors of the present invention that, at least initially (i.e., at the first iteration), the first threshold can be about $F_U(40)$, which in various exemplary embodiments of the invention is about 5.5 Hz, and the second threshold can be the calculated value of $F_U(HR)$, HR being the heart rate of the subject before or during the respective iteration.

The predetermined criterion used during the iterations can be, for example, that the results of the two calculations are similar (e.g., within about 40% or 30% or 25% of each other). The predetermined criterion can also relate to the direction of difference between the two calculations. Broadly, for time-related parameters, the upper bound is updated if the value of the parameter as calculated based on the reference signal is higher than value of the parameter as calculated based on the filtered signal, and for amplitude-related parameters the upper bound is updated if the value of parameter as calculated based on the reference signal is lower than the value of the parameter as calculated based on the filtered signal. For slope-related parameters, the upper bound is typically updated if the value of the parameter as calculated based on the reference signal is higher than the value of the parameter as calculated based on the filtered signal.

A Boolean combination between the above criteria can also be used as a criterion. For example, an AND Boolean combination can be employed in which case the upper frequency bound can be updated if the results of the two calculations are similar and the calculation according to the filtered signal indicates an abnormal physiological condition while the calculation according to the reference signal indicates a normal physiological condition.

Figure 3B:
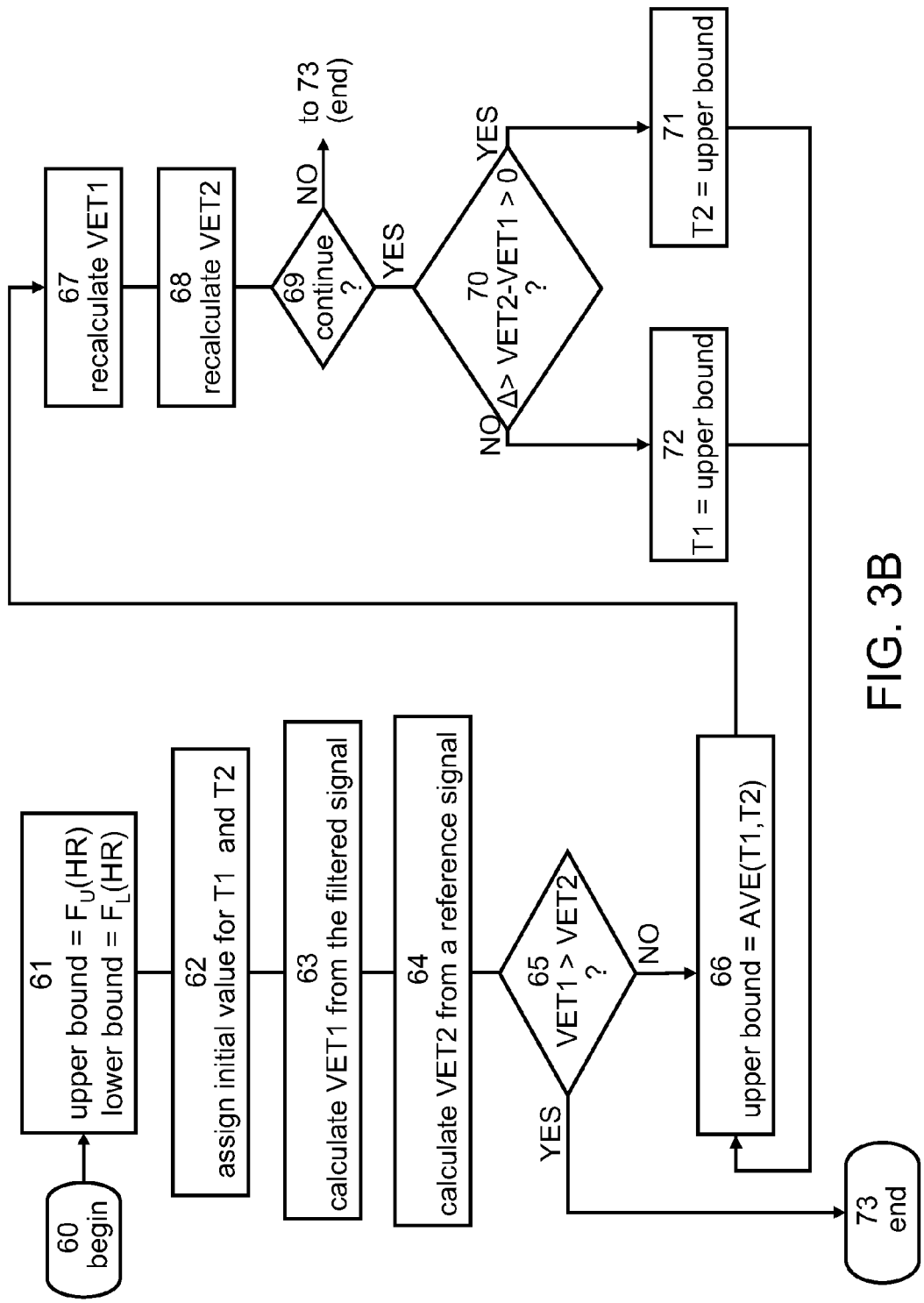
FIG. 3b is a flowchart diagram of an iterative process for selecting a frequency bound, according to various exemplary embodiments of the present invention.

FIG. 3b is a flowchart diagram of an iterative process for selecting the upper frequency bound, according to various exemplary embodiments of the present invention. The description is for a physiological parameter which is VET, but, as stated, it is not intended to limit the scope of the present invention to this type of physiological parameter.

The iterative process begins at 60 and continues to 61 in which the upper frequency bound is set to the value of $F_U(HR)$, HR being the heart rate of the subject before the initiation of the iterative process. The heart rate can be inputted or it can be determined by the process, e.g., from the ECG signal. The process continues to 62 in which initial values are assigned to two frequency thresholds. The frequency thresholds are denoted in FIG. 3b by T1 and T2. In various exemplary embodiments of the invention the initial value of T1 is $F_U(40)$ and the initial value of T2 is the initial upper frequency bound.

The process continues to 63 and 64 in which VET is calculated separately from the filtered input signal (63) and from a reference signal (64), e.g., ECG. The VET as calculated from the input signal is denoted in FIG. 3b VET1 and the VET as calculated from the ECG signal is denoted in FIG. 3b VET2. In the first iteration, the filtered signal from which VET1 is calculated is preferably obtained by filtering the input signal using a band pass filter defined between the upper and lower frequency bounds as initially set at 61.

The process continues to decision 65 in which VET1 and VET2 are compared. If VET1 is higher than VET2, the iterative process continues to 73 where it is terminated. If VET1 is not higher than VET2, the process continues to 66 in which the upper bound is updated to the average AVE of T1 and T2. In various exemplary embodiments of the invention AVE(T1, T2) is the arithmetic mean of T1 and T2 (i.e., AVE(T1, T2)= (T1+T2)/2), this need not necessarily be the case, since, in some embodiments, a different averaging scheme (e.g., a weighted average, a geometric mean, harmonic mean, RMS, etc.) can be employed.

From 66 the process continues to 67 in which VET1 is recalculated but from a signal which is filtered using an updated band pass filter. The lower bound of the updated band pass filter can be the initial lower bound or it can be updated based on the heart rate of the subject immediately before the filtration of the input signal (e.g., according to $F_L$ described above). The upper bound of the updated band pass filter is preferably the updated upper bound. Optionally, the process continues to 68 in which the VET2 is also recalculated from the reference signal. Alternatively, the value of VET2 from 64 can be used.

The process then continues to decision 69 in which the process determines whether or not a predetermined termination criterion is met. If the predetermined termination criterion is met, the iterative process continues to 73 where it is terminated, otherwise the process continues to decision 70 in which VET1 and VET2 are compared. If the deviation between VET1 and VET2 is lower than a predetermined threshold Δ and VET1 is lower than VET2, the process continues to 71 at which the value of the upper bound is assigned to T2, otherwise the process continues to 72 at which the value of the upper bound is assigned to T1.

From 71 and 72 the process loops back to 66 at which an additional iteration begins.

The threshold Δ employed at decision 70 is typically expressed as a fraction of VET2 or a fraction of (VET2−VET1)/VET2. In various exemplary embodiments of the invention Δ=p*VET2, where p<0.5, for example, p=0.4 or p=0.3 or p=0.25.

The termination criterion employed at decision 69 can be for example, a maximal number of iterations. In this embodiment, the process counts the number of iterations and compares them to a predetermined iteration number threshold. If the number of iterations exceeds iteration number threshold the process determines that the termination condition is met and continues to end 73. Typically, but not necessarily, the value of the predetermined iteration number threshold is from about 3 iterations to about 10 iterations, e.g., 5 or 6 iterations.

The termination criterion can also include a comparison of the value of VET1 to a predetermined VET threshold $T_{VET}$, which may be absolute, subject-specific or relative to VET2. It this embodiment, the process compares the value of VET1 to $T_{VET}$. If VET1 is higher than $T_{VET}$ the process determines that the termination condition is met and continues to end 73. Typically, but not necessarily, a relative value of $T_{VET}$ is employed. For example, in various exemplary embodiments of the invention $T_{VET}$=p*VET2 where p<0.5, for example, p=0.4 or p=0.3 or p=0.25.

In any of the above embodiment, the VET (either VET1 or VET2) can be calculated over a single heart beat, or, more preferably, it can be averaged over two or more heart beats. The advantage of using an averaging procedure rather than using a single beat is that it attenuates random disturbances which may be present in the signal during the iterative process. Nevertheless, extraction of the VET from a single beat is not excluded from the scope of the present invention.

For a single heart beat, the calculation of VET can be performed by characterizing the morphology of the beat, identifying two or more identifiable points on the beat and measuring the time between the identified points.

Figure 3E:
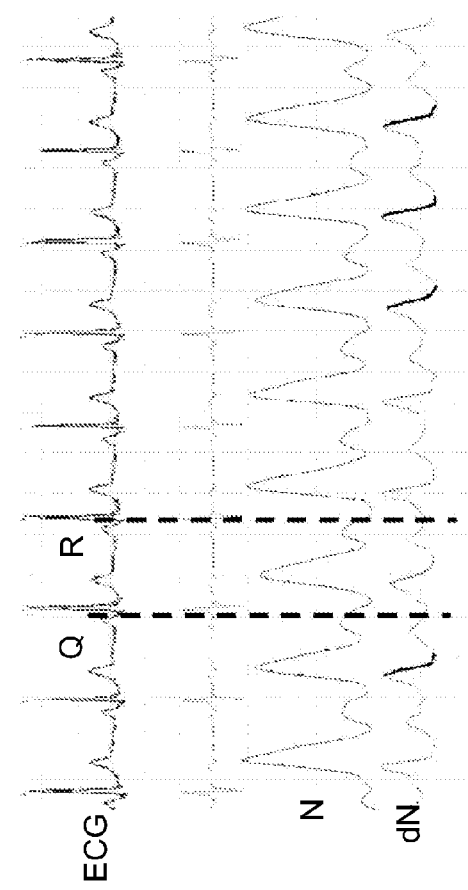
FIGS. 3e-f are schematic illustrations of beat morphology characterization procedures, according to various exemplary embodiments of the present invention.
Figure 3F:
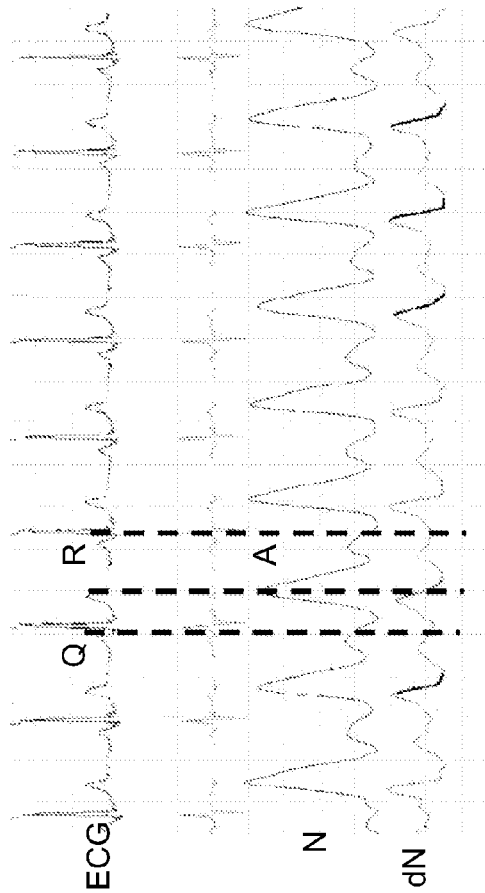
Figure 3C:
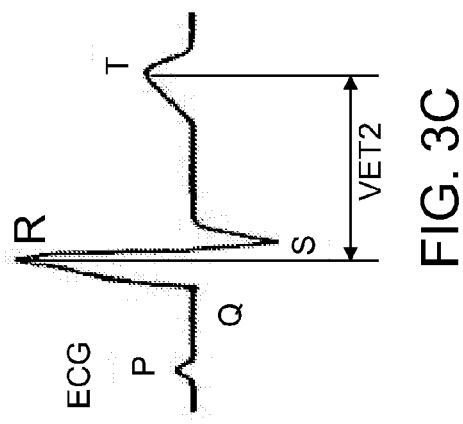
FIG. 3c is a schematic illustration of a procedure for extracting ventricular ejection time from an ECG signal.

FIG. 3c illustrates a procedure for extracting VET2 when the reference signal is an ECG signal. Shown in FIG. 3c is a typical morphology of a single beat of an ECG signal as a function of the time. VET2 can be defined as the time period (difference between the abscissa values) between the R peak and the T peak of the ECG signal.

Figure 3D:
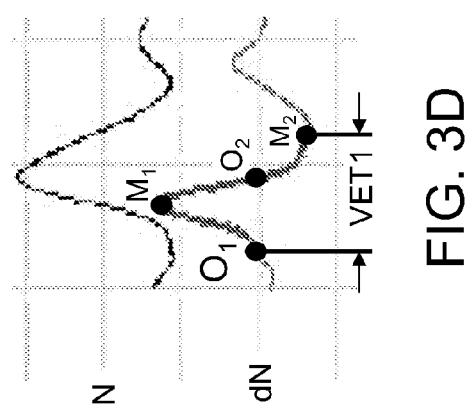
FIG. 3d is a schematic illustration of a procedure for extracting ventricular ejection time from a derivative of a filtered signal according to various exemplary embodiments of the present invention.

When the filtered signal is hemodynamic reactance, the value of VET1 is preferably extracted from the first derivative of the filtered signal. The procedure is illustrated in FIG. 3d, which illustrates a typical morphology of a single beat of the hemodynamic reactance N and its first derivative dN, as a function of the time. As shown, dN has two zeroes $O_1$ and $O_2$ over the beat, with a point of local maximum $M_1$ between the zeroes and a point of local minimum $M_2$ after the second zero. In some embodiments of the present invention VET1 is defined as the time period (difference between the abscissa values) between the first zero $O_1$ and the first minimum $M_2$ after the second zero $O_2$.

The beat morphology of the filtered signal can be characterized by identifying identifiable points on the reference signal and using the time associated with these points (abscissa values) for defining anchor points on the filtered signal.

Two exemplary beat morphology characterization procedure of the filtered signal for embodiments in which the input signal is the hemodynamic reactance and the reference signal is the ECG signal are illustrated in FIGS. 3e-f.

In FIG. 3e, a single beat of dN (first derivative of the hemodynamic reactance N) is defined between two anchor endpoints: a first (left) endpoint has the abscissa value of the Q peak of the ECG signal, and a second (right) endpoint has the abscissa value of the R peak of the next ECG signal. In other words, a single beat of dN has a width which equals the following sum of five successive intervals over the ECG: QR+RS+ST+TQ+QR.

In FIG. 3f, a single beat of dN is defined using three anchor points: the two anchor endpoints as described in FIG. 3e and an intermediate anchor point which has the abscissa value of the global maximum A of the hemodynamic reactance N between the two endpoints.

When the VET is averaged, the calculation can be done in more than one way.

In some embodiments, the same morphology characterization is employed for a plurality of beats over a predetermined interval of the respective signal, so as to provide one local VET for each beat. The VET can be defined as the average of all local VETs. Any averaging procedure can be employed, include, without limitation, arithmetic mean, weighted average, geometric mean, harmonic mean, RMS and the like.

In some embodiments, the morphologies of the beats are averaged over an ensemble of beats in the filtered signal, to provide an average beat morphology, and the VET is be determined by identifying two or more identifiable points on the average beat morphology and measuring the time between the identified points. For example, for each beat in the ensemble, the morphology can be characterized as described above and all the morphologies can be averaged, e.g., point by point. The morphologies can also be averaged in segments. This embodiments is particularly useful when a single beat is defined using more than two anchor points in which case each segment over the beats (between two successive anchor points) can be averaged, e.g., point-by-point. The average beat morphology can then be obtained by stitching the averaged segments. For example, in the embodiment illustrated in FIG. 3f the beat is defined using two intermediate anchor points and an intermediate point. In this embodiment, each beat has a left segment (from the abscissa value of Q to the abscissa value of A) and a right segment (from the abscissa value of A to the abscissa value of R). The left segments of all beats in the ensemble can be averaged to provide a left segment average, and the right segments of all beats in the ensemble can be averaged to provide a right segment average. The average beat morphology can be obtained by stitching the left segment average to the right segment average.

In various exemplary embodiments of the invention the time scale of the beats in the ensemble is adjusted so as to fit all the beats in the ensemble to a single time scale.

The result of this average is a single beat morphology from which VET1 can be extracted as described above. For example, when the first derivative of the hemodynamic reactance is used, the average morphology typically has the shape illustrated in FIG. 3d. VET1 can then be extracted as the time period between $O_1$ and $O_2$. The first derivative of the signal can be calculated before or after averaging. When the first derivative is calculated before the averaging, the averaging procedure described above is performed with respect to the derivative of the signal. When the first derivative is calculated after the averaging, the averaging procedure described above is performed with respect to the signal and the obtained average is then differentiated. Calculation of the first derivative after averaging is preferred from the standpoint of noise reduction.

The predetermined time period over which an averaging procedure is performed to extract the VET typically extends over about 10 heart beats.

A particular advantage of the device and method of the present embodiments is that they can be implemented in many systems designed for measuring or monitoring electrical properties of body sections, thereby improving their performance, e.g., by increasing their signal to noise ratio at least for situations in which the amount of noise is high. Representative examples of such systems include, without limitation, a system for monitoring blood flow, cardiac output and/or stroke volume, which can be similar to or based on the systems disclosed in U.S. Published Application No. 2006020033 and International Patent Publication No. WO2006/087696, the contents of which are hereby incorporated by reference; a system for predicting body cell mass, fat free mass and/or total body water of a subject, which can be similar to or based on the system disclosed in U.S. Pat. No. 5,615,689, the contents of which are hereby incorporated by reference; a system for determining hematocrit of blood in a body part of a subject, which can be similar to or based on the system disclosed in U.S. Pat. No. 5,642,734, the contents of which are hereby incorporated by reference; a system for monitoring hydration status of a subject, which can be similar to or based on the system disclosed in U.S. Published Application No. 20030120170, the contents of which are hereby incorporated by reference; a system for discriminating tissue, which can be similar to or based on the system disclosed in U.S. Published Application No. 20060085048, the contents of which are hereby incorporated by reference; and a system for calculating the circumference of a body segment which can be similar to or based on the system disclosed in U.S. Published Application No. 20060122540, the contents of which are hereby incorporated by reference.

Figure 4:
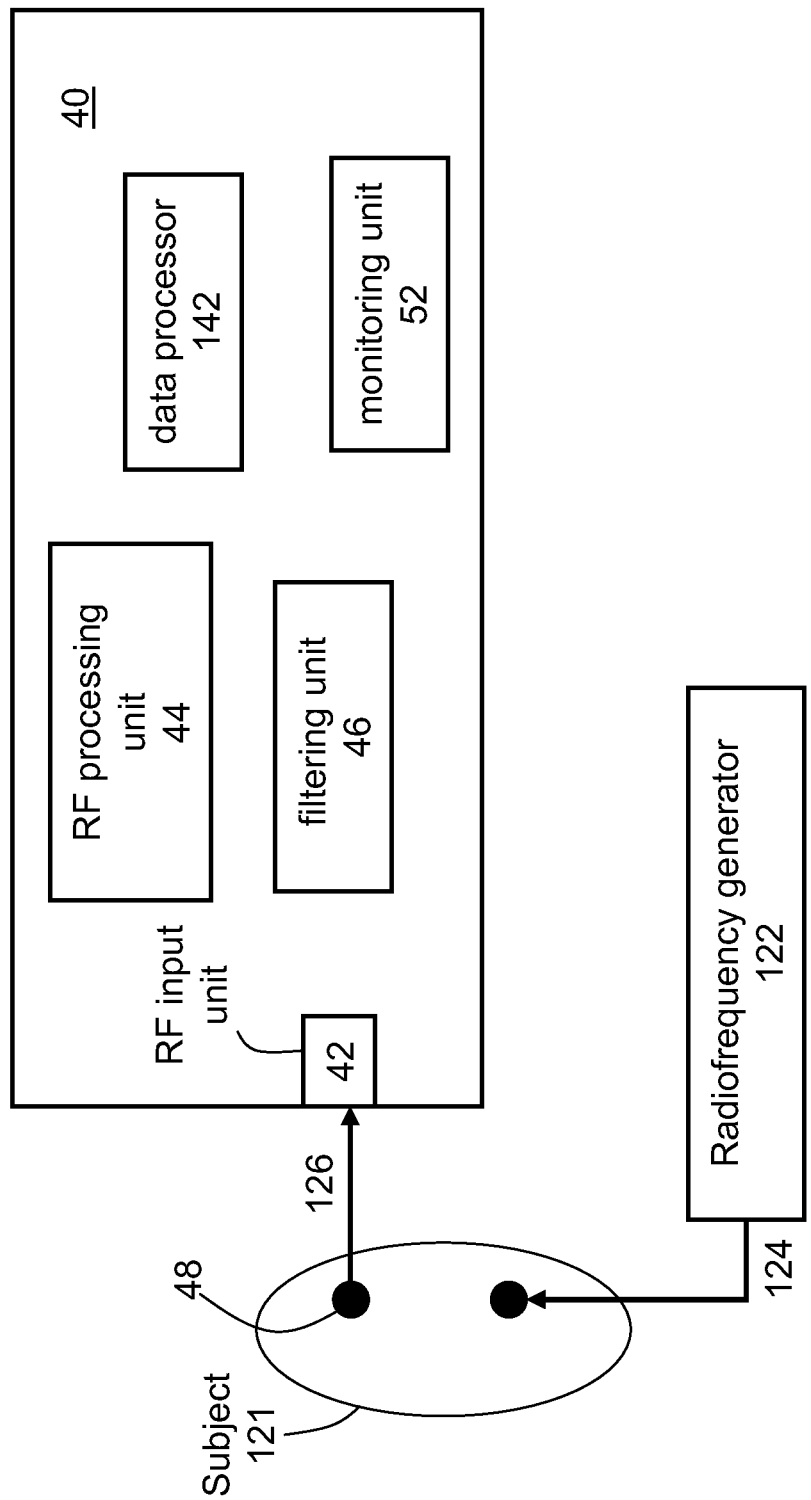
FIG. 4 is a schematic illustration of apparatus for monitoring one or more electrical properties of an organ of a subject, according to various exemplary embodiments of the present invention.

Reference is now made to FIG. 4 which is a schematic illustration of apparatus 40 for monitoring one or more electrical properties of an organ of a subject 121, according to various exemplary embodiments of the present invention.

Apparatus 40 comprises an input unit 42 for receiving an input radiofrequency signal sensed from the organ. The input radiofrequency signal typically comprises a radiofrequency signal related to the electrical properties of the organ (e.g., bioimpedance which may generally relate to the impedance and/or hemodynamic reactance of the organ). The signal is sensed from one or more sensing locations 48 on the organ of subject 121 and is originated from an output radiofrequency signal 124 generated by a radiofrequency generator 122. The input radiofrequency signal, however, can include one or more noise components, which may be introduced into the signal due to various reasons, e.g., subject agitation or breathing. In various exemplary embodiments of the invention apparatus 40 is capable of reducing or eliminating these noise components.

Apparatus 40 further comprises a signal processing unit 44 which processes the input radiofrequency signal. The processing may include, for example, mixing, demodulation, determination of phase shift, analog filtering, sampling and any combination thereof. Signal processing unit 44 may or may not be in communication with radiofrequency generator 122, as desired. A representative example of signal processing unit 44 is provided hereinunder with reference to FIG. 5.

Apparatus 40 further comprises a filtering unit 46 which filters the processed input signal. Unit 46 preferably performs the filtration operation in the frequency domain. Thus, in various exemplary embodiments of the invention, a series of samples of the processed radiofrequency signal is transformed, e.g., by a Fast Fourier Transform (FFT), to provide a spectral decomposition of the signal in the frequency domain. The transformation to the frequency domain can be done by a data processor. Algorithms for performing such transformations are known to those skilled in the art of signal processing.

The obtained spectral decomposition of the signal is filtered by unit 46 which typically eliminates one or more of the frequencies in the spectrum, depending on the upper and lower frequency bounds of the filter employed by unit 46. Unit 46 preferably employs a dynamically variable filter. For example, unit 46 can comprise filtering device 10 as described above.

Once filtered, the signal is transmitted to a monitoring unit 52 which monitors the electrical property or properties of the organ based on filtered signal. Unit 52 can monitor the electrical property by recording it and/or transmitting it to an external device, such as a display device and/or a computer. The dynamically variable filter can be adapted in response to a change in the physiological condition of the subject, as further detailed hereinabove.

Apparatus 40 is optionally and preferably designed for determining a phase shift $\Delta\phi$ of signal 126 relative to signal 124. This can be done using a phase shift determinator 50 (not shown, see FIG. 5) which can operate according to any known technique for determining a phase shift. The phase shift can be determined for any frequency component of the spectrum of radiofrequency signals received from the organ. For example, in one embodiment, the phase shift is determined from the base frequency component, in another embodiment the phase shift is determined from the second frequency component, and so on. Alternatively the phase shift can be determined using several frequency components, e.g., using an appropriate averaging algorithm.

It was discovered by the Inventor of the present invention that the phase shift of the input signal, as received from the organ, relative to the output signal as generated by generator 122, is indicative of the blood flow in the organ. Thus, according to some embodiments of the invention the blood flow is determined using the phase shift ($\Delta\phi$).

The advantage of using $\Delta\phi$ for determining the blood flow is that the relation between the blood flow and $\Delta\phi$ depends on fewer measurement-dependent quantities as compared to prior art determination techniques in which the impedance is used. Specifically, it was found by the Inventor of the present invention that there is a linear relationship between $\Delta\phi$ and the blood flow, with a proportion coefficient comprising the systolic ejection time, T. For example, the stroke volume SV can be calculated using the relation SV=const.$\times$T$\times\Delta\phi$, and the cardiac output CO can be calculated using the relation CO=const.$\times$T$\times\Delta\phi\times$HR, where HR is the heart rate of the subject (e.g., in units of beats per minute), and "const." a constant which can be found, for example, using a calibration curve. As will be appreciated by one ordinarily skilled in the art, the absence of L and $Z_0$ from the formulae for SV and CO significantly reduces the uncertainty in the obtained values because there is no entanglement between the obtained values and errors associated with the measurement of L and $Z_0$.

In various exemplary embodiments of the invention apparatus 40 comprises a data processor 142, configured for calculating at least one quantity using the filtered signal. Data processor 142 can also be employed by unit 46 for performing the transformation to the frequency domain and/or eliminating the frequency components according to the dynamically variable frequency bounds.

Many quantities may be calculated by data processor 142. For example, in various exemplary embodiments of the invention processor 142 calculates blood-volume related quantities, such as, but not limited to, a stroke volume, a cardiac output and a brain intra luminal blood volume. In the embodiments in which data processor 142 is employed, monitoring unit 46 can monitor the quantity calculated by processor 142. When apparatus 40 codetermines the phase shift, processor 142 can calculate the quantity based on the phase shift.

Figure 5:
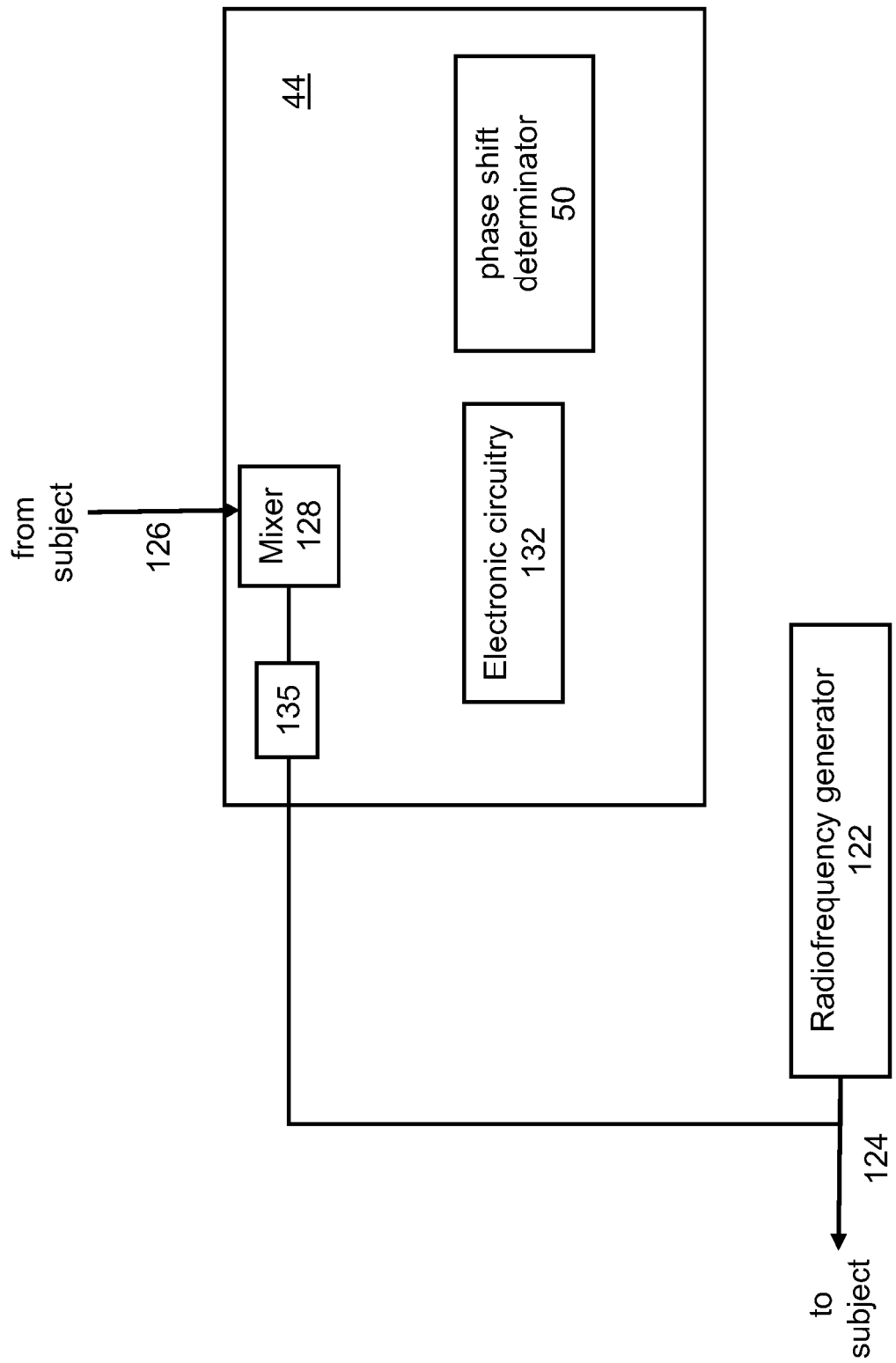
FIG. 5 is a schematic illustration of a signal processing unit, according to various exemplary embodiments of the present invention.

Reference is now made to FIG. 5 which schematically illustrates signal processing unit 44, according to various exemplary embodiments of the present invention. Unit 44 preferably comprises a mixer 128, electrically communicating with generator 122, for mixing signal 124 and signal 126, so as to provide a mixed radiofrequency signal. Signals 124 and 126 may be inputted into mixer 128 through more than one channel, depending on optional analog processing procedures (e.g., amplification) which may be performed prior to the mixing.

Mixer 128 may be any known radiofrequency mixer, such as, but not limited to, double-balanced radiofrequency mixer and unbalanced radiofrequency mixer. According to a preferred embodiment of the present invention, the mixed radiofrequency signal is composed of a plurality of radiofrequency signals, which may be, in one embodiment, a radiofrequency sum and a radiofrequency difference. A sum and a difference may be achieved, e.g., by selecting mixer 128 such that signal 124 and signal 126 are multiplied thereby. Since a multiplication between two frequencies is equivalent to a frequency sum and a frequency difference, mixer 128 outputs a signal which is composed of the desired radiofrequency sum and radiofrequency difference.

The advantage in the production of a radiofrequency sum and a radiofrequency difference is that whereas the radiofrequency sum includes both the signal, which is indicative of the electrical property, and a considerable amount of electrical noise, the radiofrequency difference is approximately noise-free.

It was found by the present Inventor that this technique is suitable for minimizing the electrical noise even when the effect of interest is smaller than the measured quantity by 2-4 orders of magnitude.

According to various exemplary embodiments of the present invention unit 44 further comprises a phase shift determinator 50 for determining the phase shift of the input signal relative to the output signal. Phase shift determinator 50 can determine the phase shift according to any technique known in the art. For example, the phase shift can be determined from the radiofrequency difference outputted from mixer 128.

According to a preferred embodiment of the present invention processing unit 44 further comprises electronic circuitry 132, which filters out a portion of the signal such that a remaining portion of the signal is characterized by a substantially increased signal-to-noise ratio.

Figure 6:
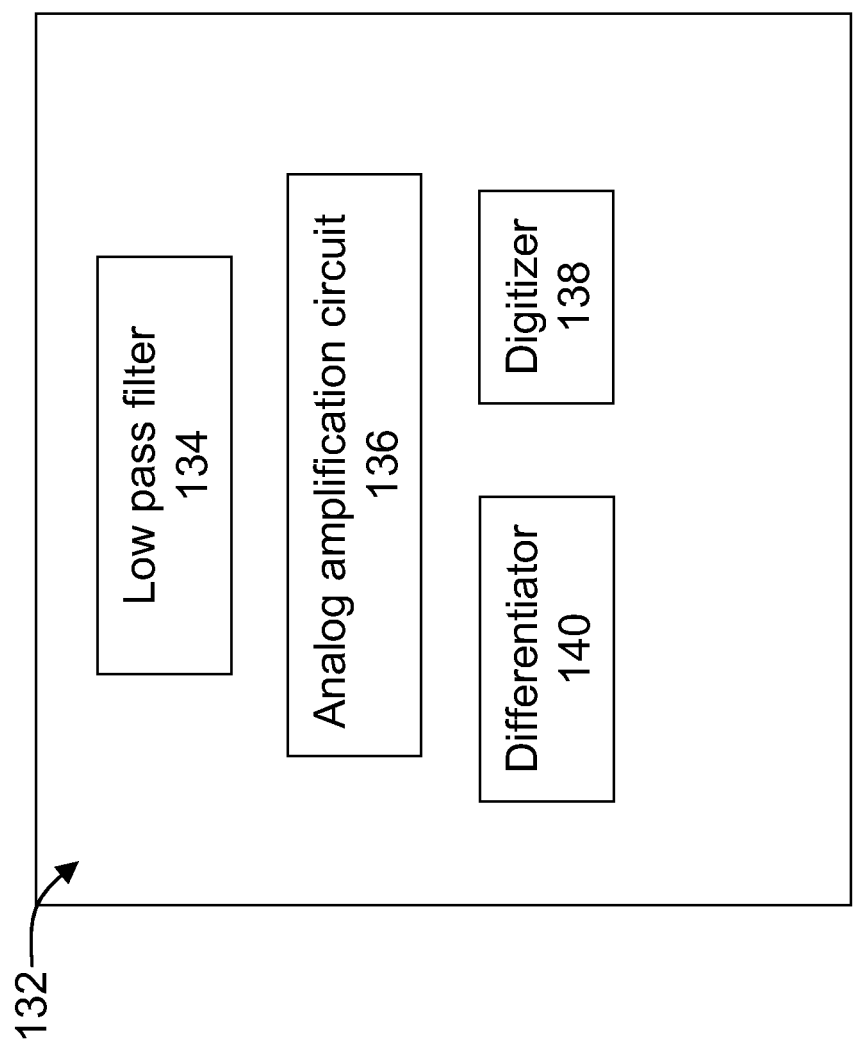
FIG. 6 is a block diagram of electronic circuitry, according to various exemplary embodiments of the present invention.

Circuitry 132 is better illustrated in FIG. 6. According to an embodiment of the present invention circuitry 132 comprises a low pass filter 134 to filter out the high frequency content of the signal. Low pass filter 134 is particularly useful in the embodiment in which mixer 128 outputs a sum and a difference, in which case low pass filter 134 filters out the radiofrequency sum and leaves the approximately noise-free radiofrequency difference. Low pass filter 134 may be designed and constructed in accordance with the radiofrequency difference of a particular system which employs apparatus 40. A judicious design of filter 134 substantially reduces the noise content of the remaining portion. In a conventional bioimpedance system, for example, a substantial amount of the noise of the received signal is folded into the remaining signal, which is thus characterized by a bandwidth of about 2 kilohertz. It has been found by the inventor of the present invention that by including output radiofrequency signal 124 and by mixing it with input radiofrequency signal 126, the noise in the resulting signal is characterized by a bandwidth that is at least one order of magnitude below the noise bandwidth of conventional systems.

In various exemplary embodiments of the invention mixer 128 and circuitry 132 are designed and constructed for increasing the signal-to-noise ratio by at least 20 dB, more preferably by 25 dB, most preferably by 30 dB.

Circuitry 132 preferably comprises an analog amplification circuit 136 for amplifying the remaining portion of the signal. The construction and design of analog amplification circuit 136 is not limited, provided circuit 136 is capable of amplifying the signal. A non limiting example of amplification circuit 136 is further detailed herein below in the Examples section that follows.

According to a preferred embodiment of the present invention circuitry 132 further comprises a digitizer 138 for digitizing the signal. The digitization of the signal is useful for further digital processing of the digitized signal, e.g., by a microprocessor.

Optionally, circuitry comprises a differentiator 140 (either a digital differentiator or an analog differentiator) for performing at least one time-differentiation of the measured impedance to obtain a respective derivative (e.g., a first derivative, a second derivative, etc.) of the electrical property. Differentiator 140 may comprise any known electronic functionality (e.g., a chip) that is capable of performing analog or digital differentiation. Time-derivatives are useful, for example, when the electrical property is bioimpedance and the apparatus is employed in a system for measuring stroke volume or cardiac output, as further detailed hereinafter.

According to a preferred embodiment of the present invention signal processing unit 44 comprises an envelope elimination unit 135 which reduces or, more preferably, eliminates amplitude modulation of signal 126. Optionally and preferably, unit 135 maintains the phase modulation of signal 126. The input to envelope elimination unit 135 typically carries a substantial amount of AM noise, which can be described, without limitation as a signal $v_{26}=v(t)\cos(\omega t+\phi(t))$, which contains both phase and amplitude modulation. According to a preferred embodiment of the present invention unit 135 generates a signal having a substantial constant envelope, e.g., $v_{26}=v_{26}\cos(\omega t+\phi(t))$, where $v_0$ is substantially a constant. The output of unit 135 thus represents the phase (or frequency) modulation of signal 126. Unit 135 can employ, for example, a limiter amplifier which amplifies signal 126 and limits its amplitude such that the amplitude modulation is removed. The advantage of the removal of the amplitude modulation is that it allows a better determination of the phase shift $\Delta\phi$ between the input and output signals, as further detailed hereinabove.

Reference is now made to FIG. 7, which is a schematic illustration of system 120 for monitoring at least one electrical property of an organ of a subject, according to a preferred embodiment of the present invention. System 120 preferably comprises a radiofrequency generator 122, for generating an output radiofrequency signal. Generator 122 may be embodied as any radiofrequency generator, such as, but not limited to, radiofrequency generator 112 of system 110. System 120 further comprises a plurality of electrodes 125, which are connected to the skin of subject 121. Electrodes 125 transmit output radiofrequency signal 124, generated by generator 122 and sense input radiofrequency signal 126 originated from the organ of subject 121.

System 120 preferably comprises any of the components of apparatus 40 described above. According to a preferred embodiment of the present invention system 120 further comprises a detector 129 for detecting a voltage drop on a portion of the body of subject 121 defined by the positions of electrodes 125. In response to the detected voltage, detector 129 preferably generates a signal which is indicative of impedance of the respective portion of the body. In this embodiment, the stroke volume can be calculated using $(dX/dt)_{max}$, as further detailed hereinabove. Knowing the stroke volume, the cardiac output is calculated by multiplying the stroke volume by the heart rate of the subject. More preferably, detector 129 generates a signal which is indicative of a hemodynamic reactance, X.

The blood flow determination provided by system 120 may be used both for diagnostic and for treatment. Hence, according to a preferred embodiment of the present invention, system 120 may further comprise a pacemaker 144. In this embodiment, the data processor (not shown, see FIG. 4) is preferably programmed to electronically control pacemaker 144 in accordance with the calculated quantity. For example, in one embodiment, the data processor calculates the cardiac output and sends signals to pacemaker 144 which controls, substantially in real-time, the heart rate of subject 121, so as to improve the cardiac output.

Additionally or alternatively, system 120 may also comprise a cardiac assist device 148, preferably constructed and design for increasing the cardiac output. Cardiac assist devices are known in the art and typically comprise a reinforcing member which restricts an expansion of a portion of the heart tissue, so that the cardiac output is increased. In this embodiment, the data processor is preferably programmed to electronically control device 148 in accordance with the calculated cardiac output, so that both the determination and the improvement of the cardiac output are automatically performed by system 120.

According to a preferred embodiment of the present invention system 120 comprises a drug administrating device 146. Device 146 serves for administrating drugs to subject 121. In this embodiment, the data processor is preferably programmed to electronically control device 146, in accordance with the value of the calculated quantity. For example, if the calculated quantity is the brain intra luminal blood volume, then, depending on the value of the blood volume, the data processor sends signal to device 146 and thereby controls the amount and/or type of medications administered to subject 121.

It is to be understood that any number of electrodes of system 125 or connection configurations of electrodes 125 to subject 121 are not excluded from the present invention. Any type of electrode, in any combination, may be used, for measuring blood flow in any artery of the body, such as, but not limited to, the external carotid artery, the internal carotid artery, the ulnar artery, the radial artery, the brachial artery, the common iliac artery, the external iliac artery, the posterior tibial artery, the anterior tibial artery, the peroneal artery, the lateral plantar artery, the medial plantar artery and the deep plantar artery.

When system 120 is used together with other systems it is desired to minimize the area occupied by electrodes 125 so as not to interfere the operation of the other systems. For example, in intensive care units, the subjects are oftentimes connected to ECG leads, arterial line, central venous line, brain stem evoked response equipment, chest tubes, GI tube, intravenous and the like.

FIGS. 8a-e are schematic illustrations showing perspective (FIG. 8a), front (FIG. 8b), rear (FIG. 8c), side (FIG. 8d) and top (FIG. 8e) views of a sticker 141 which can be used for transmitting and sensing the radiofrequency signal, according to one embodiment of the present invention. The sticker comprises electrical contacts 145 being as fixed and predetermined distance therebetween, thus reducing any the effect of variable inter-electrode distance on the measurement. Two such contacts 145a and 145b are shown in FIG. 8b, but any number of contacts can be employed, with the provision that there are at least two contacts. The sticker can be connected to system 120 via a connector 143. Connector 143 is optionally foldable to facilitate packaging and storage of sticker 141. In various exemplary embodiments of the invention connector 143 includes two conductive members 149a and 149b devoid of electrical communication therebetween. Each of electrical contacts 145a and 145b is in electrical communication with one conductive member of connector 143 via a different internal conducting line 147a and 147b. Thus, in the present embodiments, sticker can be connected to system 120 using a single line, because connector 143 interfaces communication for both contacts.

Figure 8F:
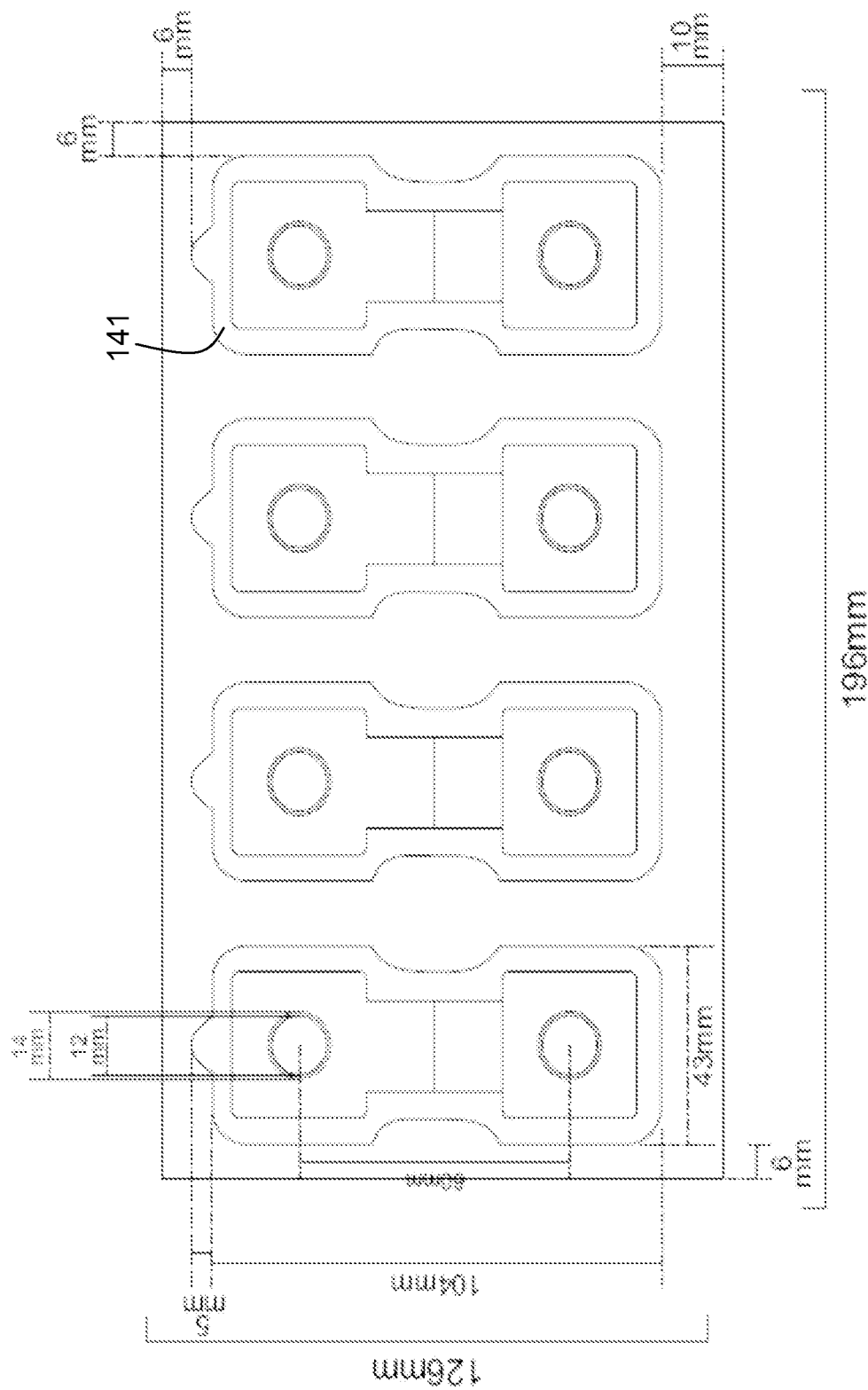
FIG. 8f is a schematic illustration of a package of several stickers according to an embodiment of the present invention.

FIG. 8f is a schematic illustration of a package of several stickers (four such stickers are shown in the exemplary illustration of FIG. 8O, where each sticker can be similar to sticker 141 described above. Also shown in FIG. 8f are exemplary dimensions and distances of the package and the individual stickers.

Following are technical preferred values which may be used for selective steps and parts of the embodiments described above.

The output radiofrequency signal is preferably from about 10 KHz to about 200 KHz in frequency and from about 10 mV to about 200 mV in magnitude; the input radiofrequency signal is preferably about 75 KHz in frequency and about 20 mV in magnitude; a typical impedance which can be measured by the present embodiments is from about 5 Ohms to about 75 Ohms; the resulting signal-to-noise ratio of the present embodiments is at least 40 dB; low pass filter 134 is preferably characterized by a cutoff frequency of about 35 Hz and digitizer 138 preferably samples the signal at a rate of about 500-1000 samples per second.

As used herein, the singular form "a", "an" and "the" include plural references unless the context clearly dictates otherwise. For example, the term "a compound" or "at least one compound" may include a plurality of compounds, including mixtures thereof.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Prototype System

A prototype of a system for measuring blood flow in an organ of a subject according to the above description was constructed.

The prototype system includes:

(a) a self made radiofrequency generator generating an output radiofrequency signal, 70 Khz in frequency and 20 mV in magnitude;

(b) a plurality of electrodes, as described in FIGS. 8a-d; and (c) a double balanced mixer, purchased from Mini-Circuits, used for providing a radiofrequency sum and a radiofrequency difference, as detailed above.

The prototype system further includes electronic circuitry formed in a printed circuit board. Several electronic circuitries were designed and manufactured, so as to investigate the correlation between the qualities of the results, the design of the electronic circuitry and the number of electrodes. The various electronic circuitries are schematically illustrated in FIGS. 9a-d.

Figure 9A:
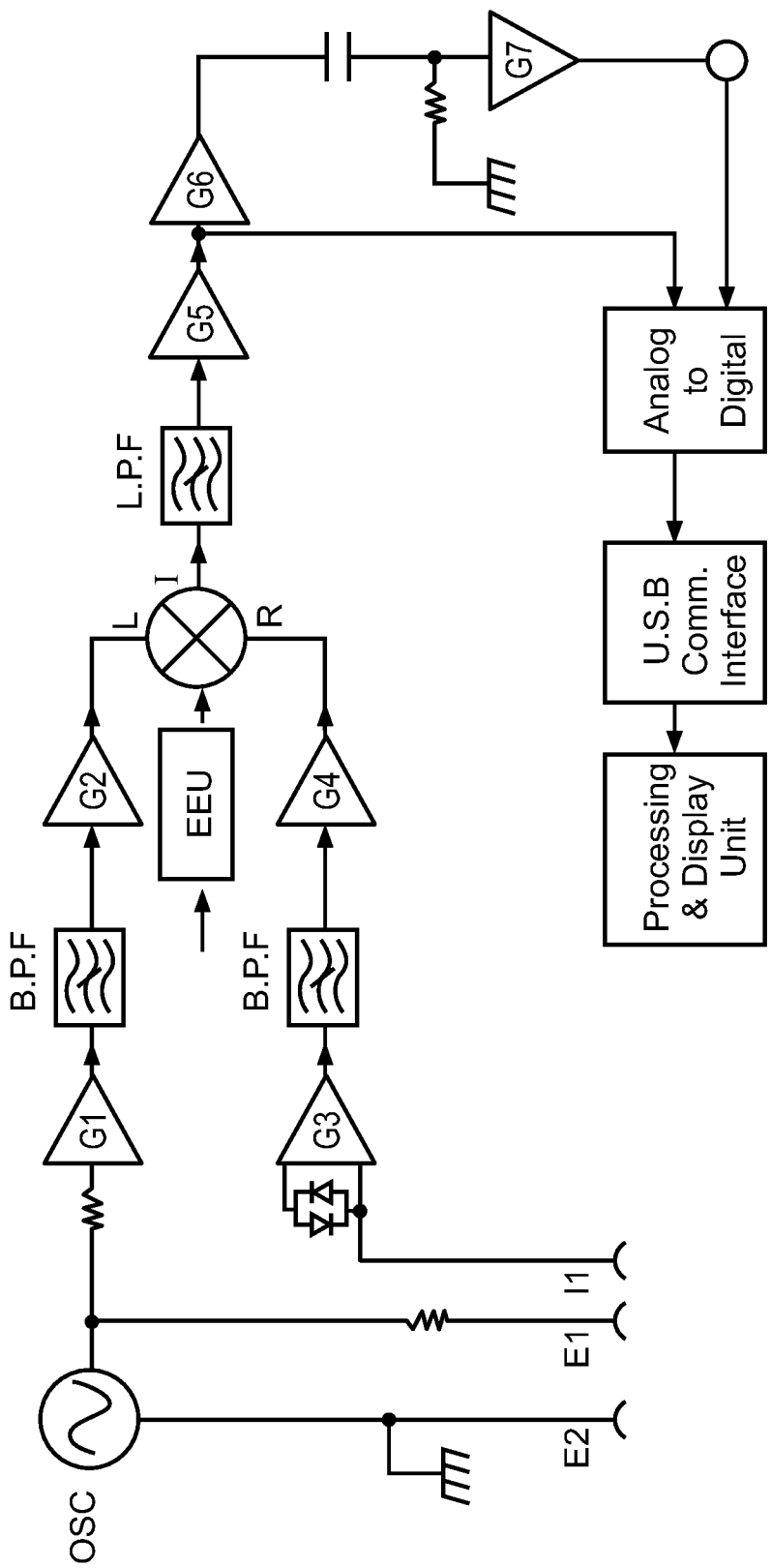
FIGS. 9a-d are schematic illustrations of various electronic circuitries, according to exemplary embodiments of the present invention.

FIG. 9a shows a block diagram of electronic circuitry to be used with three electrodes. The electrodes leads are designated in FIG. 9a by $E_1$, $E_2$ and $I_1$, where the output radiofrequency signal, generated by the radiofrequency generator (designated OSC), is outputted through $E_1$ and $E_2$ and the input radiofrequency signal, as measured of the body is inputted through $I_1$.

The input signal is channeled through a differential amplifier $G_1$, a band pass filter BPF and a differential amplifier $G_2$. The input signal is channeled through a differential amplifier $G_3$, a band pass filter BPF and an envelope elimination unit EEU. The EEU eliminates the amplitude modulation from the input signal. Both input and output signals are mixed by mixer DMB, to form, as stated, a frequency sum and a frequency difference. A low pass filter LPF filters out the frequency sum and the resulting signal (carrying the frequency difference) is further amplified by additional differential amplifiers $G_5$, $G_6$ and $G_7$. Once amplified, the signal is digitized by an analog to digital digitizer and passed, via a USB communication interface to a processing and display unit. The processing unit includes a dynamically variable filter according to various exemplary embodiments of the present invention.

Figure 9B:
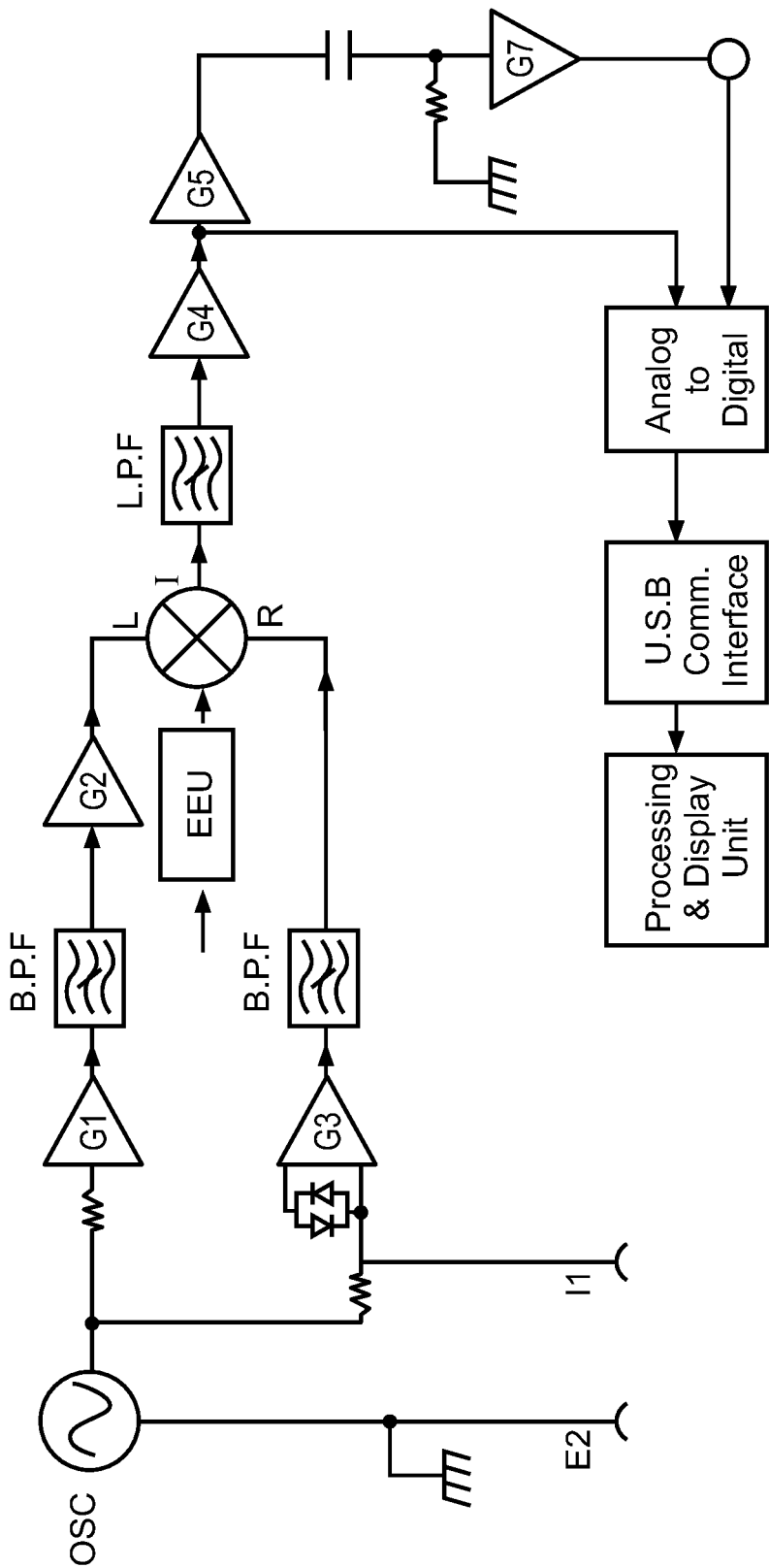

FIG. 9b shows a block diagram of electronic circuitry to be used with two electrodes of brain intra-luminal blood volume measurements. As there are only two electrodes $E_2$ and $I_1$ are combined to a single lead $I_1$.

The output signal is channeled through a differential amplifier $G_1$, a band pass filter BPF and a differential amplifier $G_2$. The input signal is channeled through a differential amplifier $G_2$, a band pass filter BPF and an envelope elimination unit EEU which eliminates the amplitude modulation from the input signal. Both input and output signal are mixed by mixer DMB, to form the frequency sum and difference. The low pass filter LPF filters out the frequency sum and the resulting signal is further amplified by additional differential amplifiers $G_4$, $G_5$ and $G_6$. As in the case of three electrodes, the signal is digitized by an analog to digital digitizer and passed, via a USB communication interface to a processing and display unit.

Figure 9C:
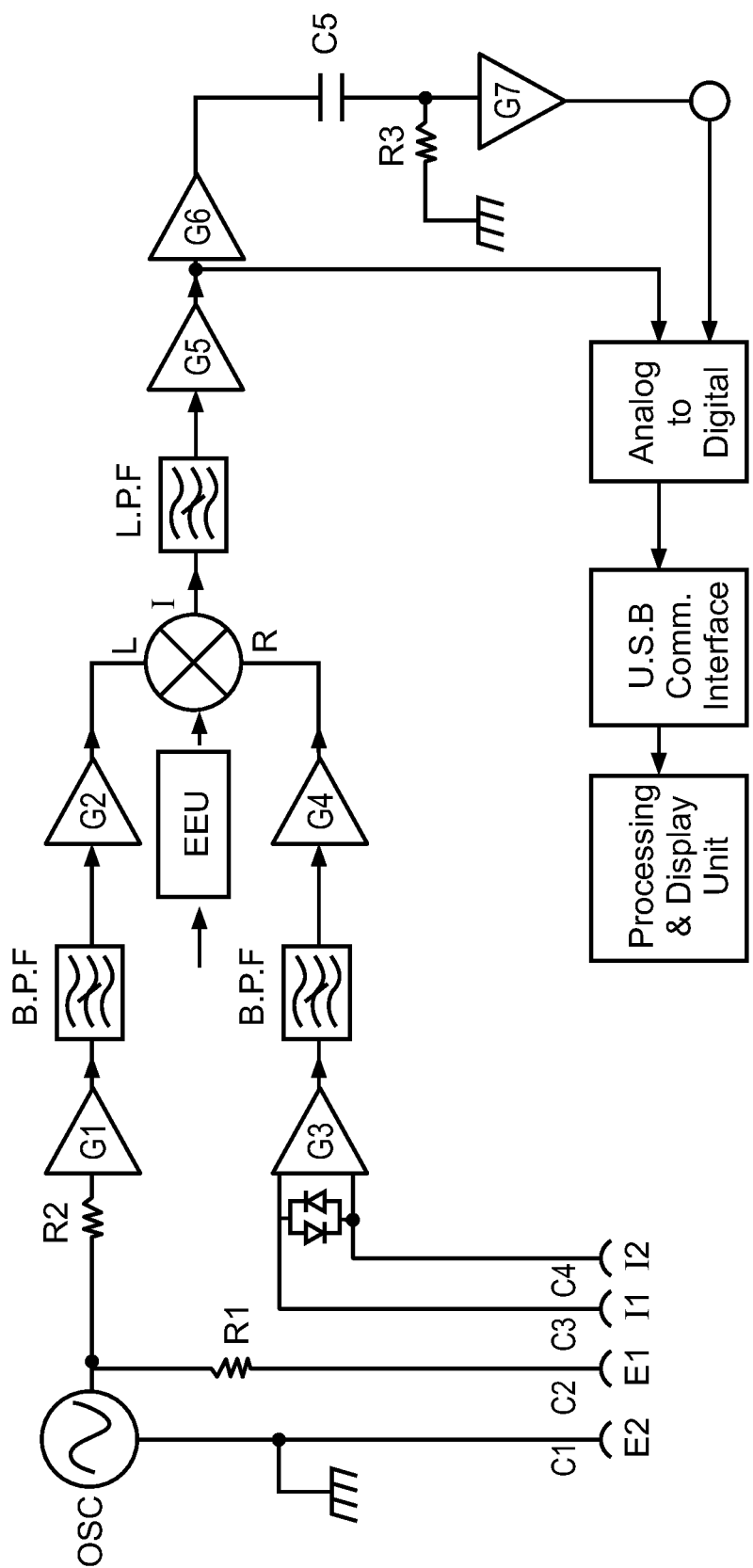

FIG. 9c shows a block diagram of electronic circuitry to be used with four electrodes. The four leads, designated $E_1$, $E_2$, $I_1$ and $I_2$, where the output radiofrequency signal, generated by radiofrequency generator OSC, is outputted through $E_1$ and $E_2$ and the input radiofrequency signal, as measured of the body are inputted through $I_1$ and $I_2$. In addition, the four leads, $E_1$, $E_2$, $I_1$ and $I_2$ are connected to the body through capacitors designated $C_1$, $C_2$, $C_3$ and $C_4$.

The principles of the circuitry of FIG. 9c are similar to the principles of the circuitry of FIG. 9a with three electrodes. The advantage of the circuitry of FIG. 9c is that by using both input leads $I_1$ and $I_2$ (as opposed to one input lead $I_1$ of FIG. 9a), effects of impedance differences between the electrodes and the body can be minimized. Specifically, the influence of the voltage drop $I_1$ and $I_2$ is controlled by the characteristic impedance of the differential amplifier $G_3$, which is selected to be sufficiently large so that any impedance changes due to the contact between the body and the electrode is negligible, compared to the impedance of $G_3$.

Figure 9D:
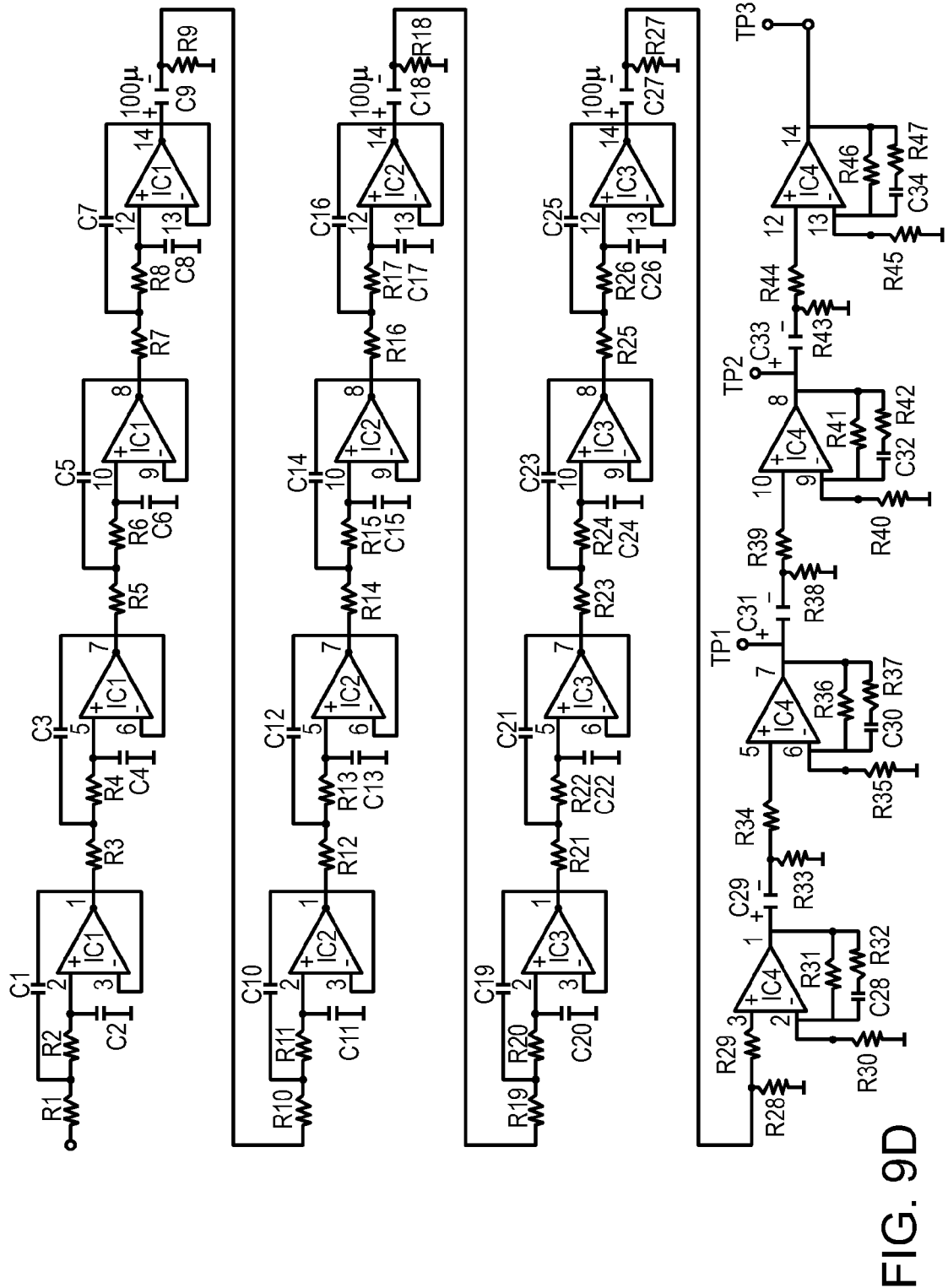

FIG. 9d shows a block diagram of the analog amplification circuit, which was used to amplify the radiofrequency signal after the low pass filtering in which the radiofrequency sum was filtered out.

Example 2

Clinical Trials

The prototype system described in Example 1 was tested on human volunteers. The present Example includes a representative collection of trials performed on four of the volunteers.

Methods

Each subject was connected to four electrodes of the prototype system. Two electrodes served for input/output radiofrequency signals and two served as ECG leads.

A radiofrequency signal pertaining to hemodynamic reactance was sampled at a sampling rate of 500 samples per second during continuous time intervals of 8 seconds. The signal was filtered by an analog low pass filter of 9 Hz.

An ECG signal was sampled at the same rate (500 samples per seconds) and filtered using an analog filter of 250 Hz.

In all the trials, the signals acquired from each subject were filtered using two types of digital filters: a fixed filter with a lower bound of 0.9 Hz and an upper bound of 6 Hz, and a dynamically variable filter in which the frequency bounds were varied in response to changes in the heart rate of the respective subject. To this end, the linear dependence as illustrated in FIGS. 2a-b was used.

Results

FIGS. 10a-e show snapshots of the display of the prototype system obtained during a trial in which the electrodes of the system were connected to subject No. 1. Signals were acquired while the subject was stable (heart rate of 95 bpm).

Figure 10A:
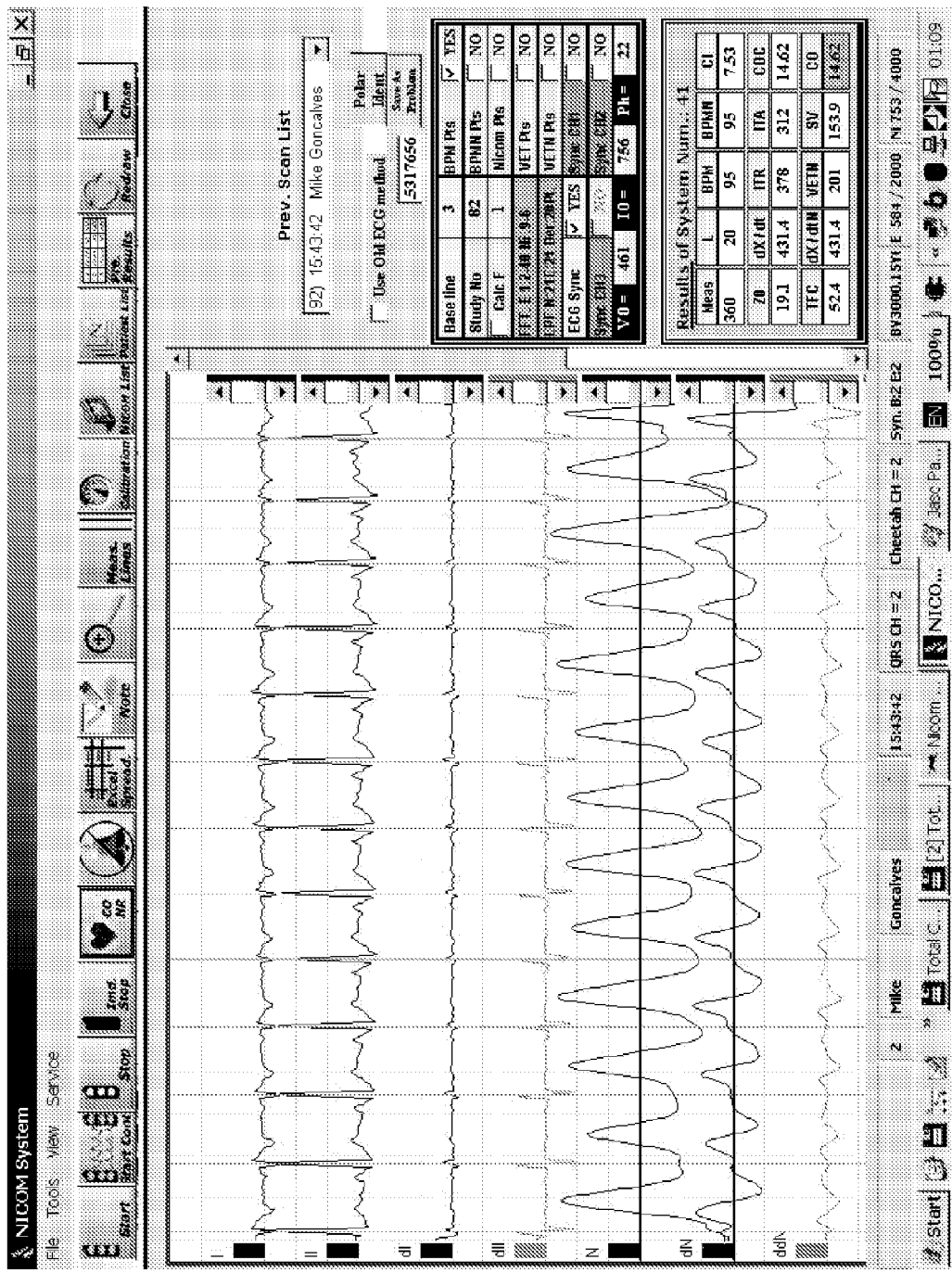
FIGS. 10a-10e, 11a-11e, 12a-12e, 13a-13e, 14a-14e, 15a-15e, 16a-16g and 17a-17g show snapshots of the display of a prototype system, manufactured and configured according to various exemplary embodiments of the present invention.
Figure 10B:
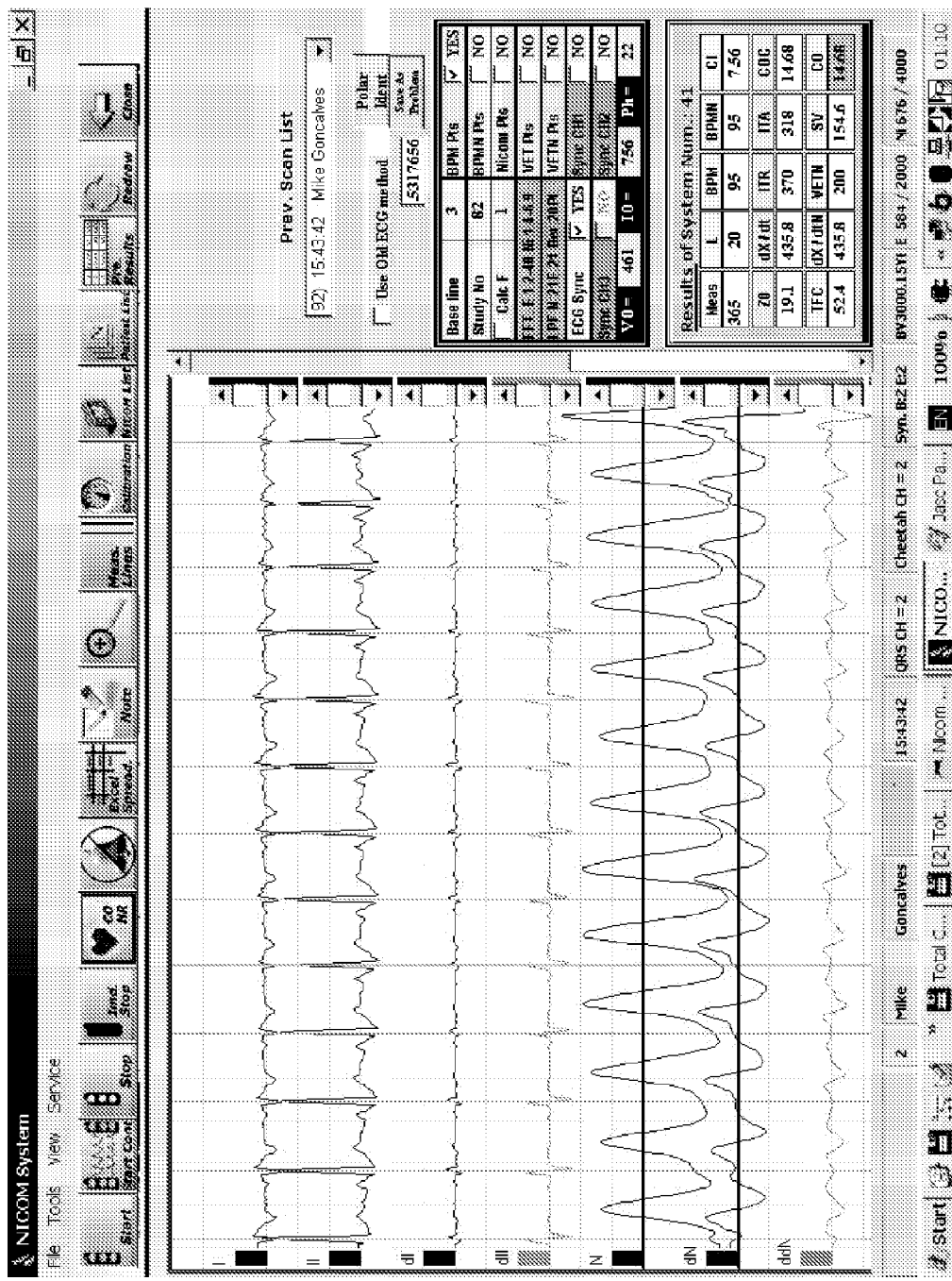

FIGS. 10a-b show results obtained using a fixed filter (FIG. 10a) and dynamically variable filter (FIG. 10b). In each of FIGS. 10a-b, there are seven curves, designated, from top to bottom, I, II, dI, dII, N, dN and ddN. The four top curves (I, II, dI and dII) are ECG signals (leads I and II) and derivatives thereof (dI and dII, respectively). The three lowermost curves (N, dN and ddN) correspond to a hemodynamic reactance (N), its first time-derivative (dN) and second time-derivative (ddN). The right pane of FIG. 10a show various calculated values, such as heart rate (BPM), cardiac output (CO), stroke volume (SV), ventricular ejection time (VETM), and the like.

Figure 10C:
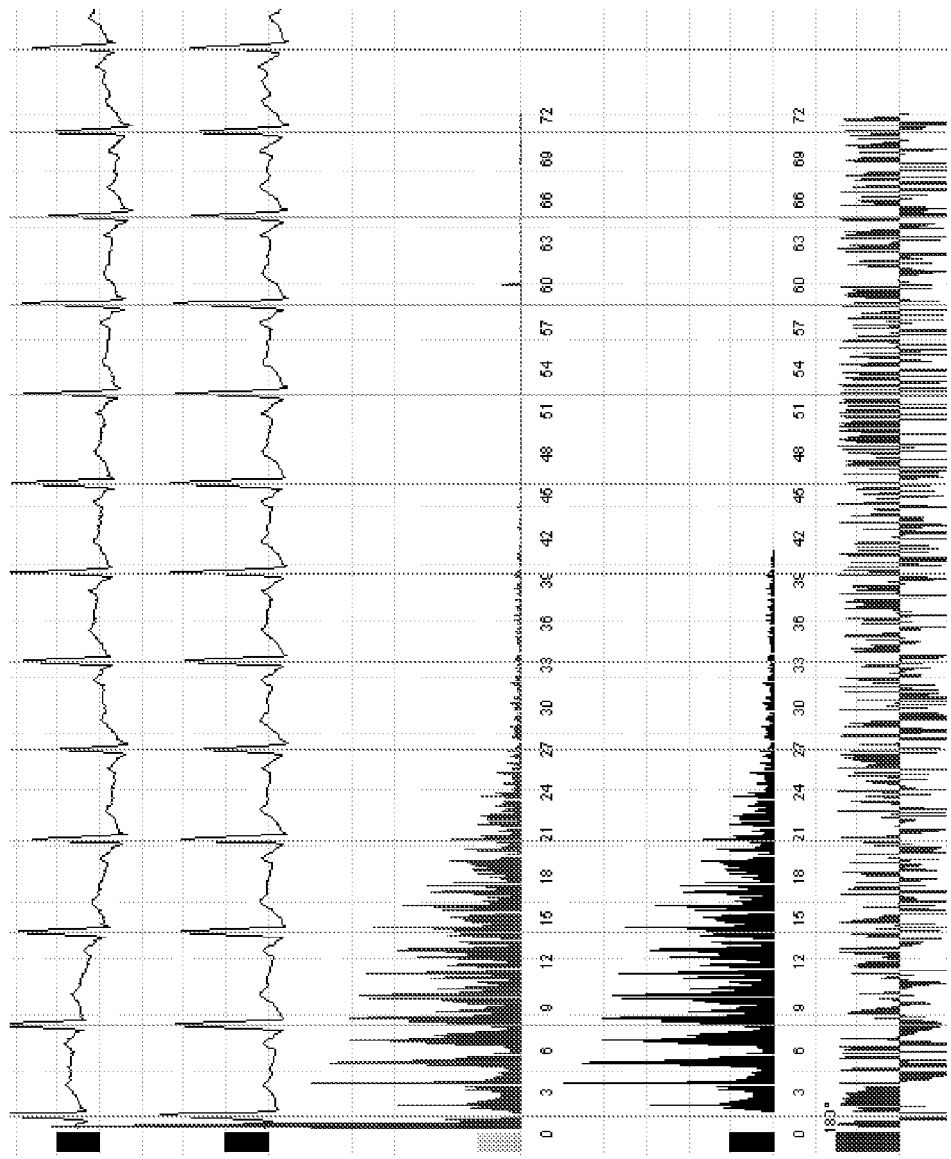
Figure 10D:
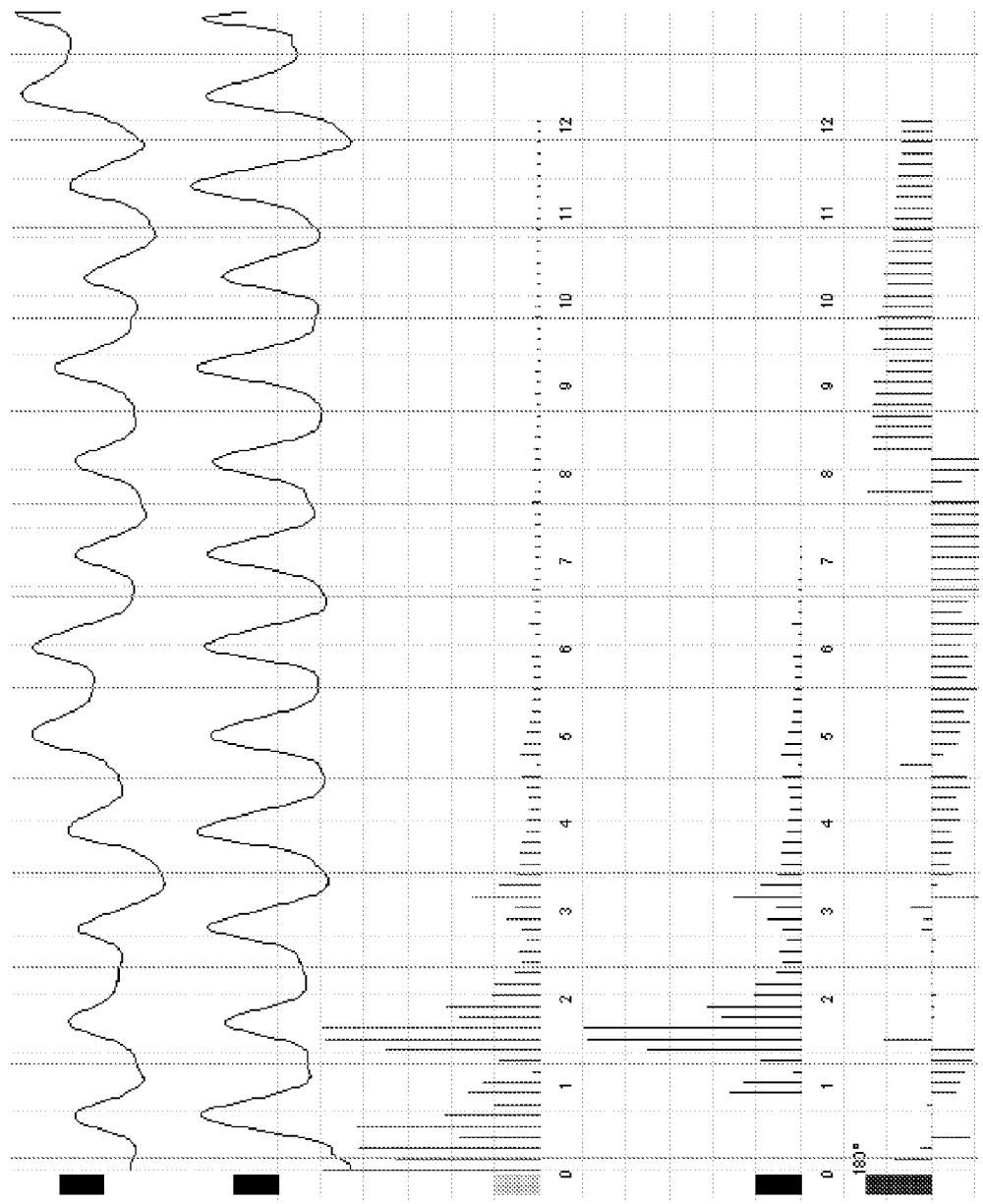

FIGS. 10c-d demonstrate the data analysis performed to provide the results presented in FIGS. 10a-b. FIG. 10c demonstrates application of the fixed filter on the ECG signal, FIG. 10d demonstrates the application of the fixed on the hemodynamic reactance signal, and FIG. 10e demonstrates the application of the dynamically variable filter on the hemodynamic reactance signal. In each of FIGS. 10c-d there are five graphical representations, corresponding to, from top to bottom: (i) the respective signal before filtering, (ii) the respective signal after filtering, (iii) the spectrum (Fourier decomposition) of the respective signal before filtering, (iv) the spectrum of the respective signal after filtering and (v) phase shift data. The lower and upper frequency bounds of the filter for the ECG signal were 1.2 Hz and 40 Hz, respectively; the lower and upper frequency bounds of the fixed filter for the hemodynamic reactance signal were 0.9 Hz and 6 Hz, respectively; and the lower and upper frequency bounds of the dynamically variable filter for the hemodynamic reactance signal were 1.4 Hz and 6.9 Hz, respectively.

Figure 10E:
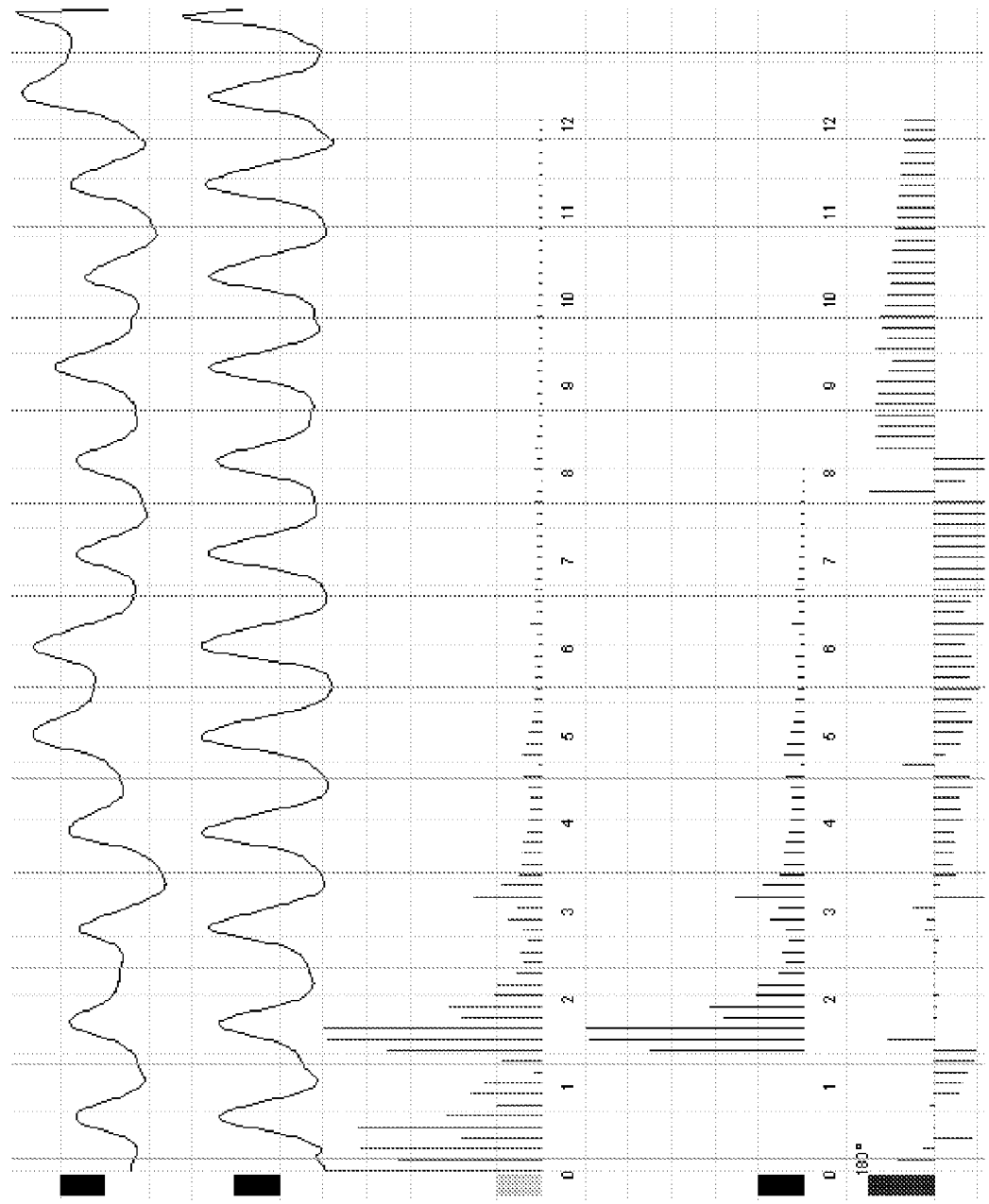
Figure 11A:
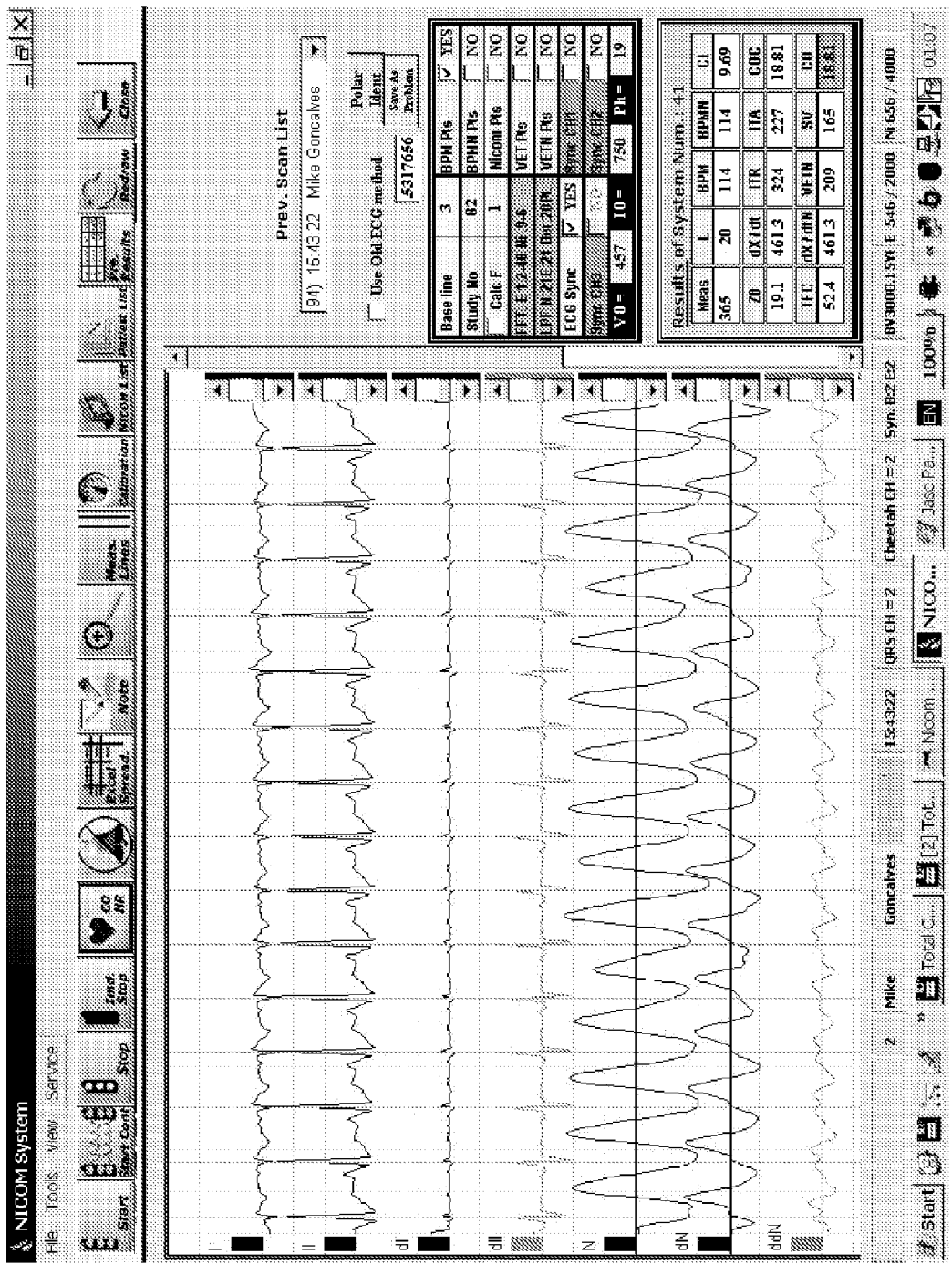
Figure 11B:
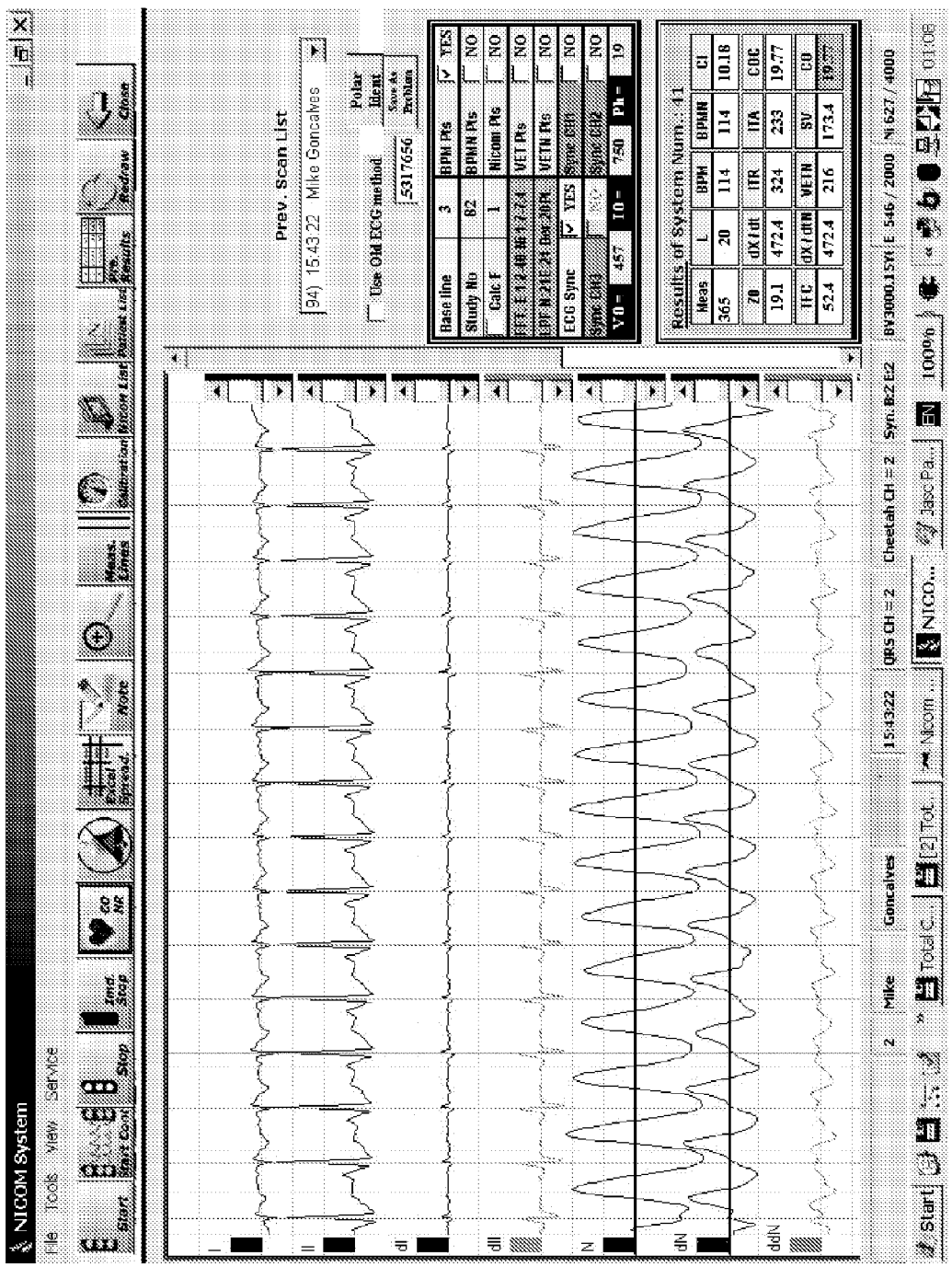
Figure 11C:
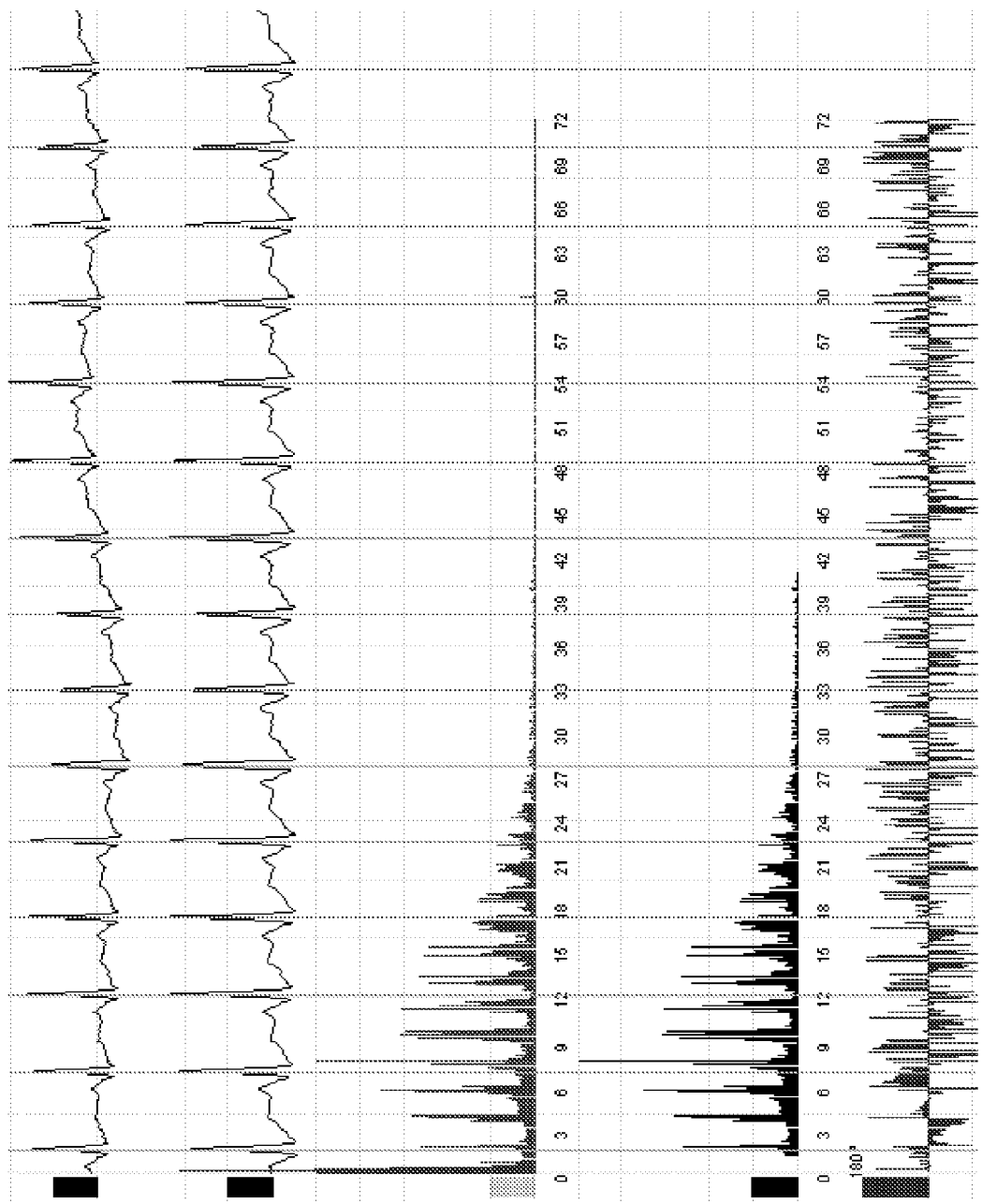
Figure 11D:
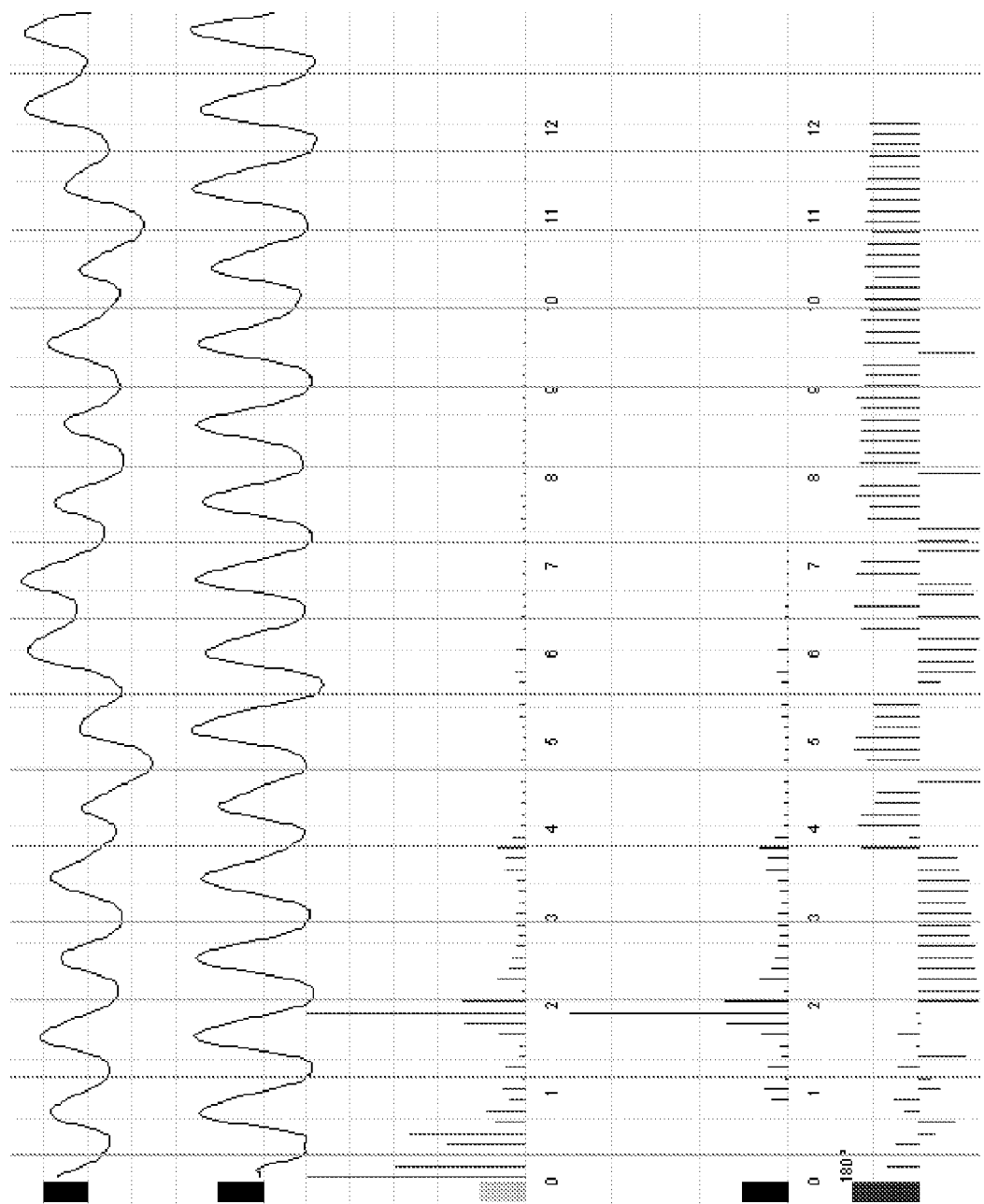
Figure 11E:
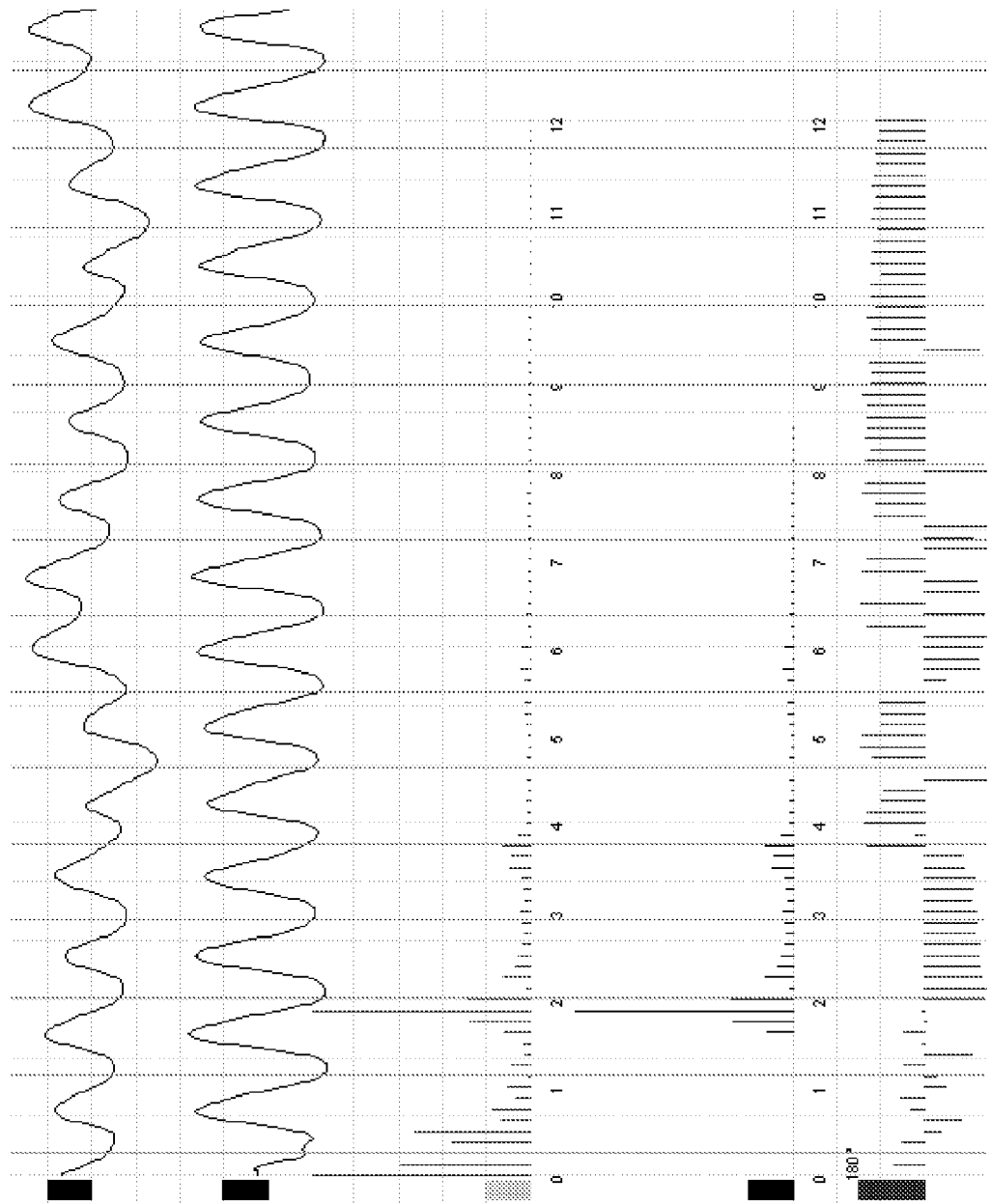
Figure 12A:
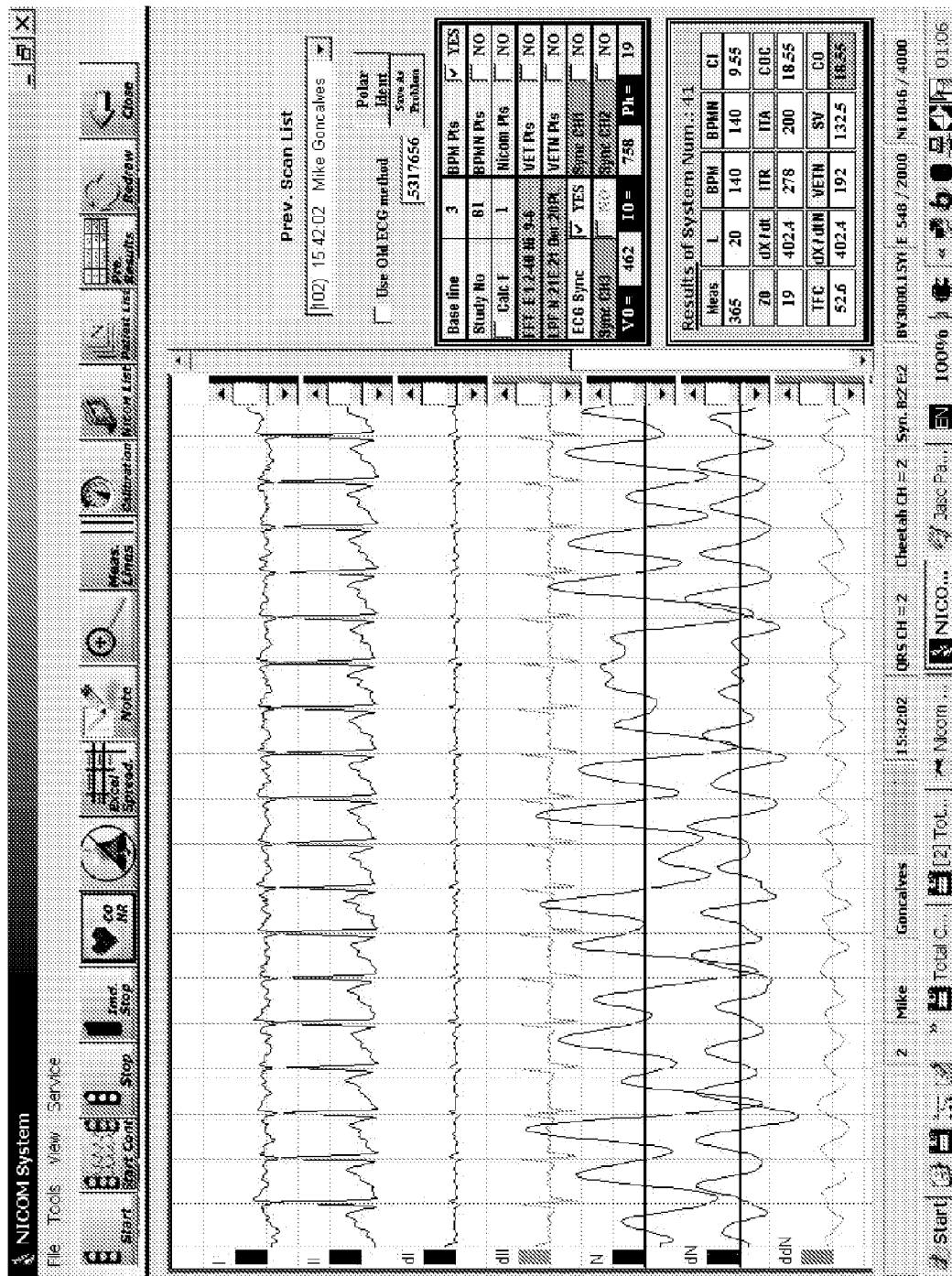
Figure 12B:
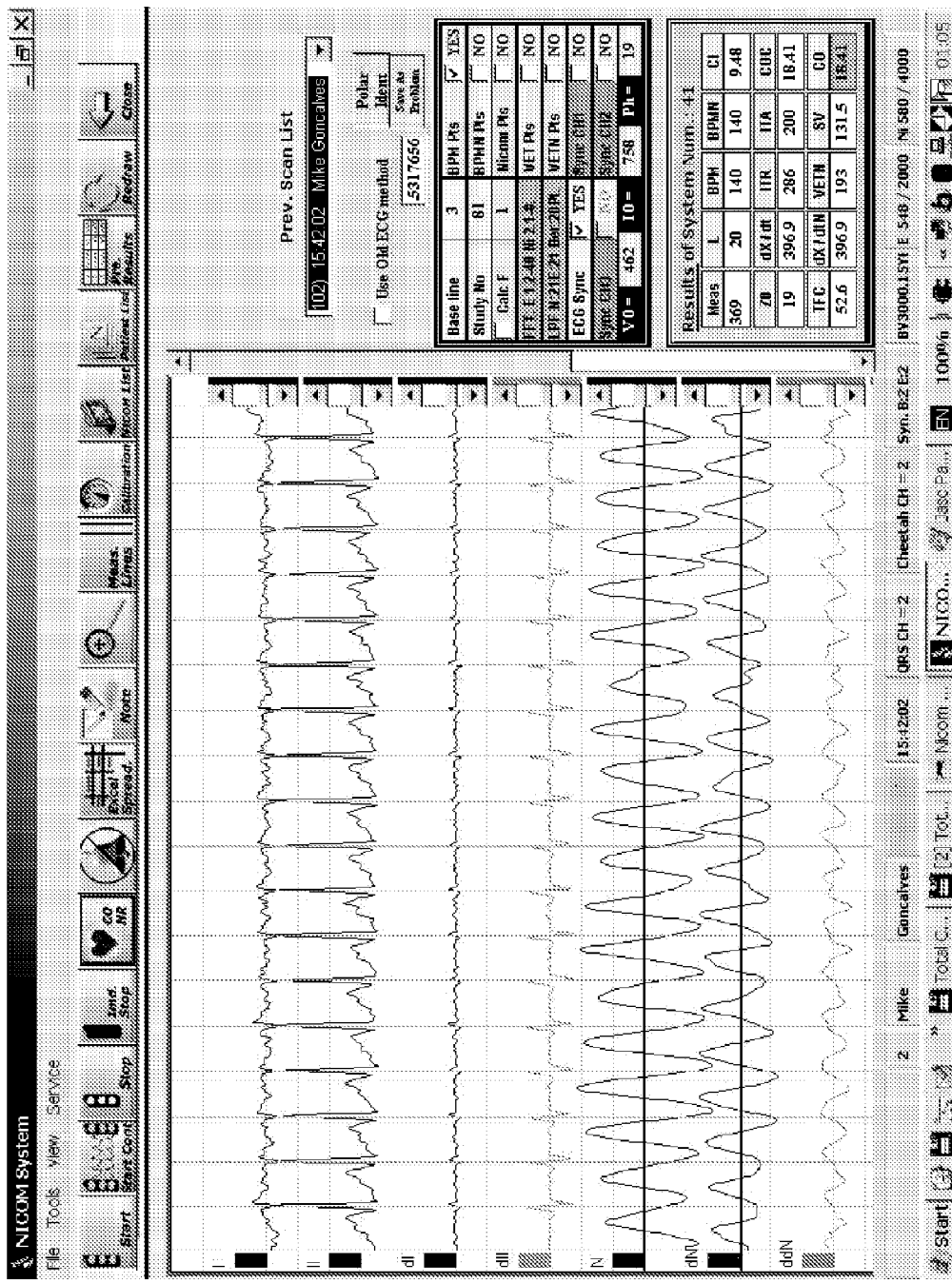
Figure 12C:
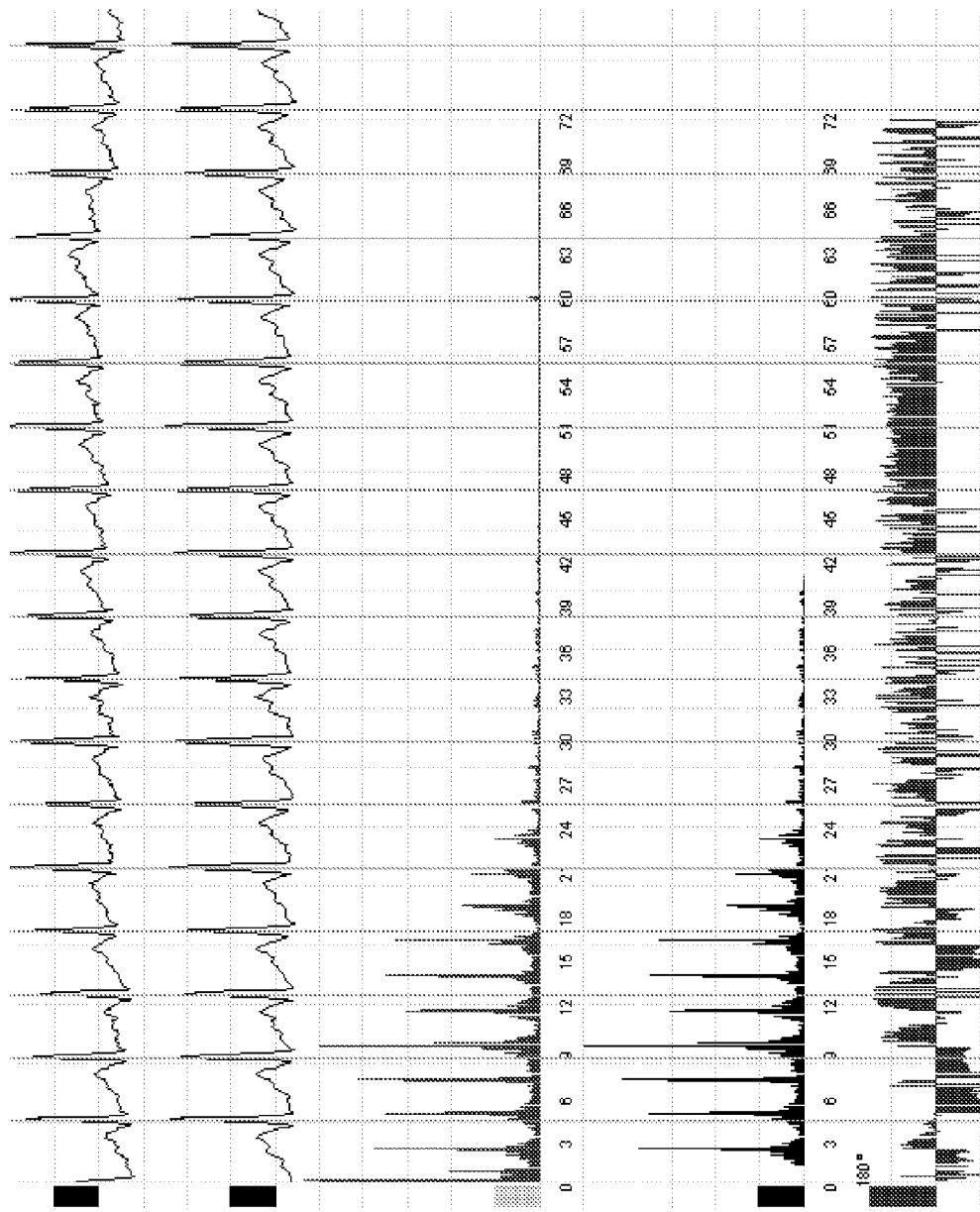
Figure 12D:
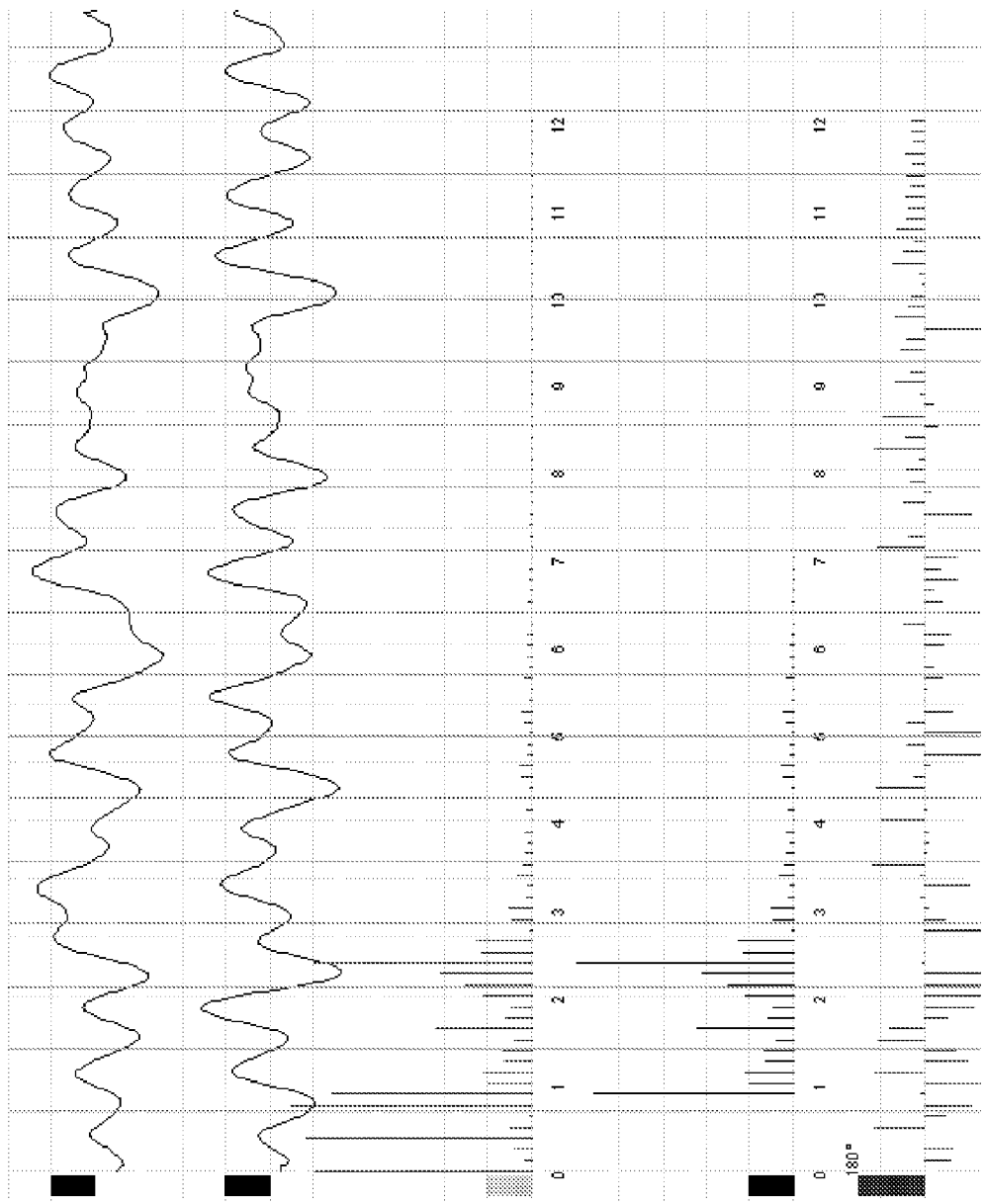
Figure 12E:
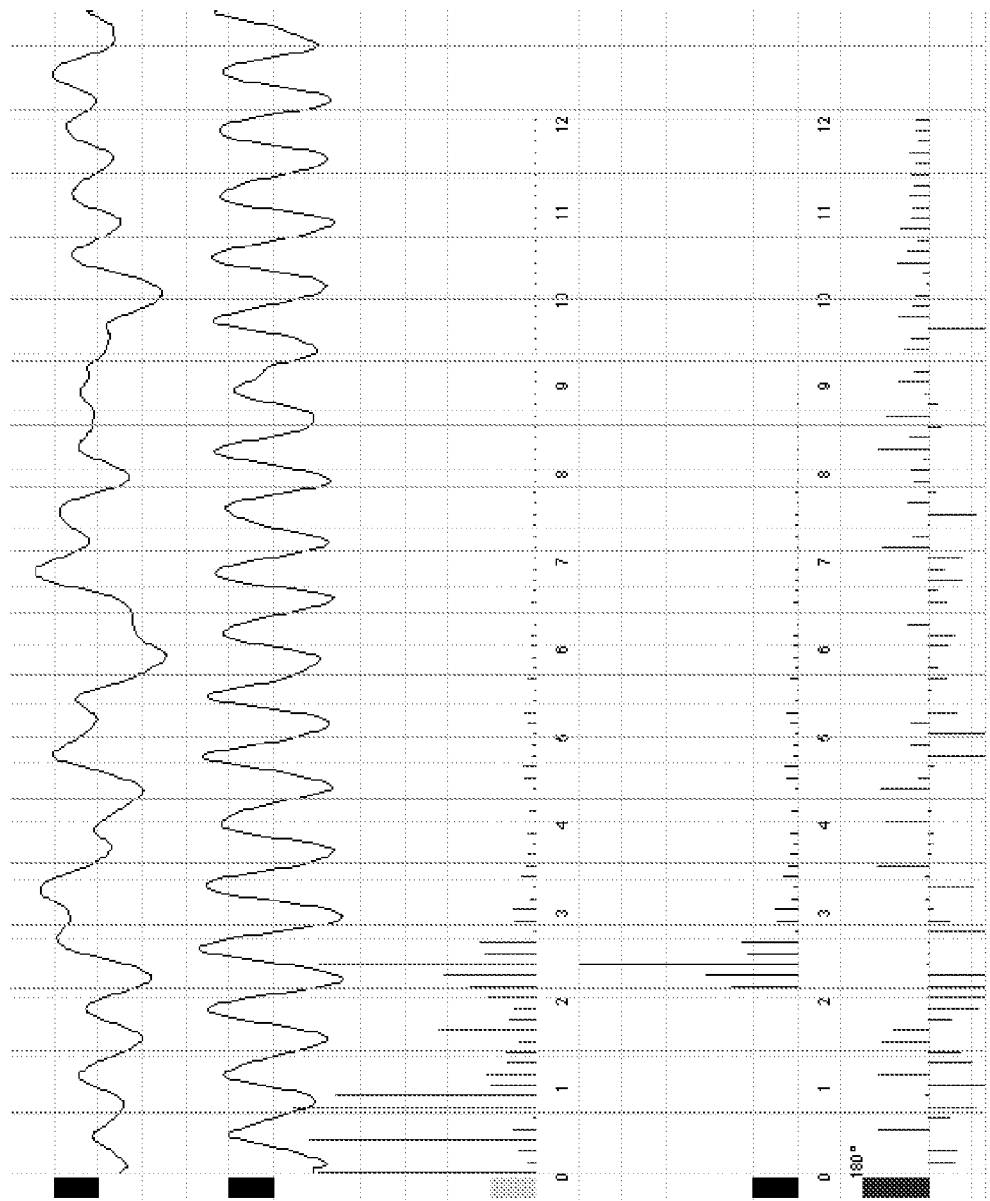
Figure 13A:
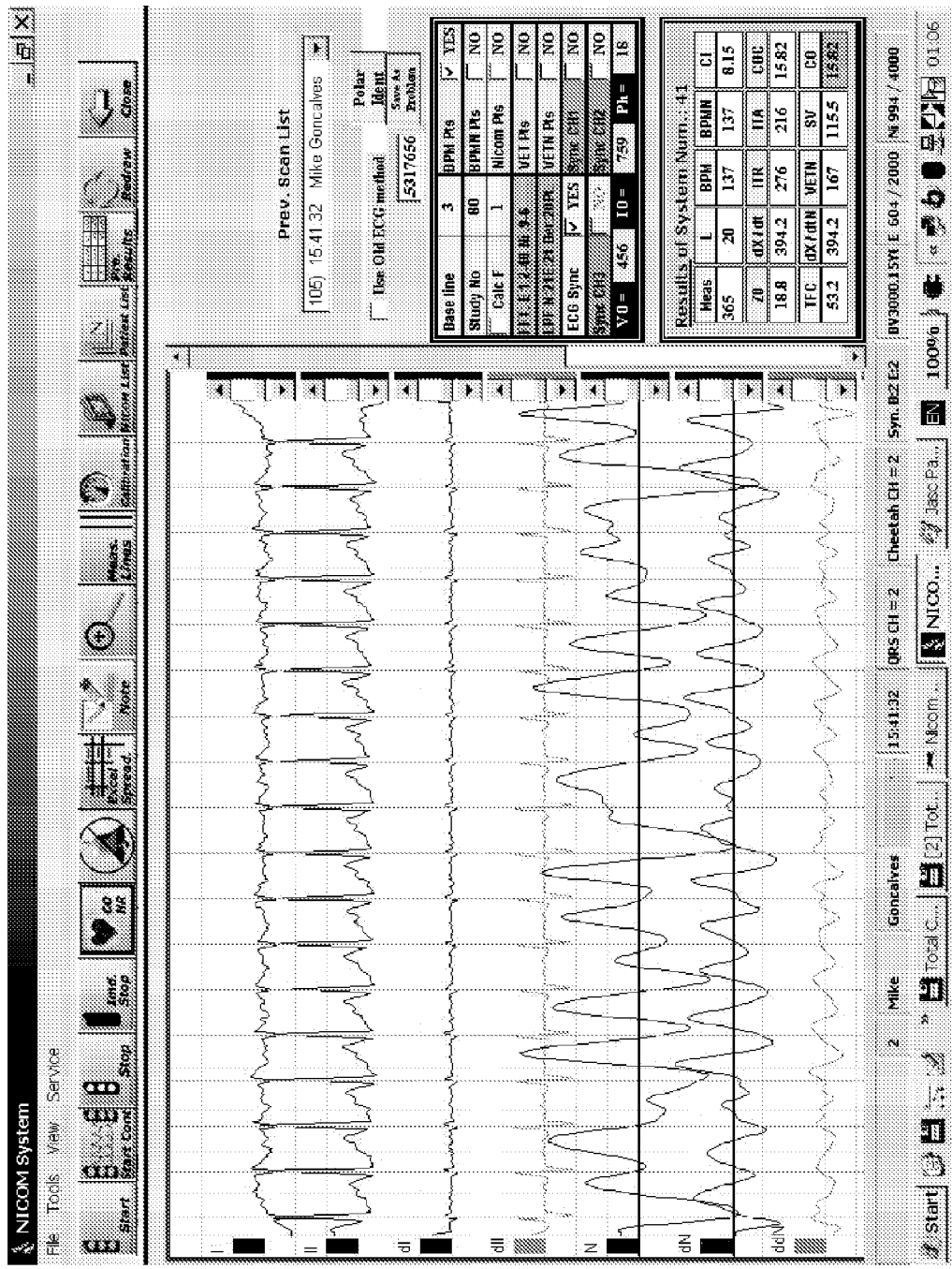
Figure 13B:
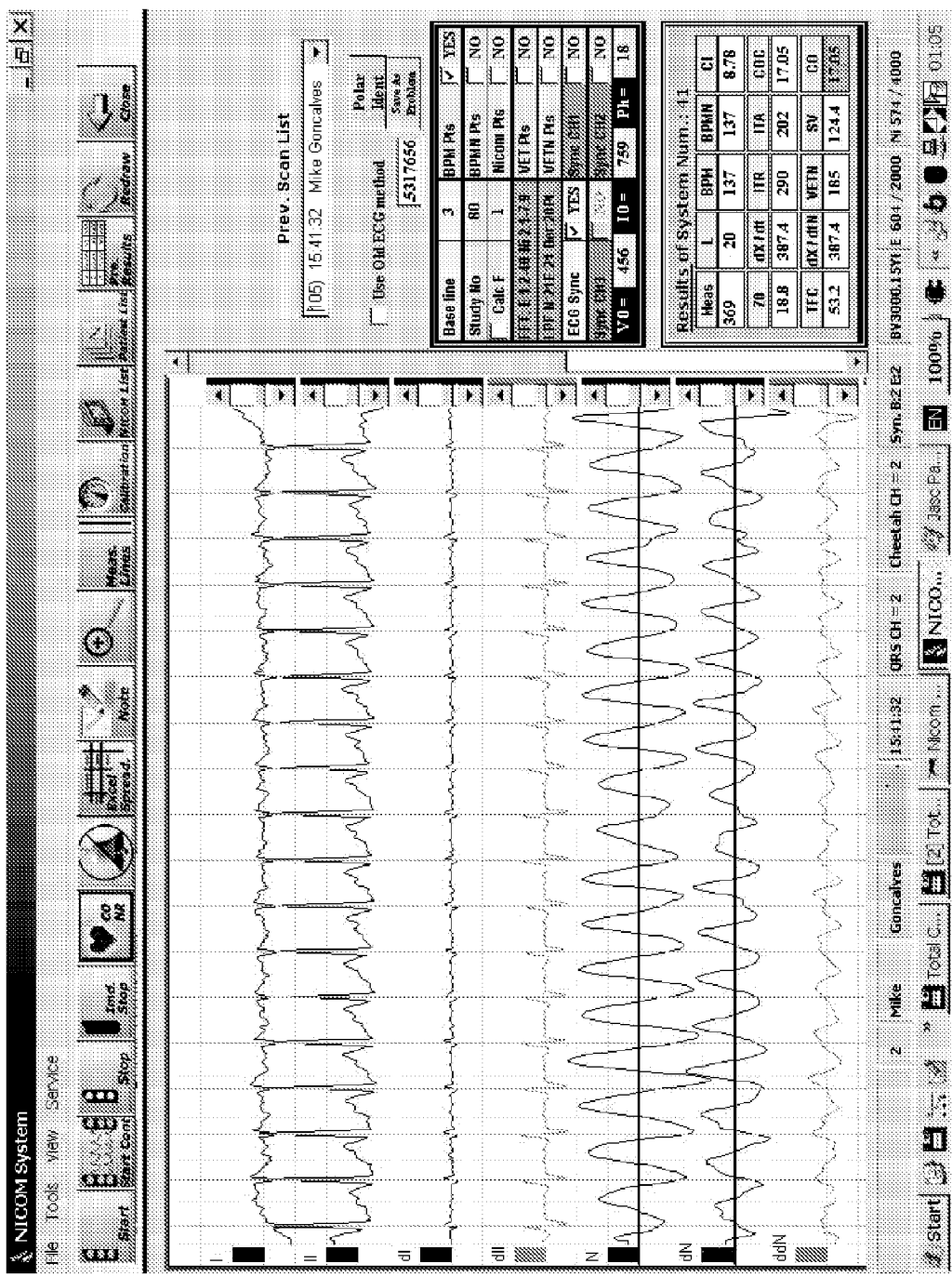
Figure 13C:
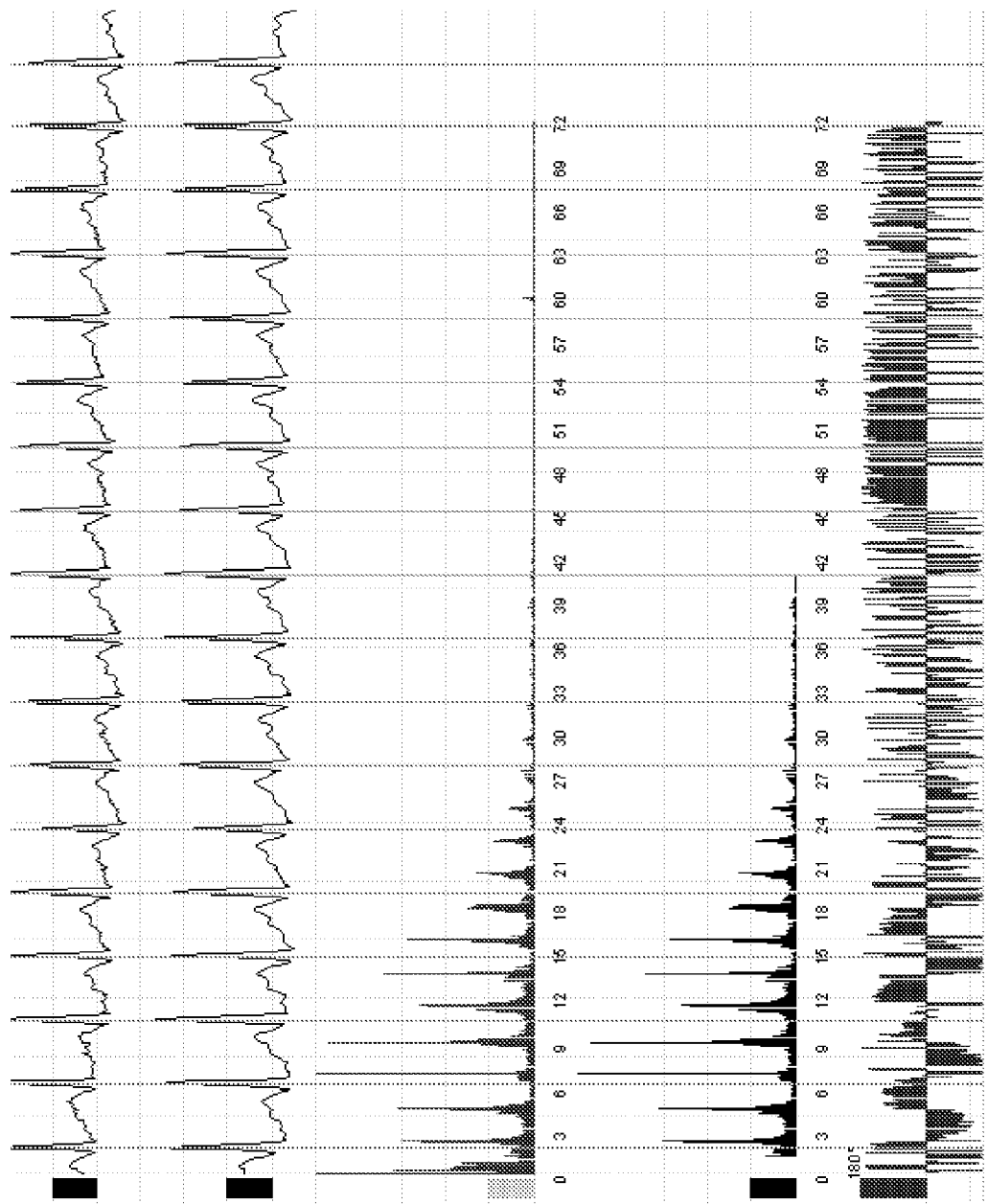
Figure 13D:
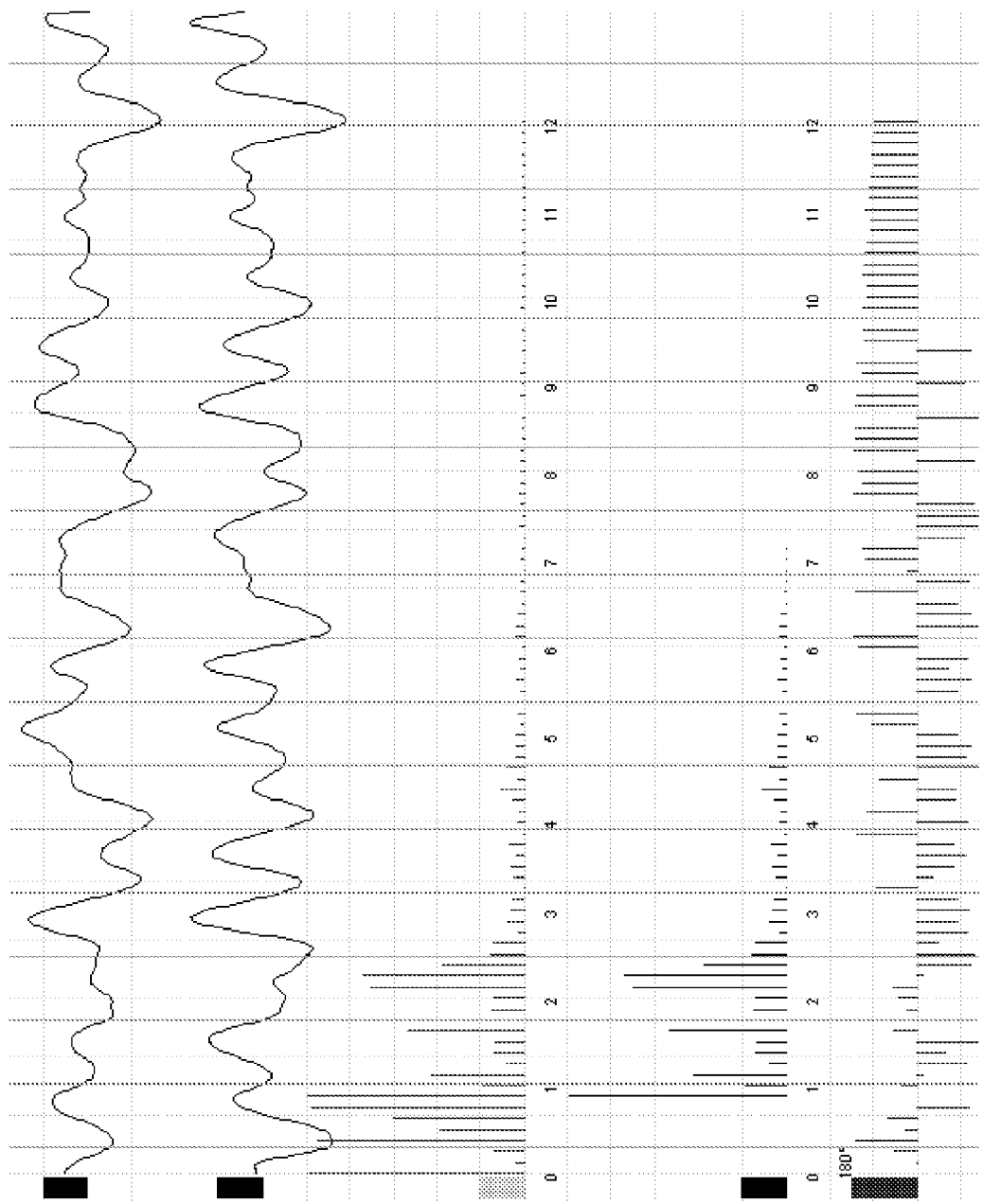
Figure 13E:
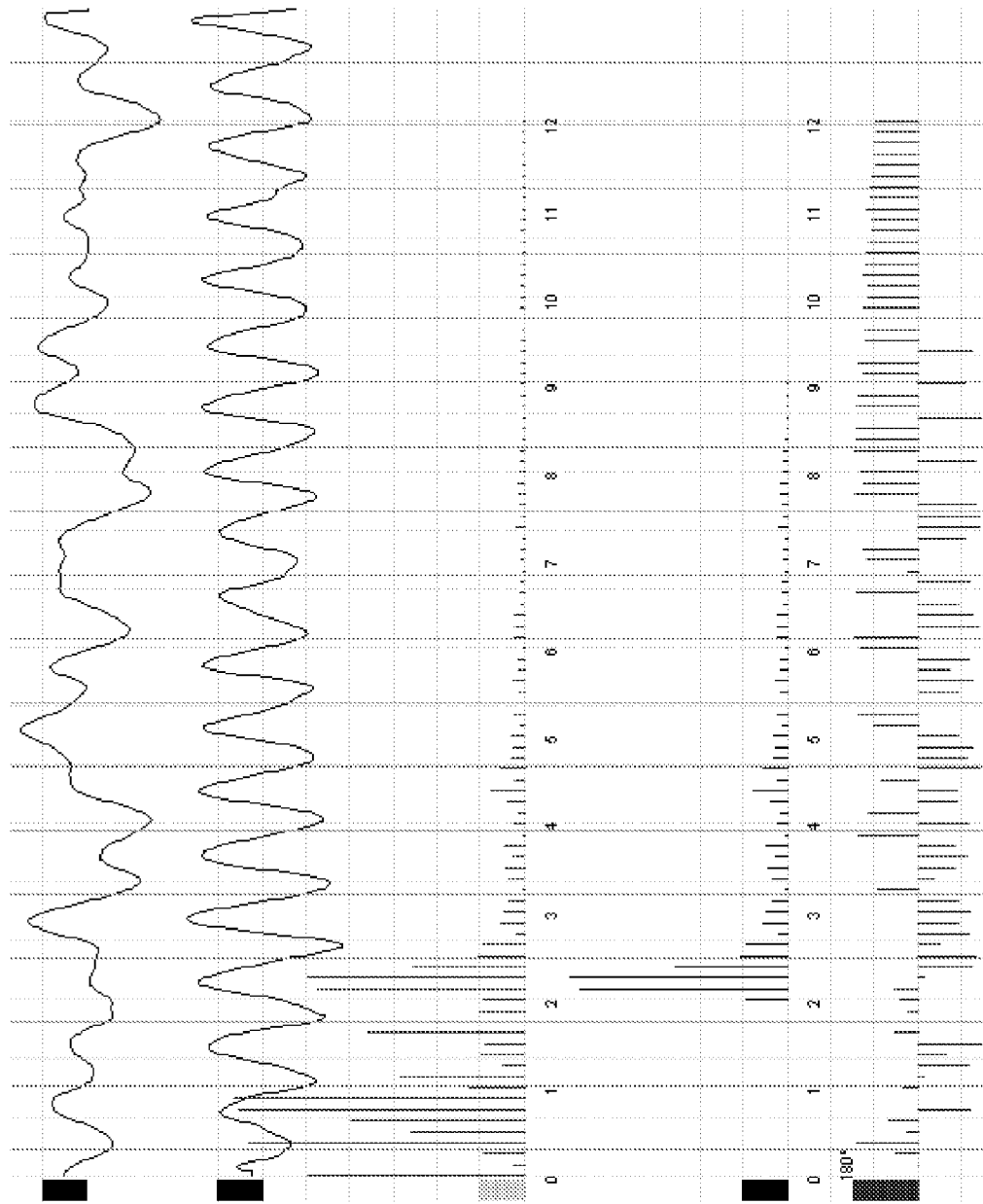
Figure 14A:
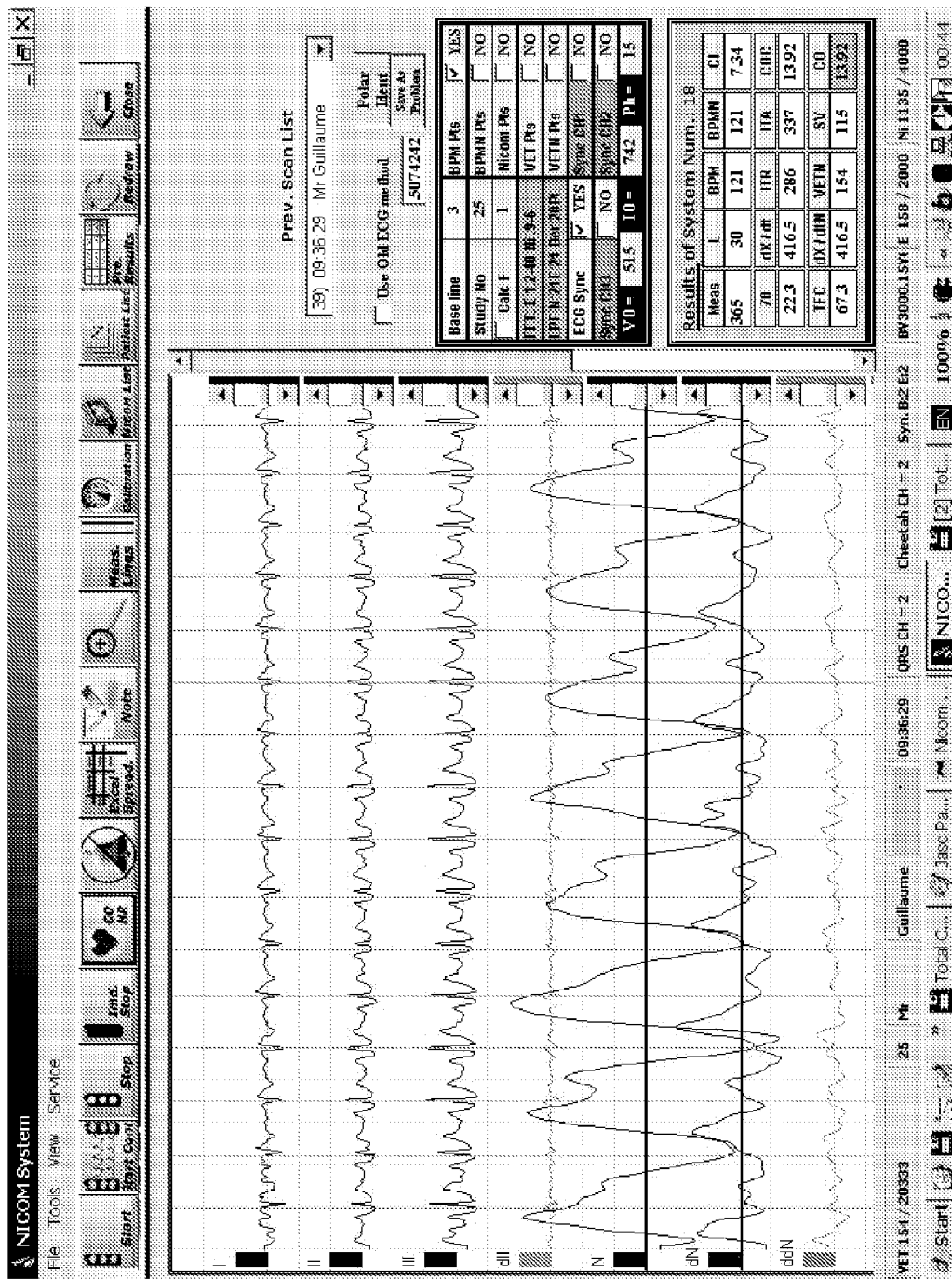
Figure 14B:
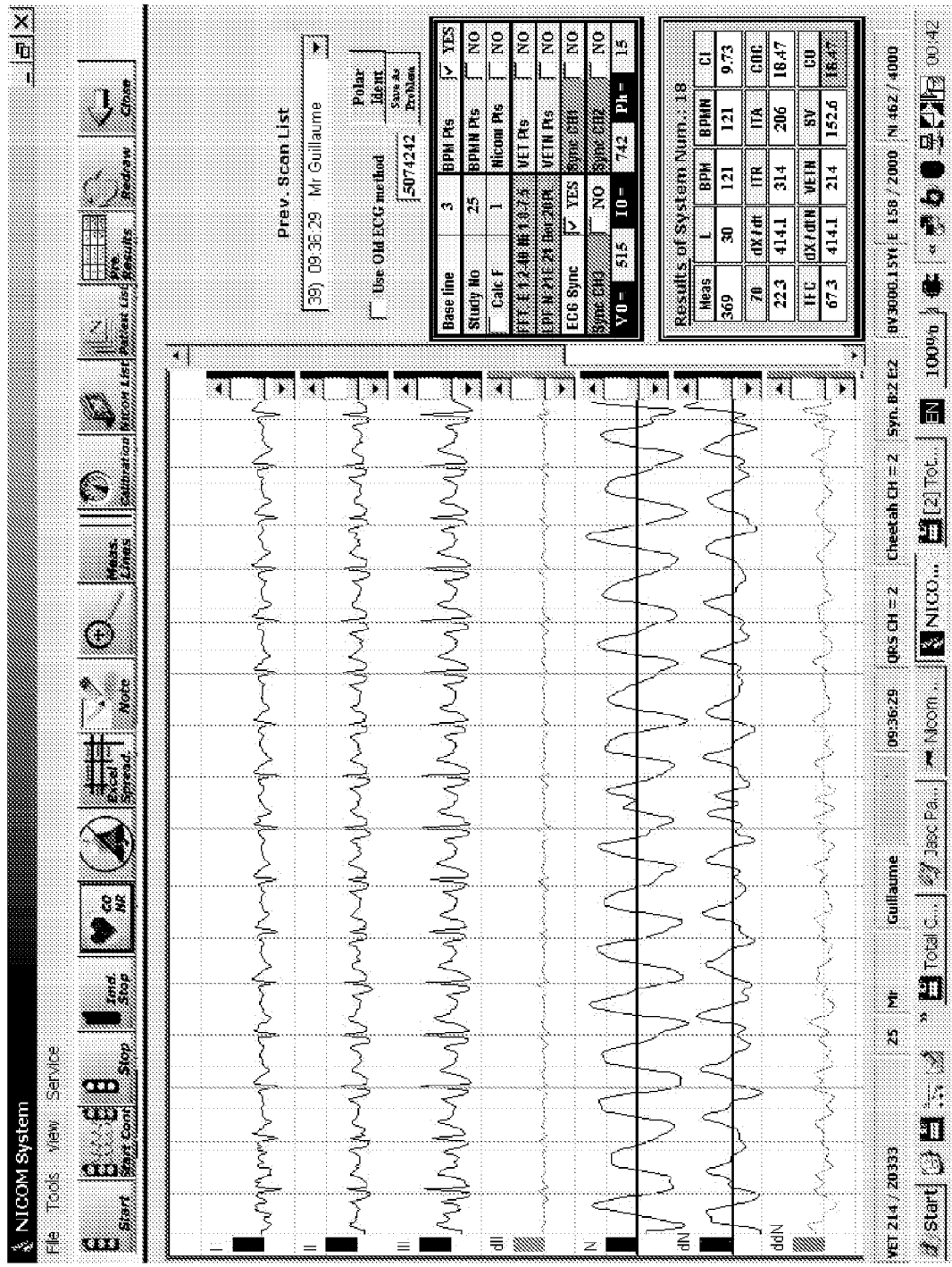
Figure 14C:
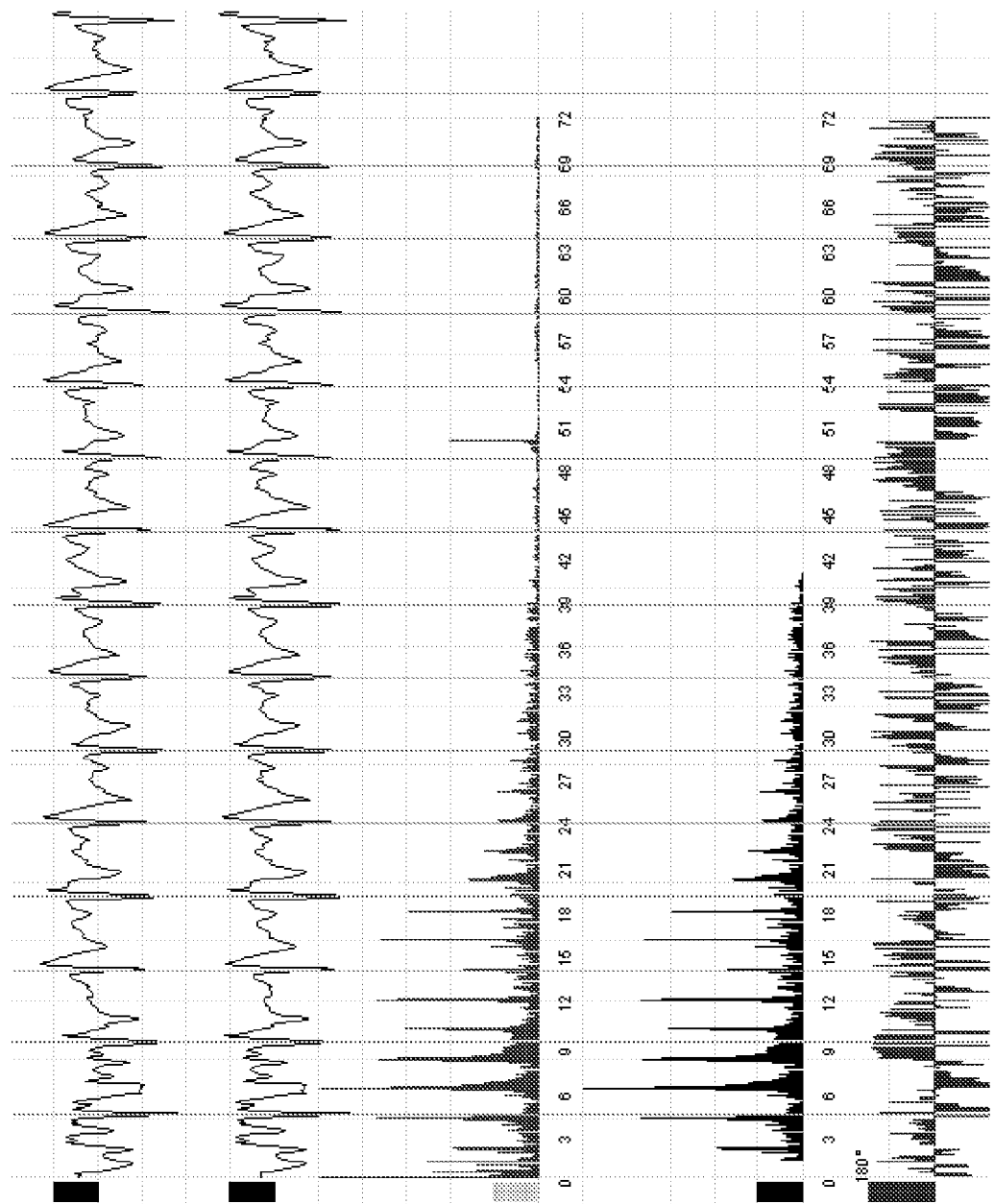
Figure 14D:
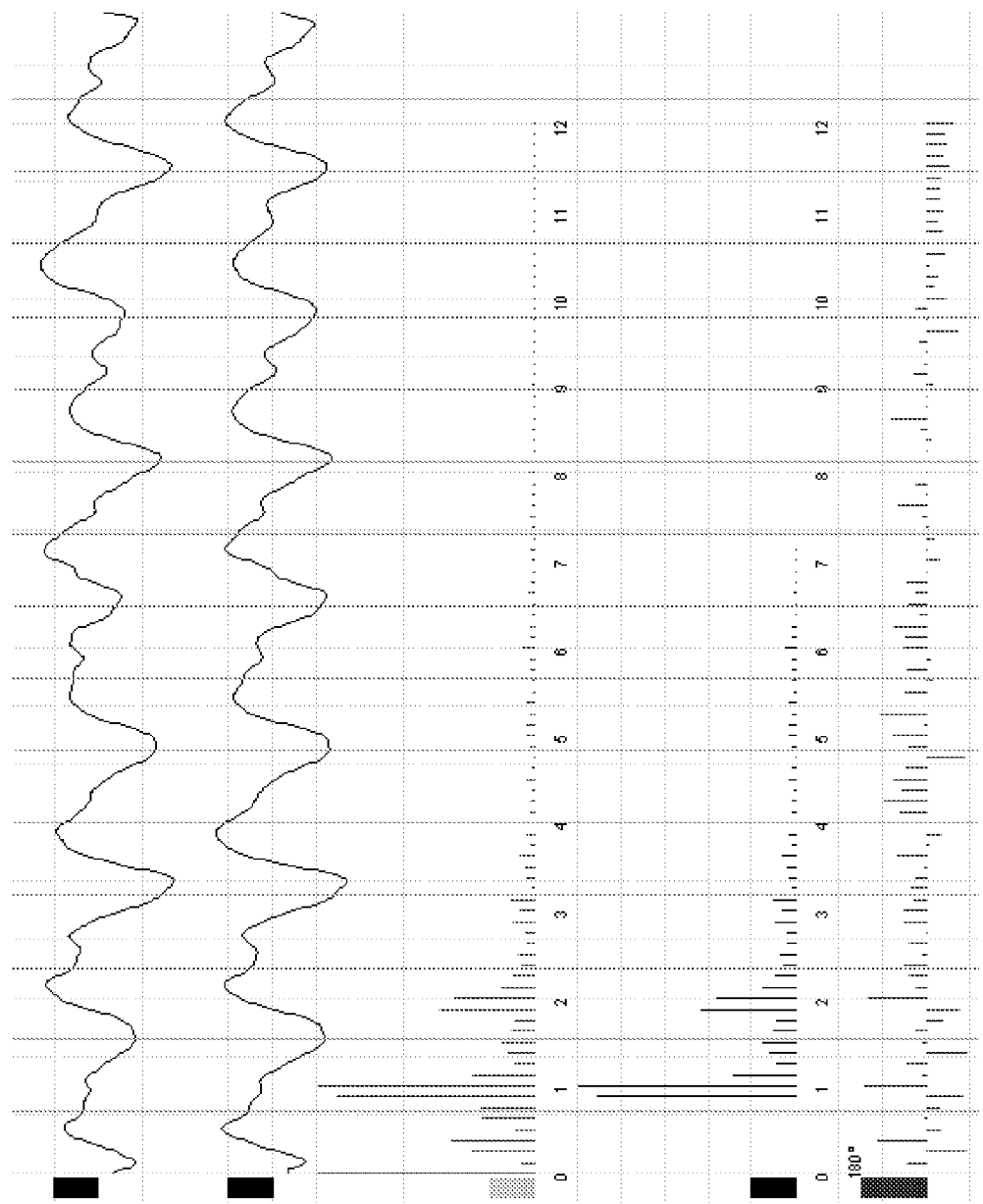
Figure 14E:
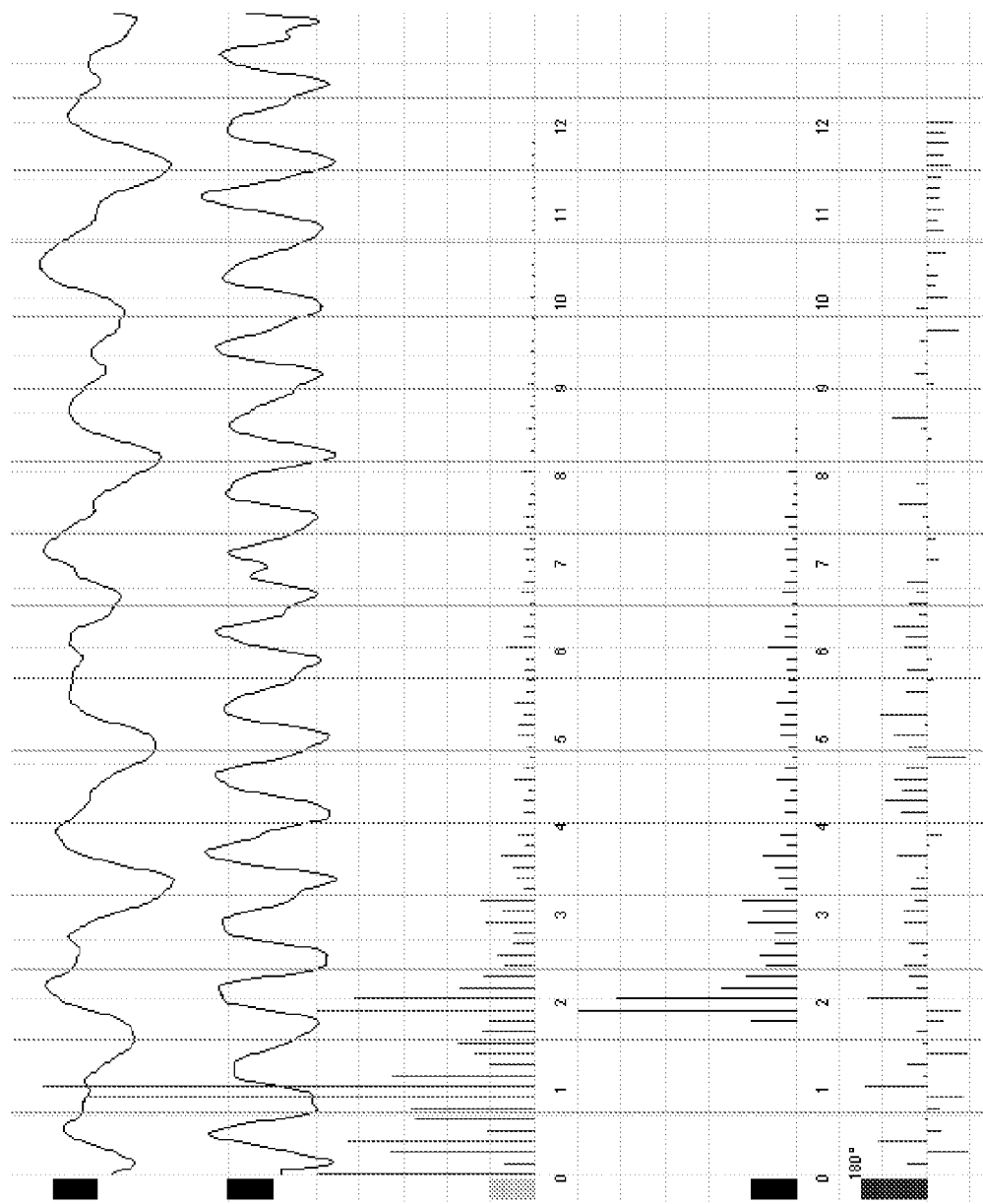
Figure 15A:
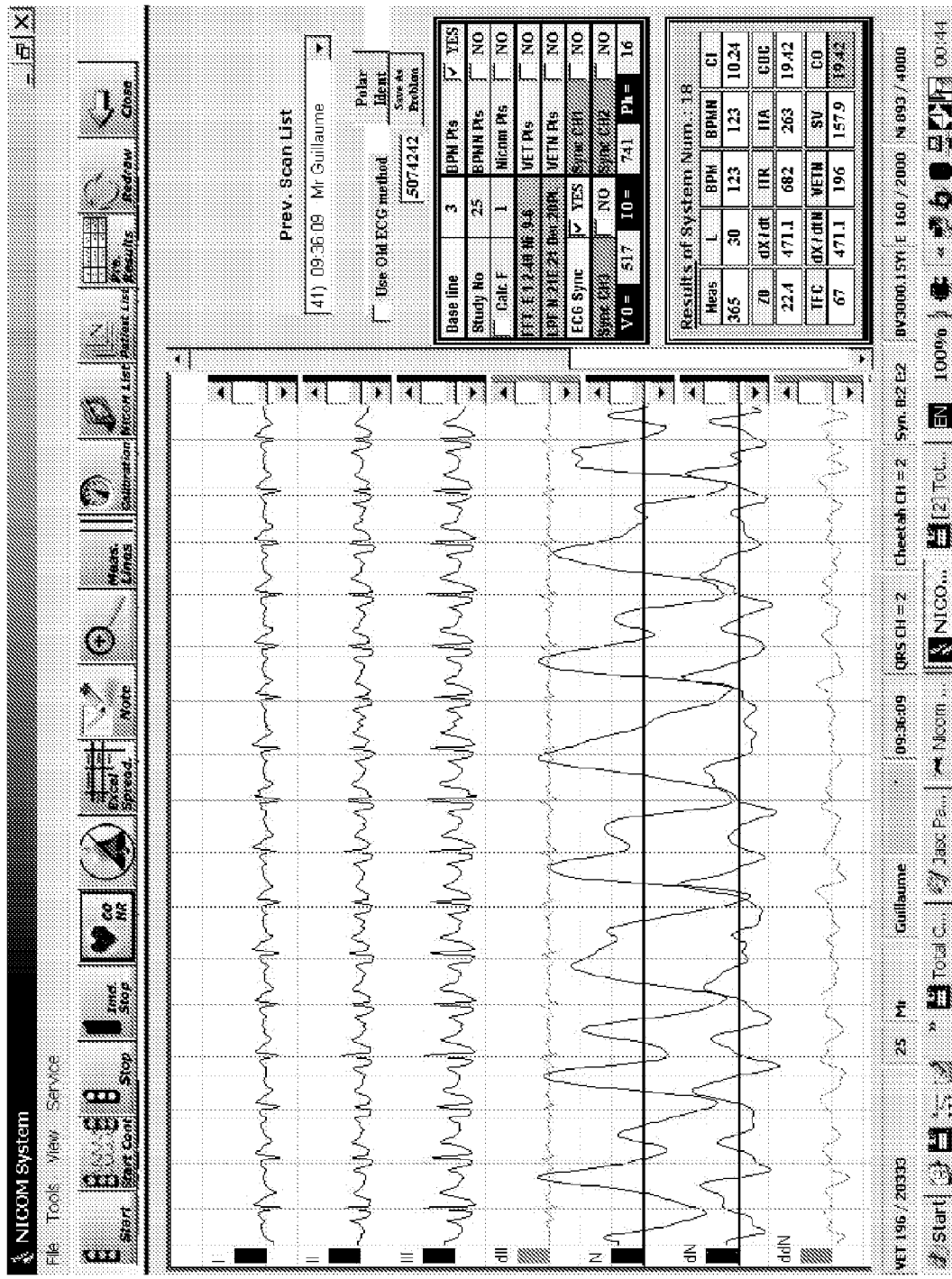
Figure 15B:
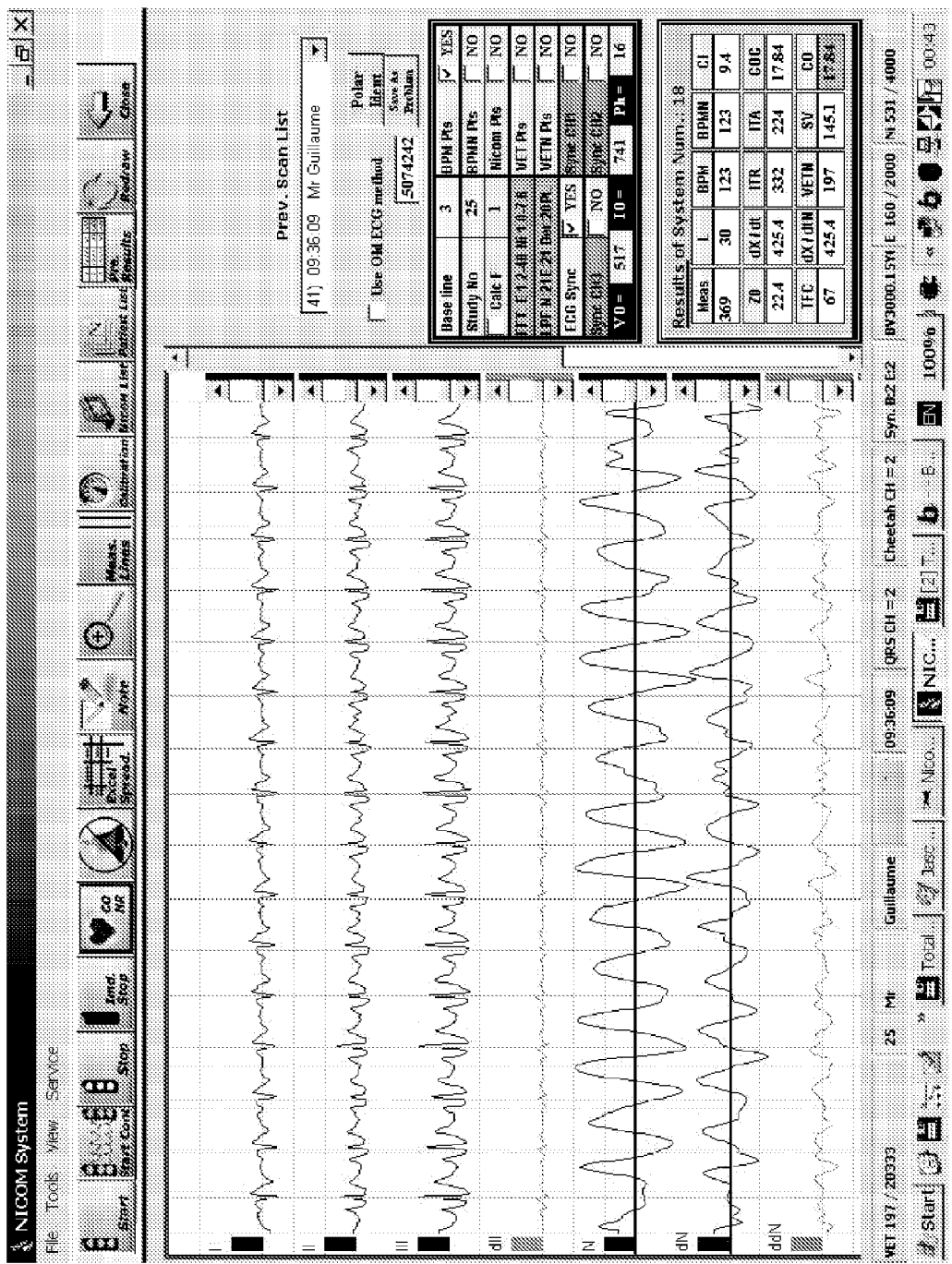
Figure 15C:
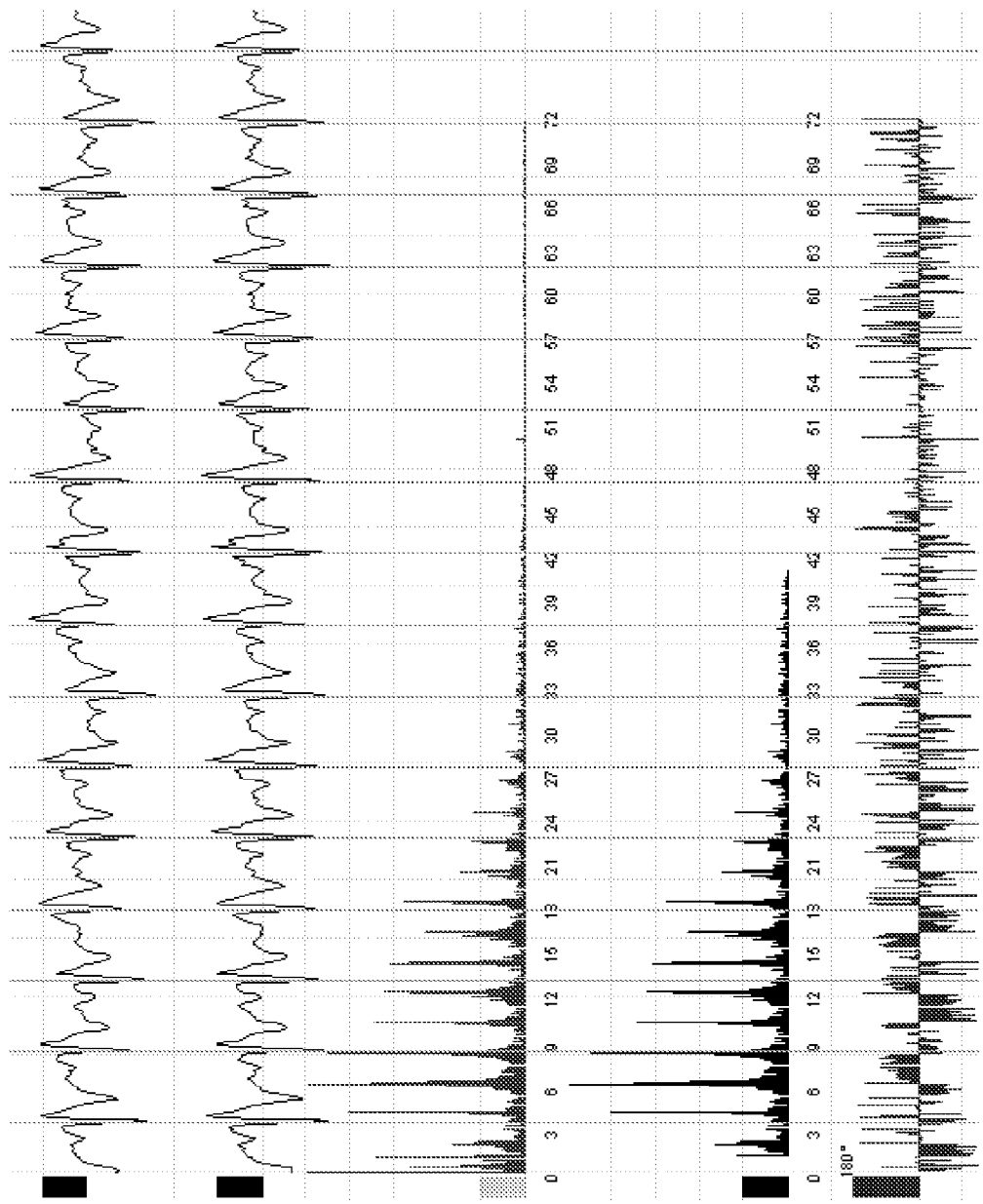
Figure 15D:
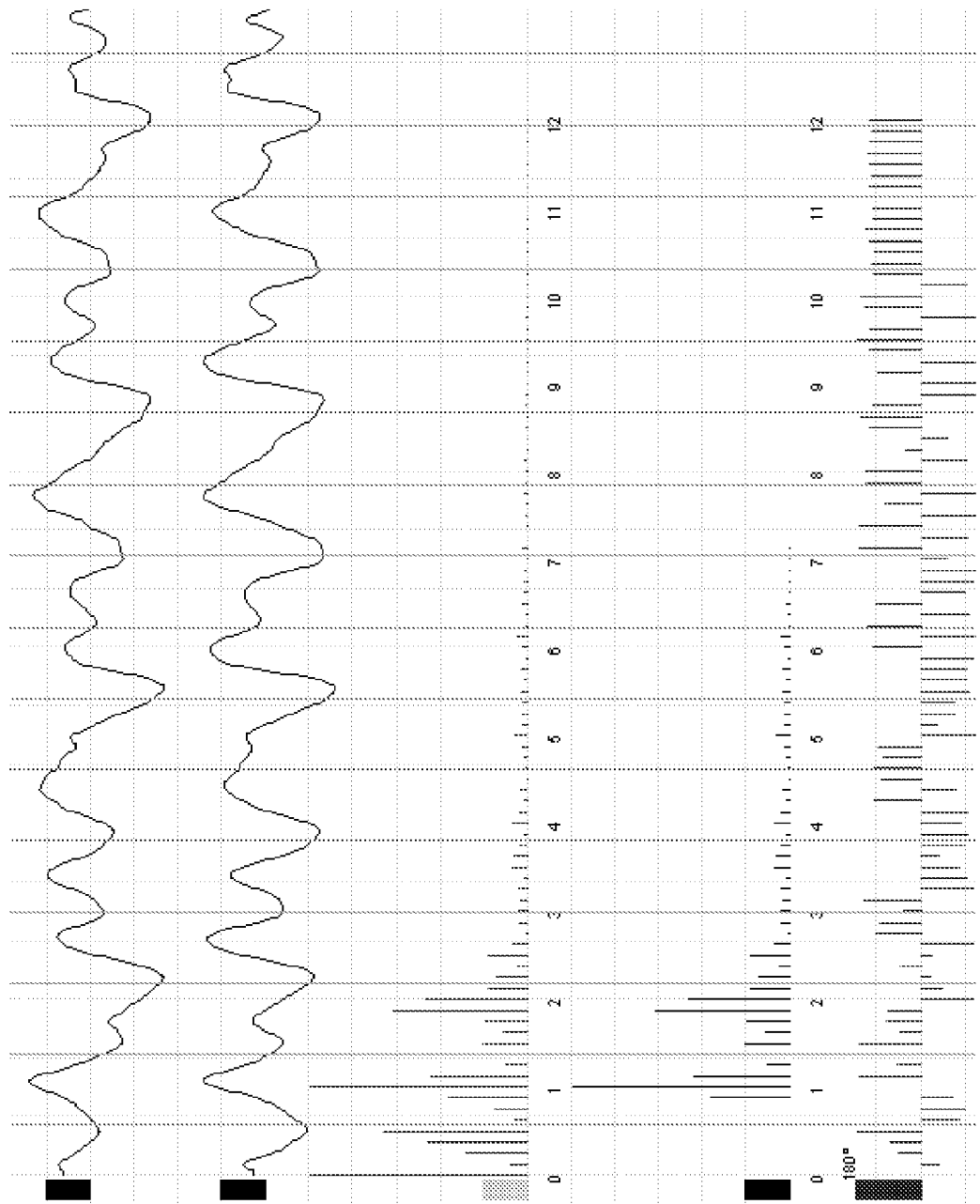
Figure 15E:
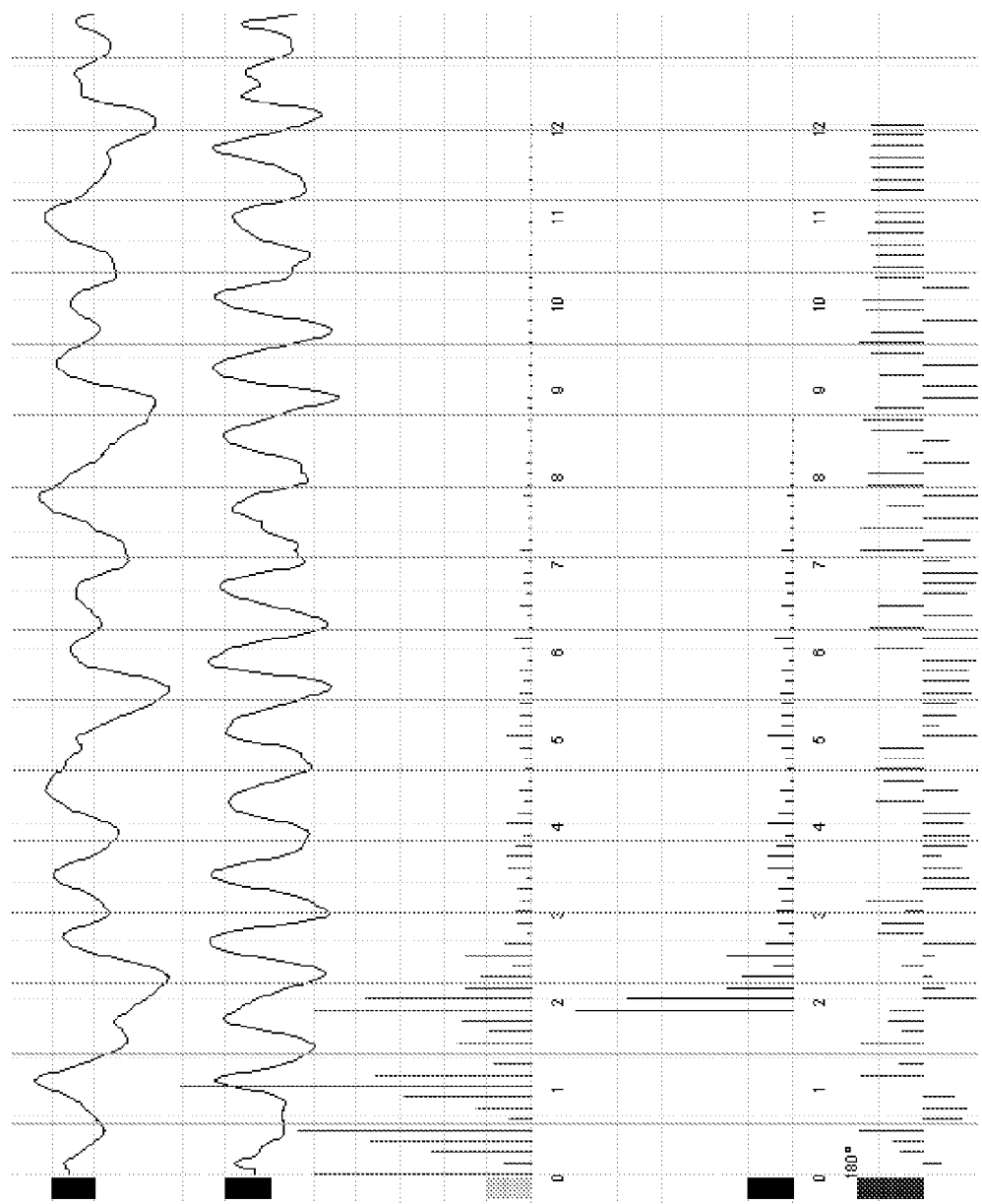

In FIG. 10c, the abscissae are scaled to 300 ms per division in the time domain representations, and 3 Hz per division in all frequency domain representations. In FIGS. 10d-e, the abscissae are scaled to 300 ms per division in the time domain representations, and 0.5 Hz per division in the frequency domain representations.

FIGS. 11a-e show snapshots of the display of the prototype system obtained during another trial in which the electrodes of the system were connected to subject No. 1. In this trial, the subject was also stable (heart rate of 114 bpm). The graphical representations in FIGS. 11a-e correspond to the same observables as FIGS. 10a-e.

The lower and upper frequency bounds of the fixed filters were the same as in the trial above. The lower and upper frequency bounds of the dynamically variable filter for the hemodynamic reactance signal were 1.7 Hz and 7.4 Hz, respectively.

FIGS. 12a-e show snapshots of the display of the prototype system obtained during another trial in which the electrodes of the system were connected to subject No. 1. In this trial, the subject was agitated (heart rate of 140 bpm). The graphical representations in FIGS. 12a-e correspond to the same observables as FIGS. 10a-e. The lower and upper frequency bounds of the fixed filters were the same as in the trials above. The lower and upper frequency bounds of the dynamically variable filter for the hemodynamic reactance signal were 2.1 Hz and 8 Hz, respectively.

FIGS. 13a-e show snapshots of the display of the prototype system obtained during another trial in which the electrodes of the system were connected to subject No. 1. In this trial, the subject was also agitated (heart rate of 137 bpm). The graphical representations in FIGS. 13a-e correspond to the same observables as FIGS. 10a-e. The lower and upper frequency bounds of the fixed filters were the same as in the trials above. The lower and upper frequency bounds of the dynamically variable filter for the hemodynamic reactance signal were 2.1 Hz and 7.9 Hz, respectively.

FIGS. 14a-e show snapshots of the display of the prototype system obtained during a trial in which the electrodes of the system were connected to subject No. 2. In this trial, the subject was agitated (heart rate of 121 bpm). The graphical representations in FIGS. 14a-e correspond to the same observables as FIGS. 10a-e. The lower and upper frequency bounds of the fixed filters were the same as in the trials above. The lower and upper frequency bounds of the dynamically variable filter for the hemodynamic reactance signal were 1.8 Hz and 7.5 Hz, respectively.

FIGS. 15a-e show snapshots of the display of the prototype system obtained during another trial in which the electrodes of the system were connected to subject No. 2. In this trial, the subject was also agitated (heart rate of 123 bpm). The graphical representations in FIGS. 15a-e correspond to the same observables as FIGS. 10a-e. The lower and upper frequency bounds of the fixed filters were the same as in the trials above.

The lower and upper frequency bounds of the dynamically variable filter for the hemodynamic reactance signal were 1.8 Hz and 7.6 Hz, respectively.

Figure 16A:
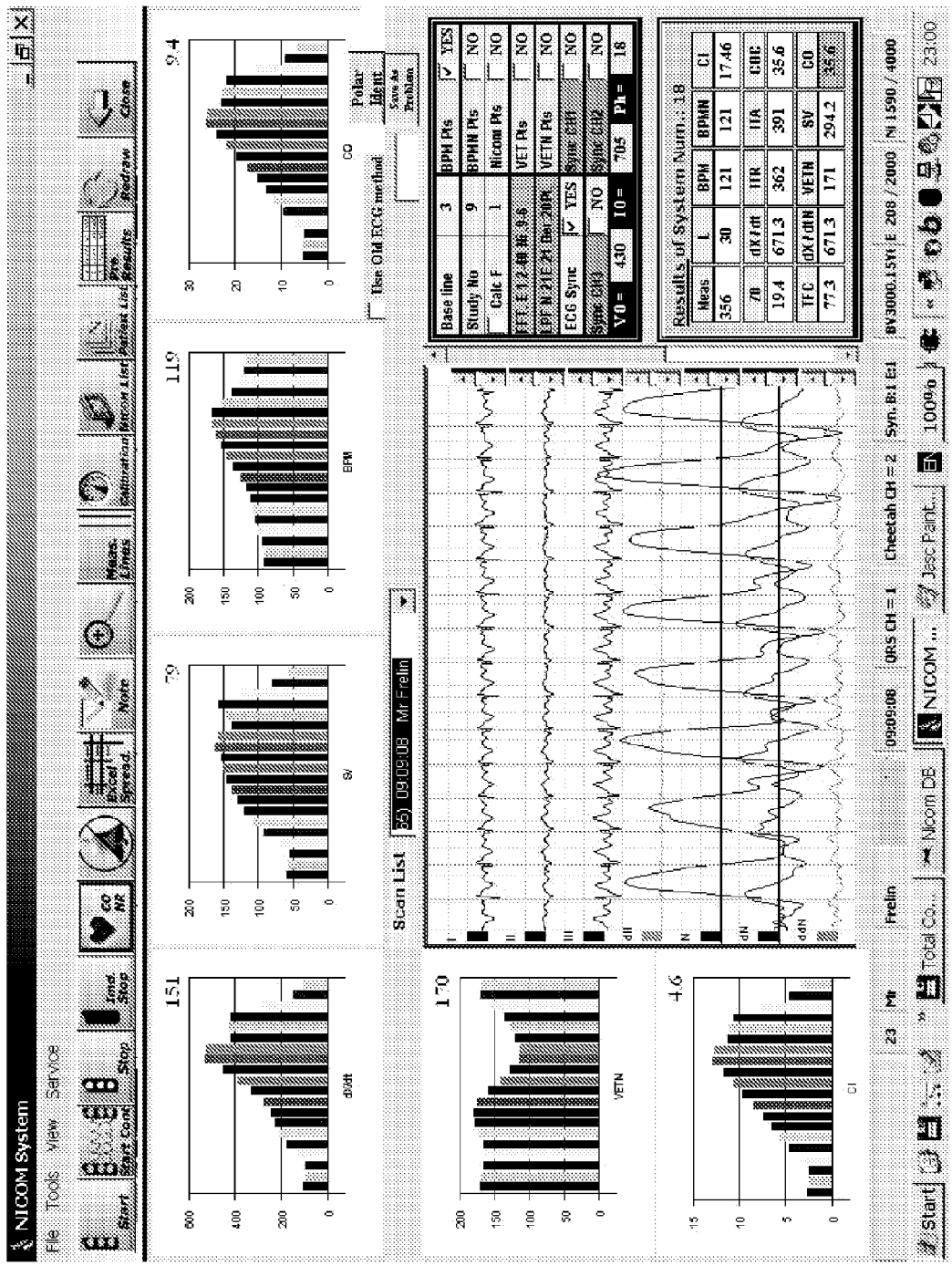
Figure 16B:
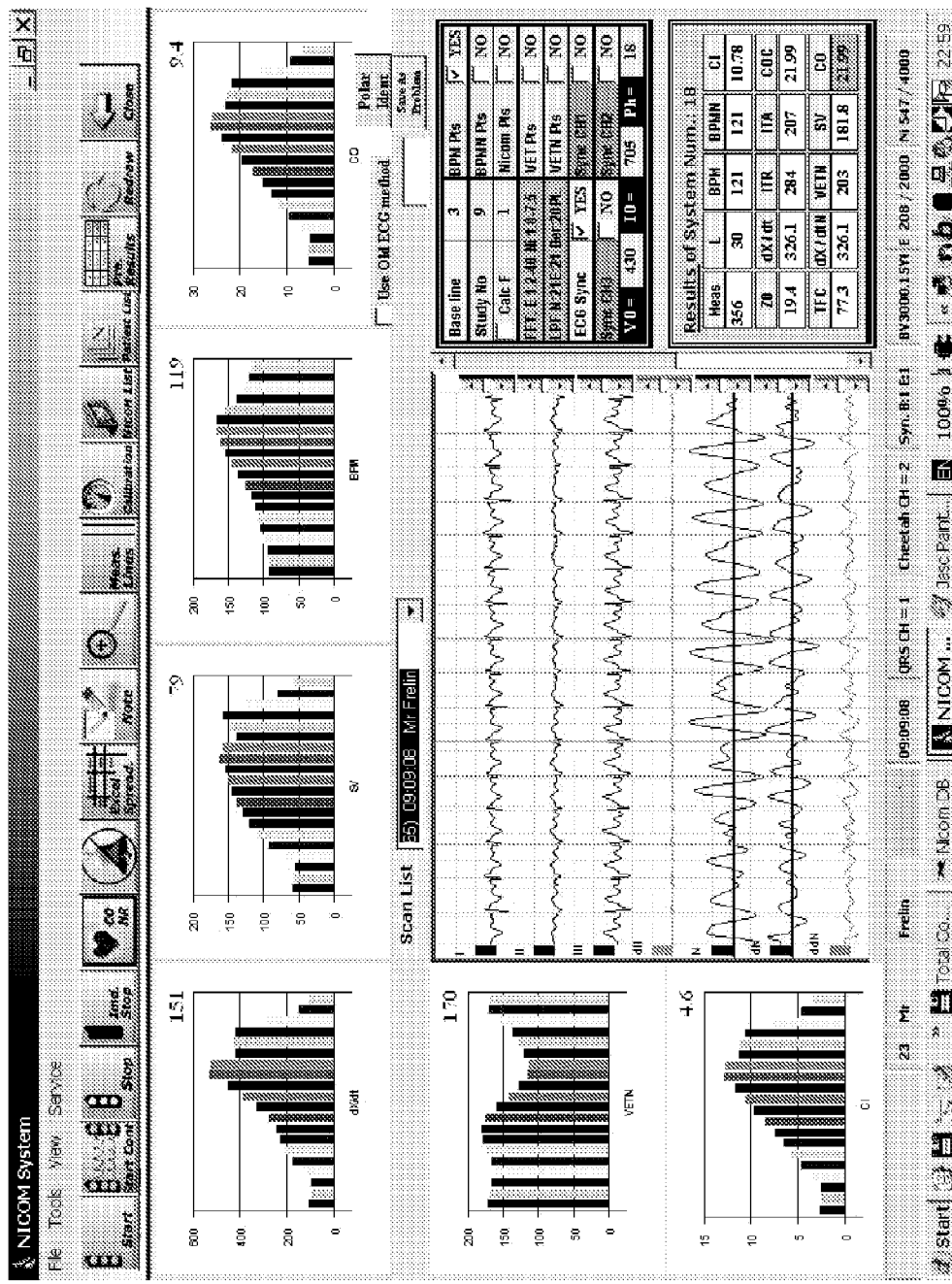
Figure 16C:
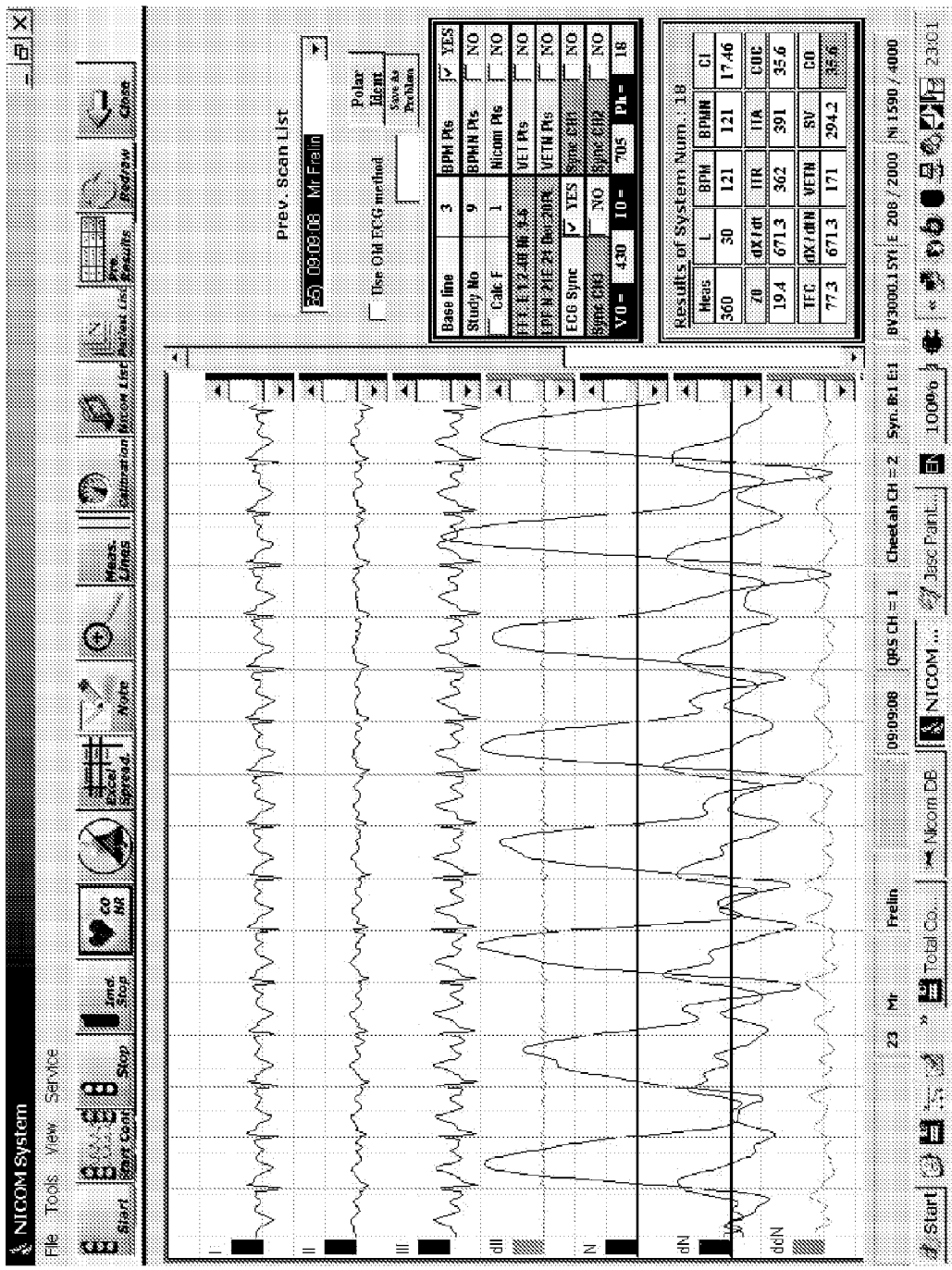
Figure 16D:
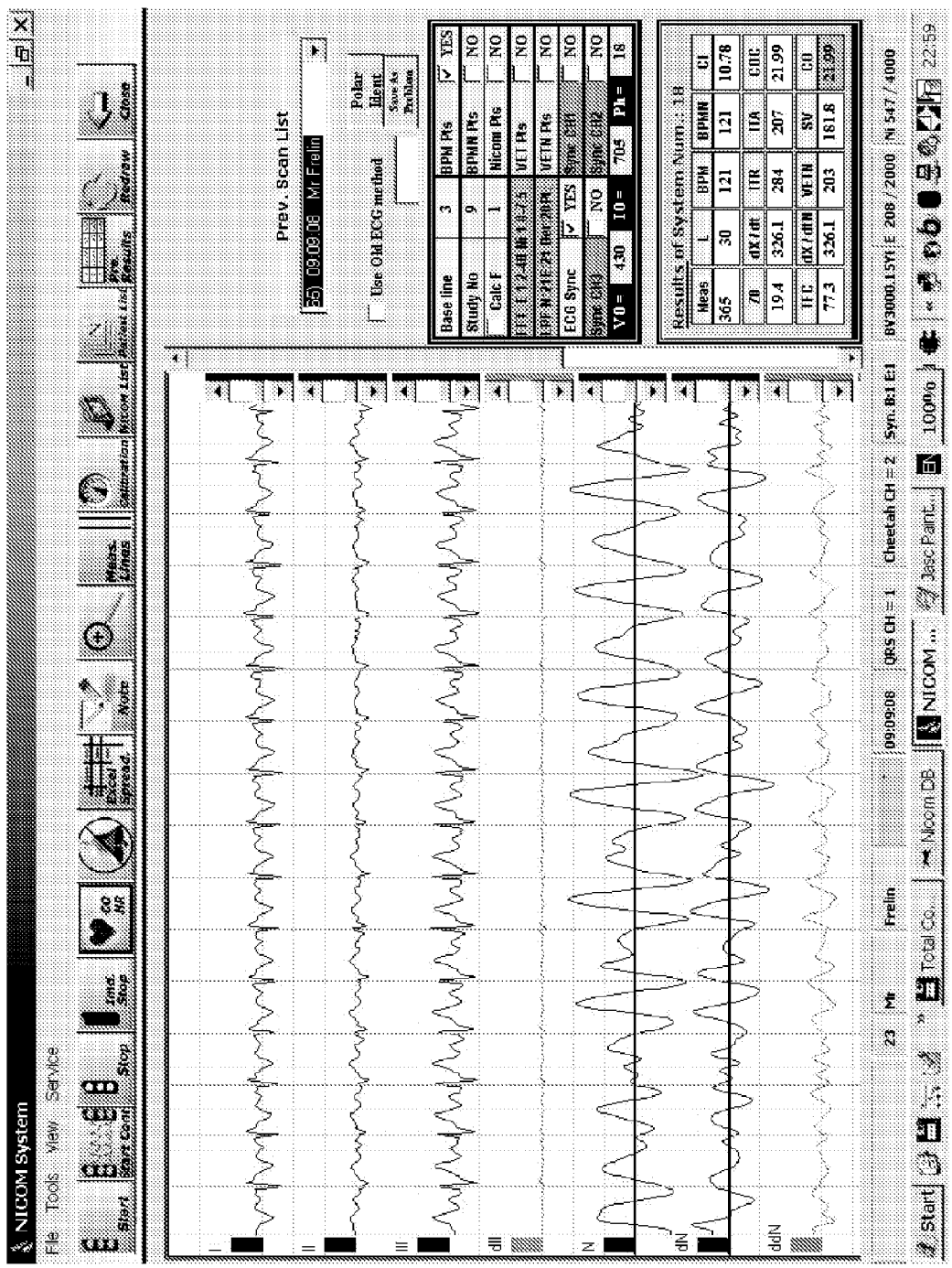
Figure 16E:
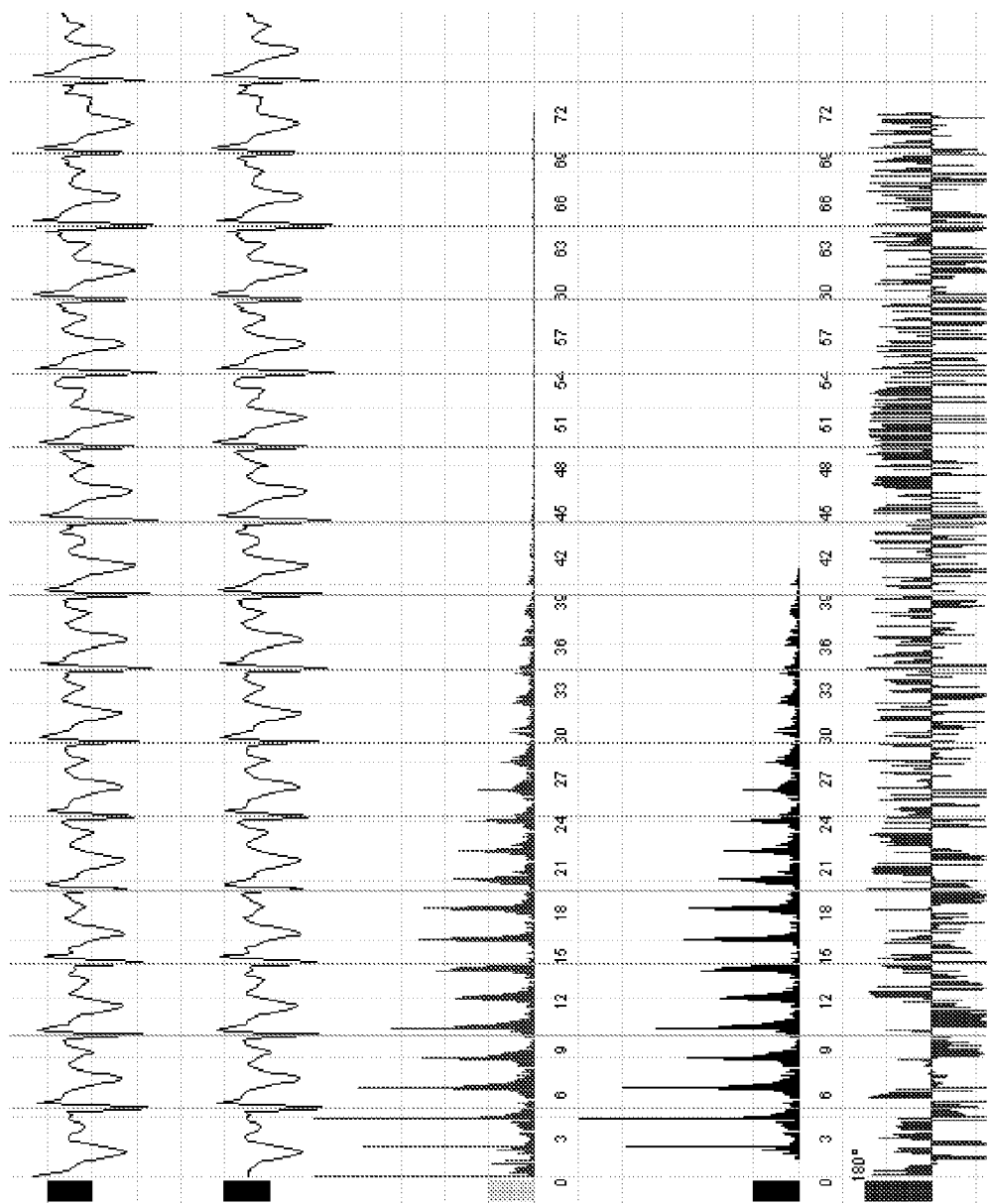
Figure 16F:
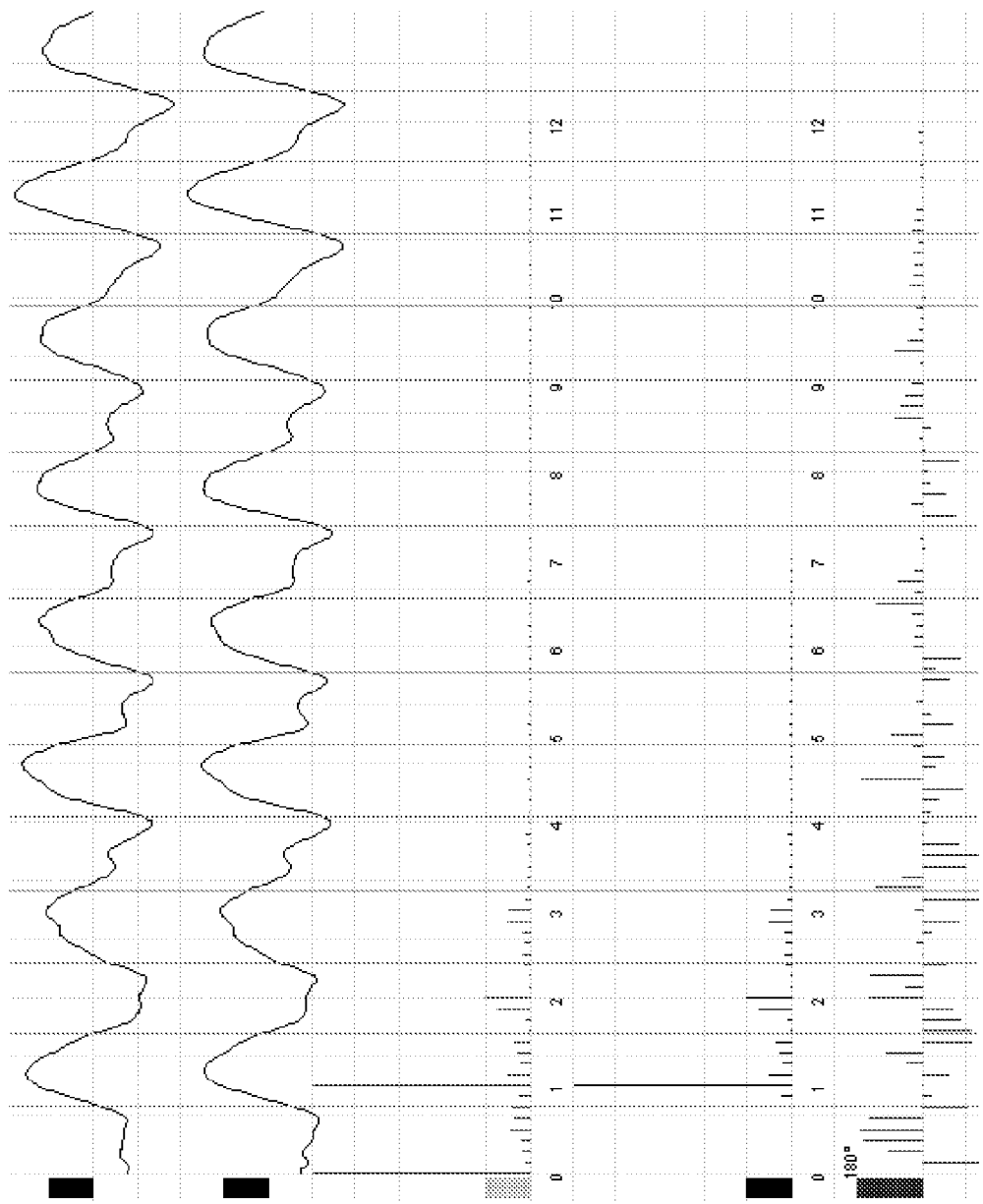
Figure 16G:
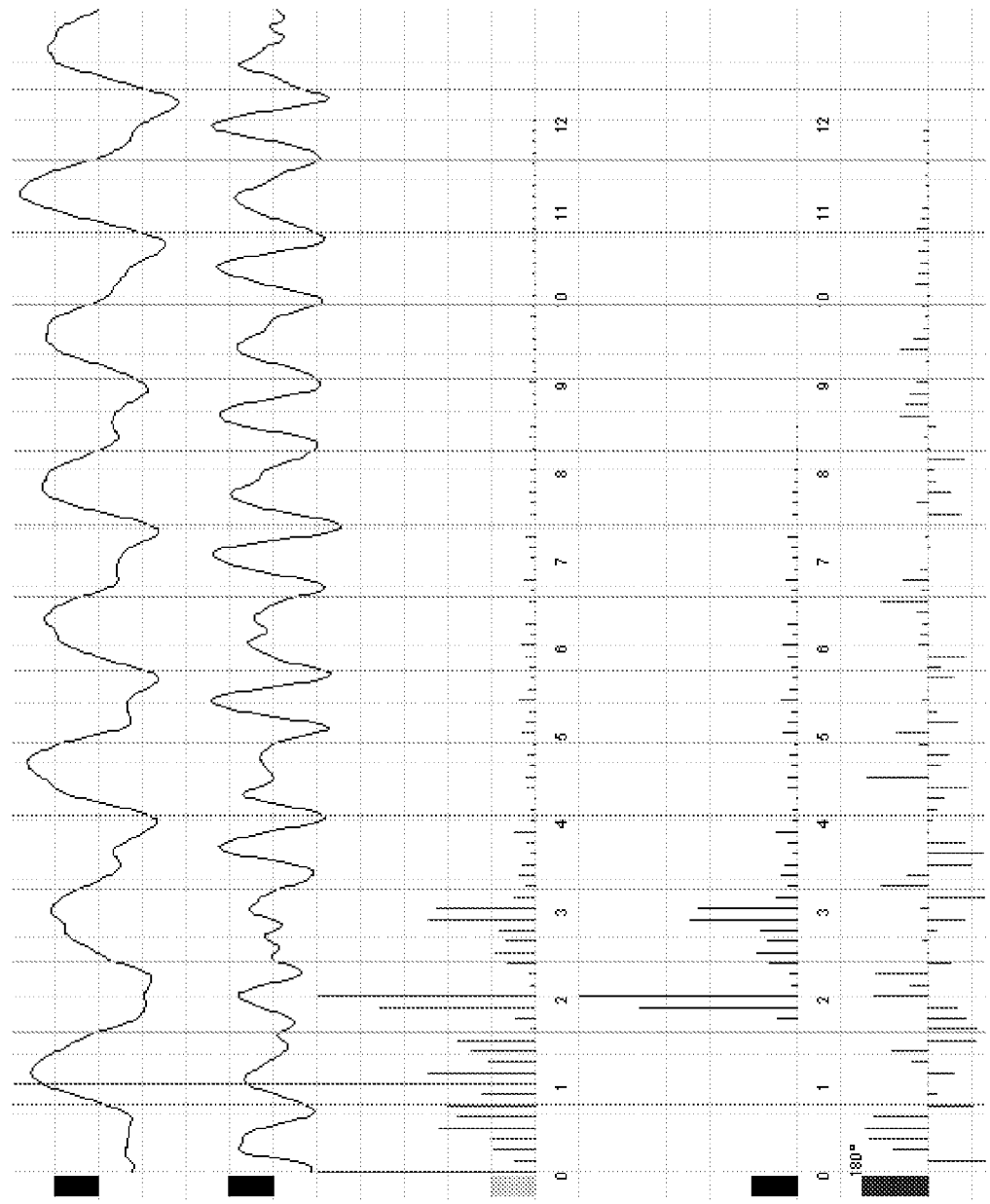

FIGS. 16a-g show snapshots of the display of the prototype system obtained during a trial in which the electrodes of the system were connected to subject No. 3. In this trial, the subject was agitated (heart rate of 121 bpm). The graphical representations in FIGS. 16a-b correspond to the same observables as FIGS. 10a-b, and the graphical representations in FIGS. 16e-g correspond to the same observables as FIGS. 10c-e. FIGS. 16c-d are respective zoom-in images of FIGS. 16a-b. The lower and upper frequency bounds of the fixed filters were the same as in the trials above. The lower and upper frequency bounds of the dynamically variable filter for the hemodynamic reactance signal were 1.8 Hz and 7.5 Hz, respectively.

Figure 17A:
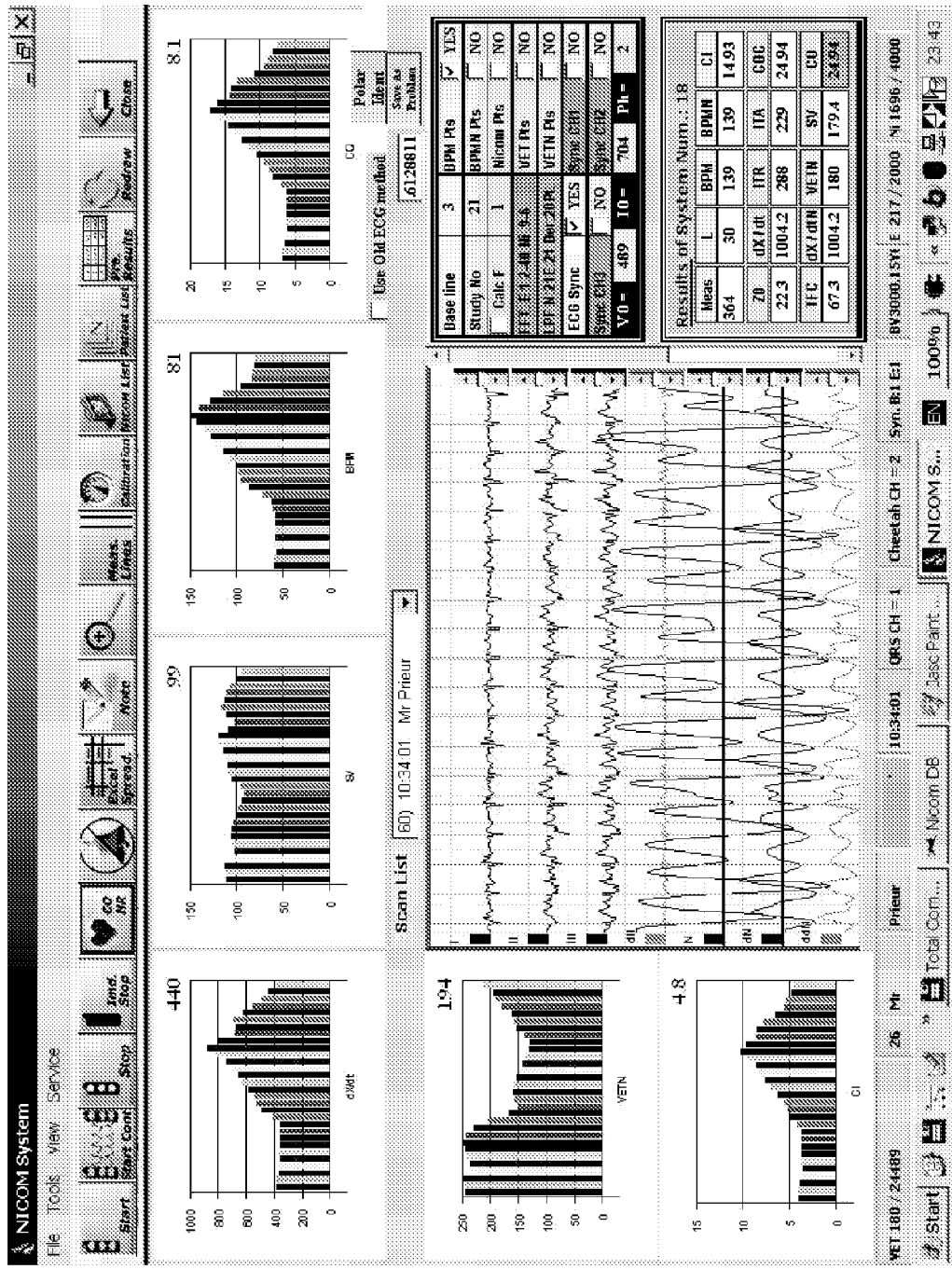
Figure 17B:
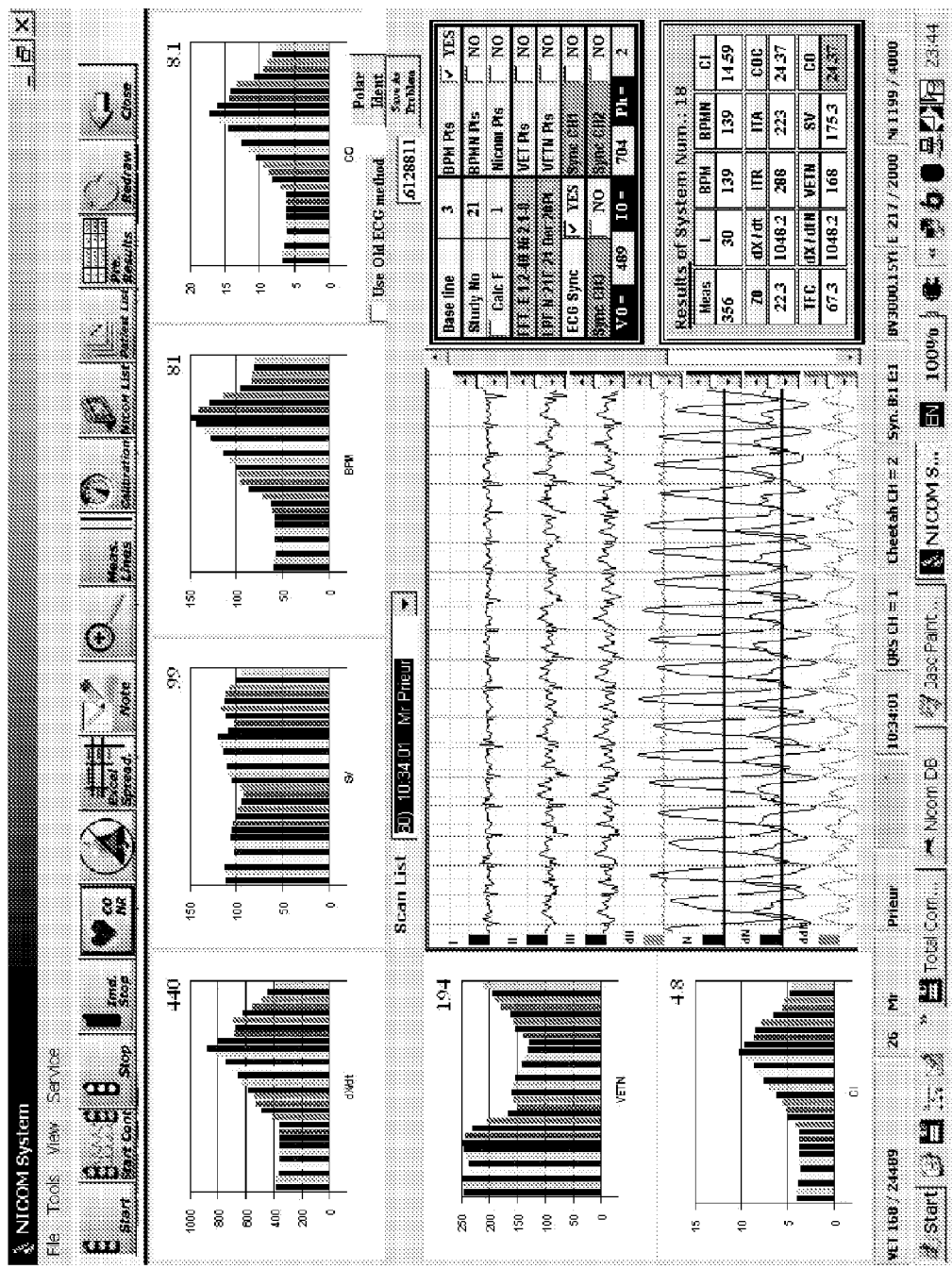
Figure 17C:
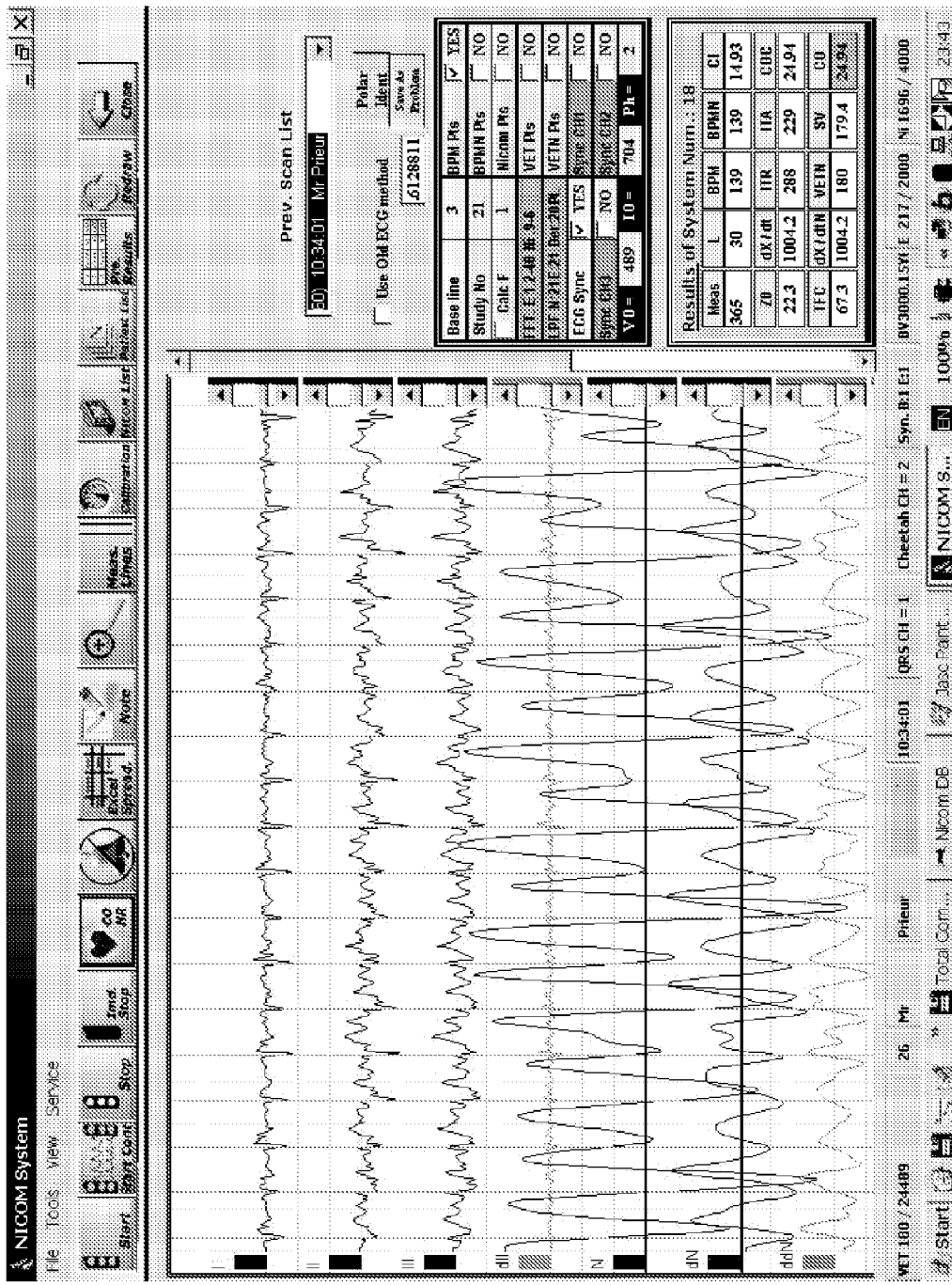
Figure 17D:
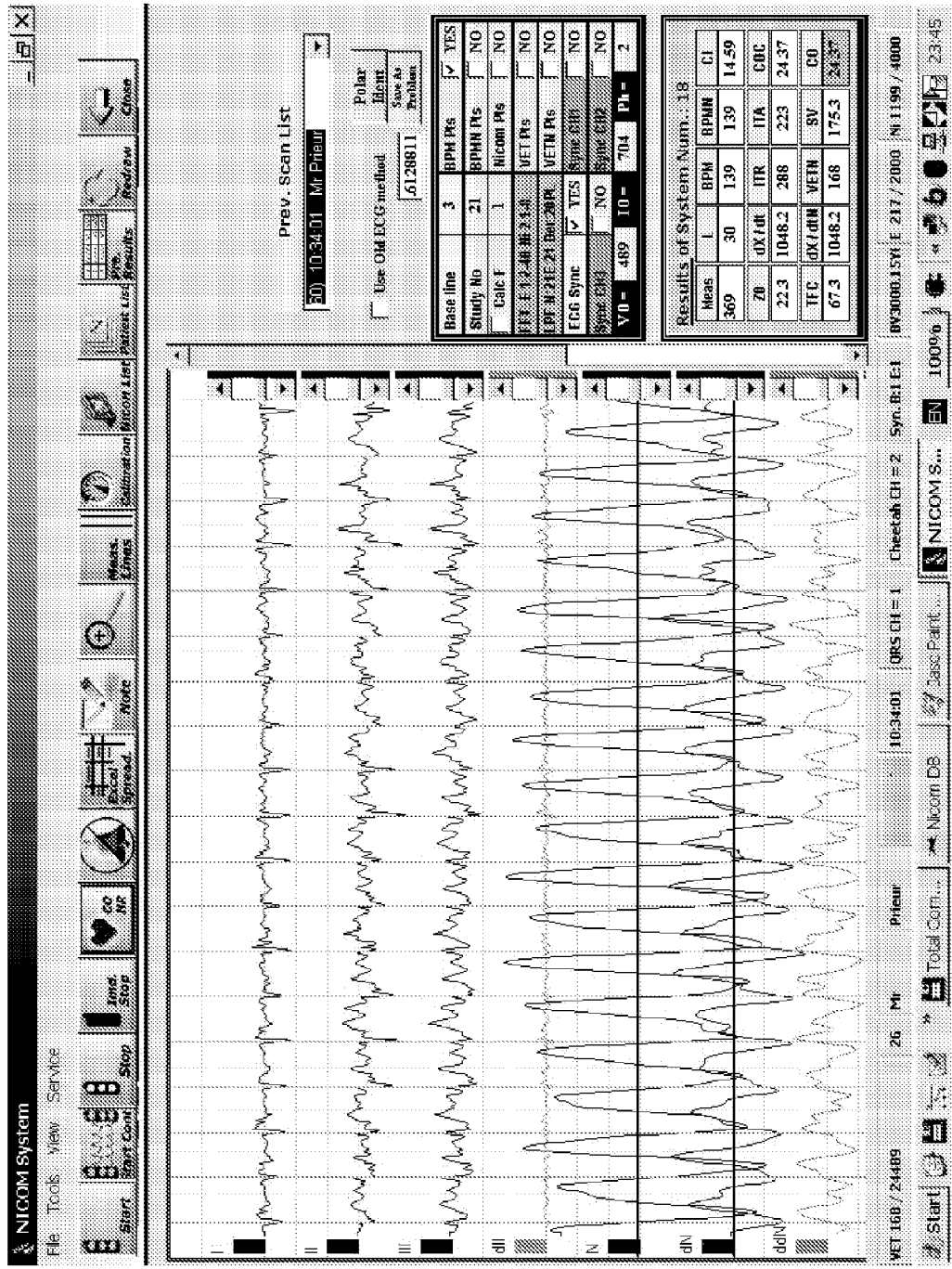
Figure 17E:
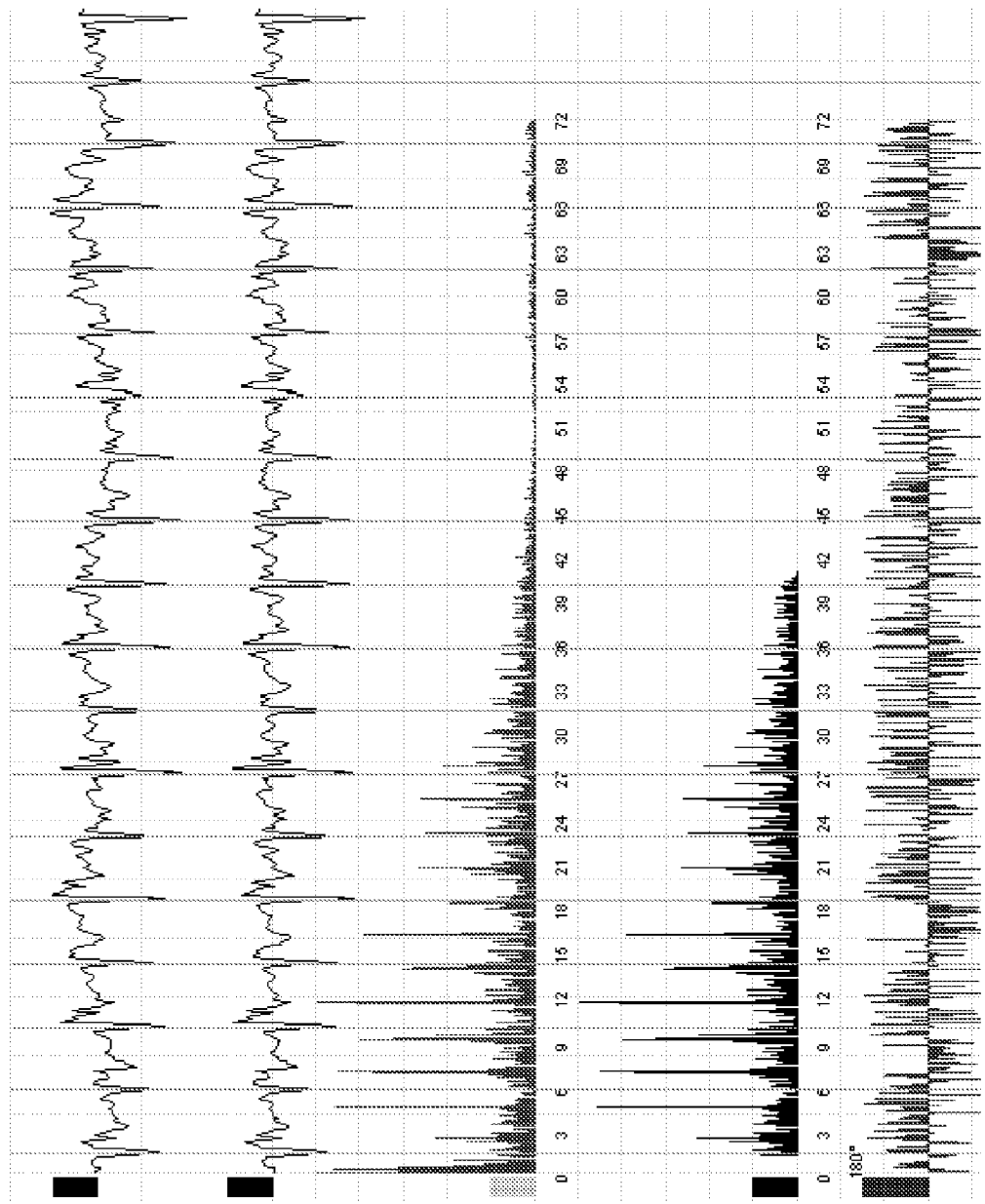
Figure 17F:
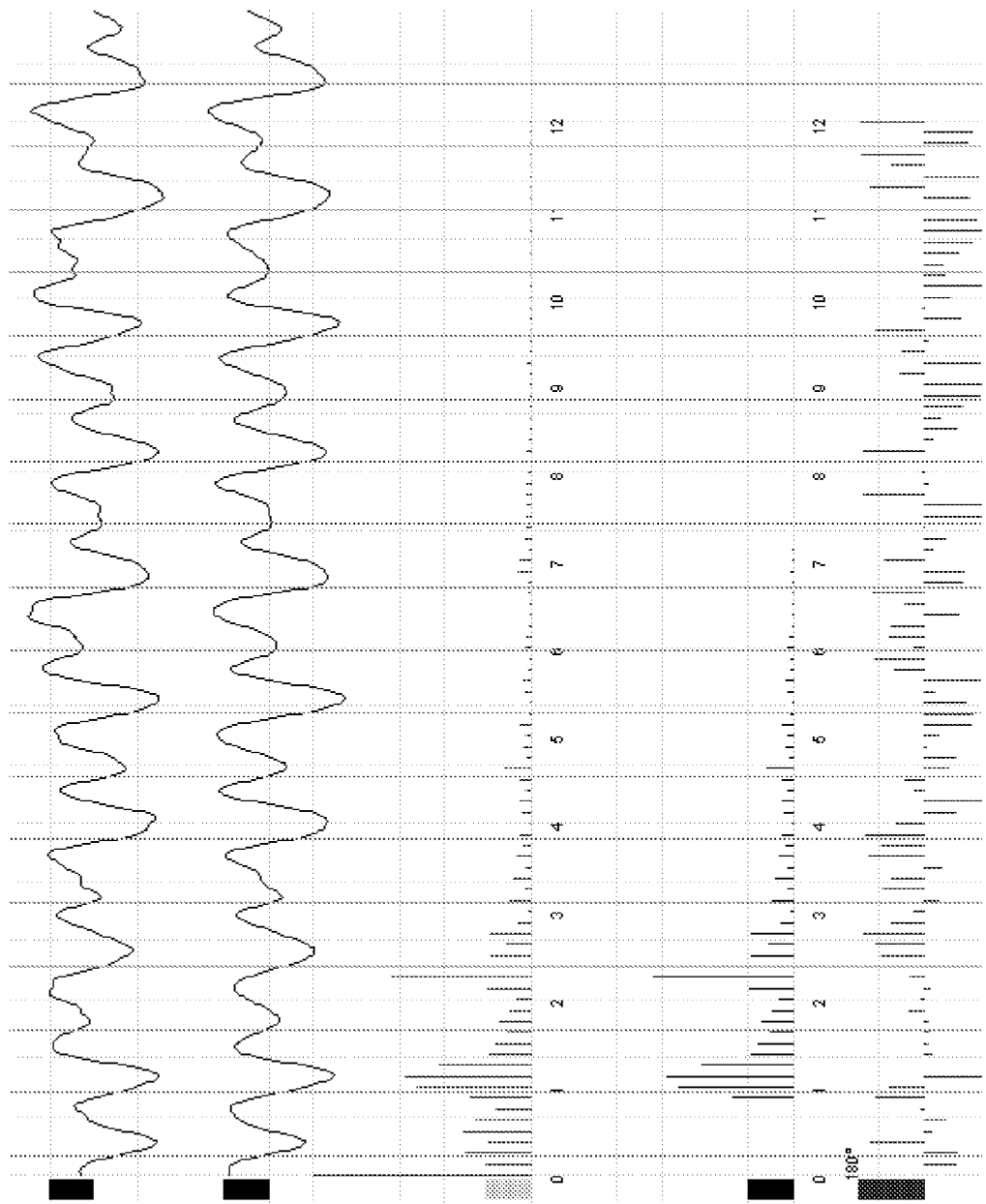
Figure 17G:
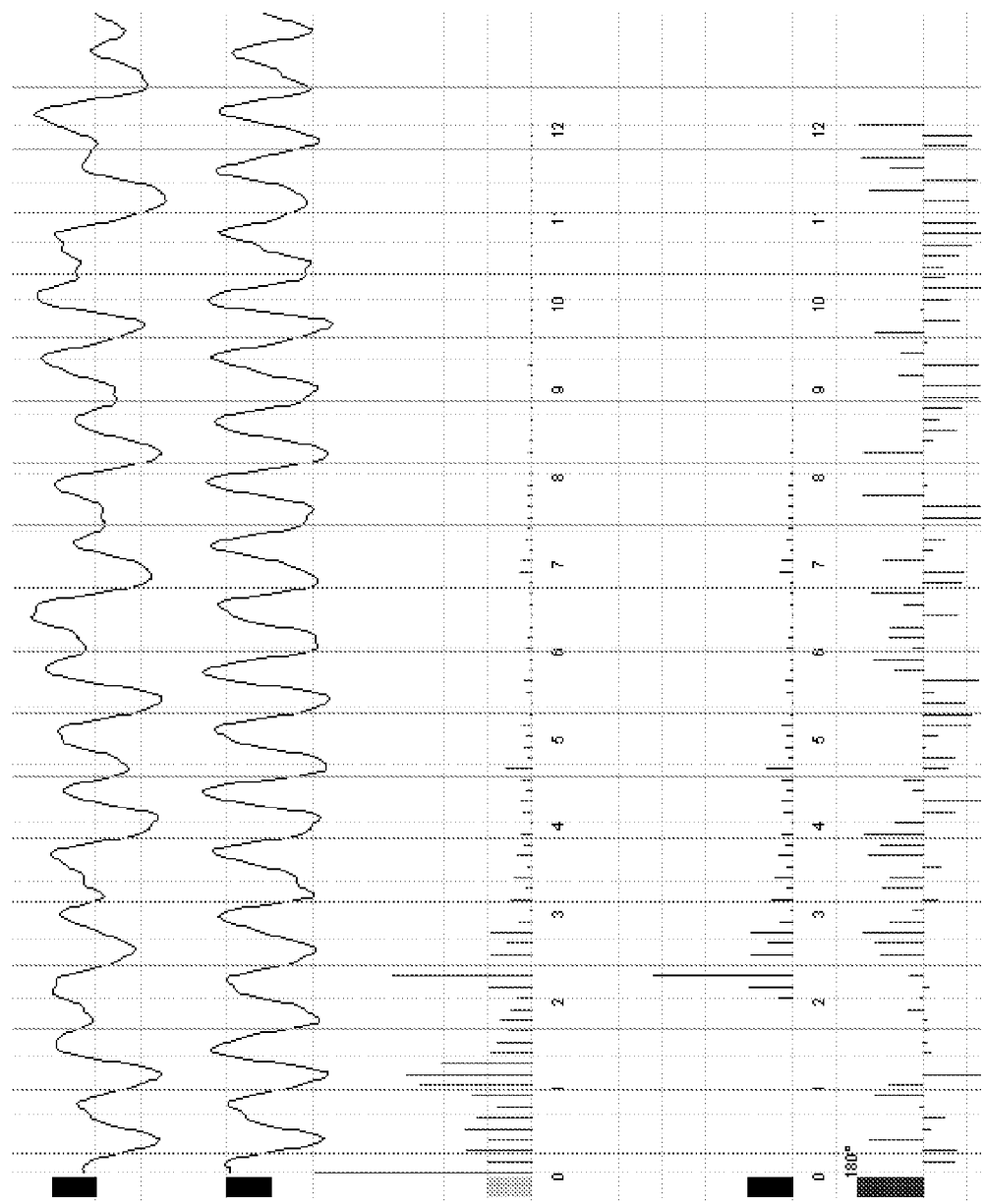

FIGS. 17a-g show snapshots of the display of the prototype system obtained during a trial in which the electrodes of the system were connected to subject No. 4. In this trial, the subject was agitated (heart rate of 139 bpm). The graphical representations in FIGS. 17a-g correspond to the same observables as FIGS. 16a-g. FIGS. 17c-d are respective zoom-in images of FIGS. 17-b. The lower and upper frequency bounds of the fixed filters were the same as in the trials above. The lower and upper frequency bounds of the dynamically variable filter for the hemodynamic reactance signal were 2.1 Hz and 8 Hz, respectively.

As shown in FIGS. 10a-17g, the dynamically varying filter significantly improves the quality of the results, particularly when the subjects are agitated (FIGS. 12a-17g). Additionally, the dynamically variable filtering technique of the present embodiments allows consistent calculation of CO values. For example, as demonstrated in the trials with Subject No. 3 (see FIGS. 16a-e), the two filtering techniques resulted in different CO values: 35.6 L/min for the fixed filtering technique and 21.99 L/min for dynamically variable filtering technique. Similar improvements were observed in other subjects.

Figures 18A, 18B:
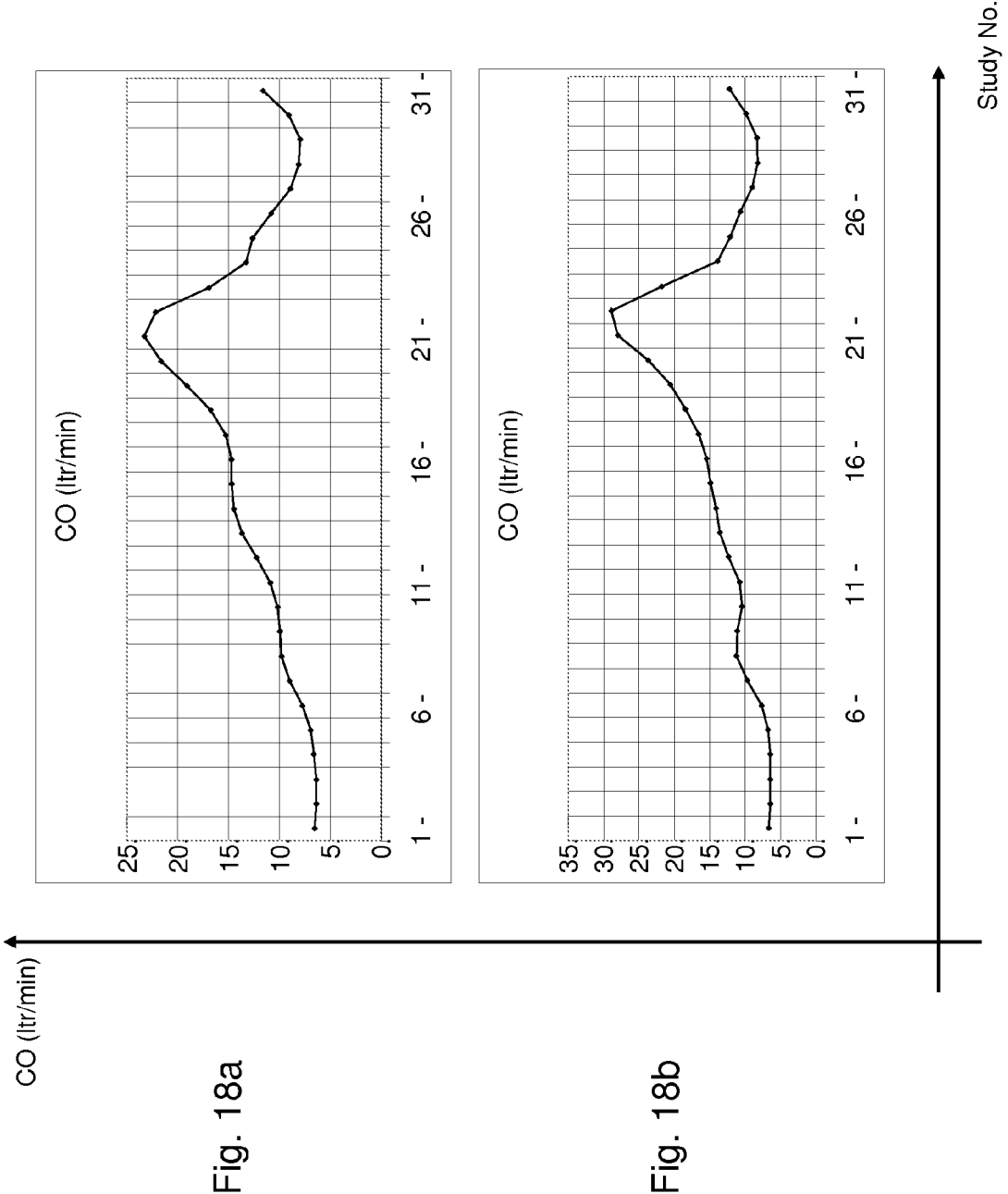
Figures 19A, 19B:
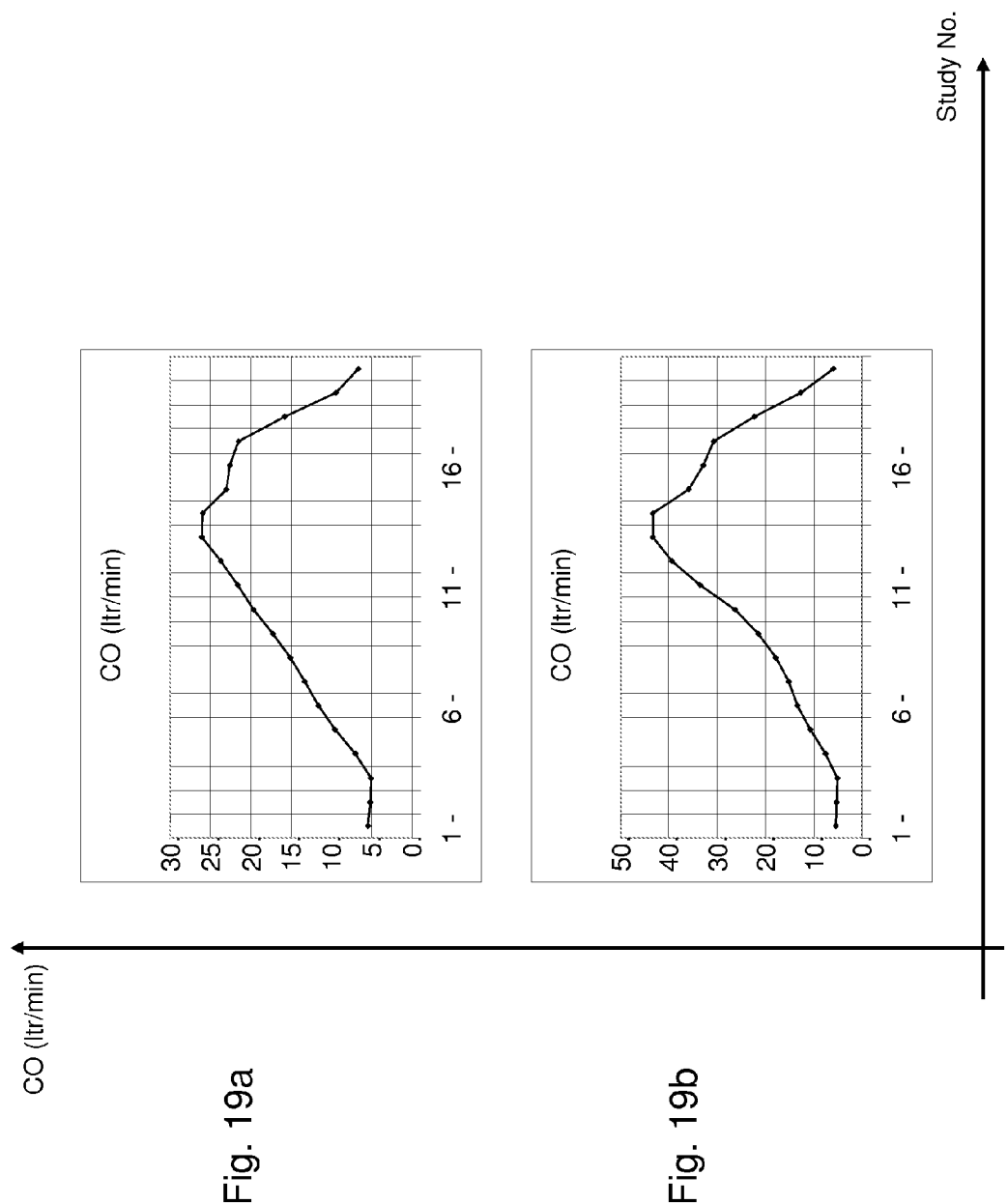

Plots of cardiac output as calculated from signals filtered using the two filtering techniques are shown in FIGS. 18a-b, 19a-b and 20a-b for subjects Nos. 2, 3 and 4, respectively. FIGS. 18a, 19a and 20a show results obtained using the dynamically variable filter of the present embodiments and FIGS. 18b, 19b and 20b show results obtained using fixed filter. As demonstrated, the CO values obtained using the dynamically variable filter of the present embodiments are more accurate.

Table 1 below summarizes the cardiac output results obtained for the above trials.

TABLE 1

| | | | filter | | |
|---|---|---|---|---|---|
| Trial No. | Subject | Heart Rate [bpm] | type | frequency band [Hz] | CO [L/min] |
| 1 | 1 | 95 | fixed | 0.6-9.0 | 14.62 |
| | | | variable | 1.4-6.9 | 14.68 |
| 2 | 1 | 114 | fixed | 0.6-9.0 | 18.81 |
| | | | variable | 1.7-7.4 | 19.77 |
| 3 | 1 | 140 | fixed | 0.6-9.0 | 18.55 |
| | | | variable | 2.1-8 | 18.41 |
| 4 | 1 | 137 | fixed | 0.6-9.0 | 15.82 |
| | | | variable | 2.1-7.9 | 17.05 |
| 5 | 2 | 121 | fixed | 0.6-9.0 | 13.92 |
| | | | variable | 1.8-7.5 | 18.47 |
| 6 | 2 | 123 | fixed | 0.6-9.0 | 19.42 |
| | | | variable | 1.8-7.6 | 17.84 |
| 7 | 3 | 121 | fixed | 0.6-9.0 | 35.60 |
| | | | variable | 1.8-7.5 | 21.99 |

TABLE 1-continued

| | | | filter | | |
|---|---|---|---|---|---|
| Trial No. | Subject | Heart Rate [bpm] | type | frequency band [Hz] | CO [L/min] |
| 8 | 4 | 139 | fixed | 0.6-9.0 | 24.94 |
| | | | variable | 2.1-8.0 | 24.37 |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of analyzing an input radiofrequency signal sensed from an organ of a subject, comprising:
  processing said input radiofrequency signal to provide a processed input signal, wherein said processing comprises determining a phase shift of said input signal relative to an output radiofrequency signal transmitted to the organ;
  filtering said processed signal using a dynamically variable band pass filter, thereby providing a filtered signal; and
  using said filtered signal and said phase shift for calculating at least one of: a stroke volume, a cardiac output, a brain intra luminal blood volume and blood flow;
  wherein the method further comprising executing an iterative process to dynamically update an upper frequency bound of said filter in response to a change in a physiological condition of the subject.

2. The method of claim 1, wherein said possessing comprises filtering said input radiofrequency signal using an analog filter.

3. The method of claim 1, wherein said blood flow comprises at least one of: an external carotid blood flow rate, an internal carotid blood flow rate, an ulnar blood flow rate, a radial blood flow rate, a brachial blood flow rate, a common iliac blood flow rate, an external iliac blood flow rate, a posterior tibial blood flow rate, an anterior tibial blood flow rate, a peroneal blood flow rate, a lateral plantar blood flow rate, a medial plantar blood flow rate and a deep plantar blood flow rate.

4. The method of claim 1, further comprising transmitting said output radiofrequency signal to the organ and sensing said input radiofrequency signal from the organ.

5. The method of claim 1, further comprising reducing or eliminating amplitude modulation of said input radiofrequency signal, so as to provide a signal of substantially constant envelope.

6. The method of claim 5, wherein said reducing or eliminating said amplitude modulation comprises maintaining a phase modulation of said input radiofrequency signal.

7. The method of claim 1, wherein said physiological condition is a heart rate of the subject.

8. The method of claim 7, wherein at least one of a lower frequency bound and an upper frequency bound characterizing said filter is a linear function of said heart rate.

9. The method of claim 8, wherein said lower frequency bound is about 0.9*(HR/60) Hz at all times, wherein said HR is said heart rate in units of beats per minute.

10. The method of claim 7, wherein said heart rate is determined from an ECG signal received from said subject.

11. The method of claim 7, wherein an initial value of said upper frequency bound in said iterative process is a linear function of said heart rate.

12. The method of claim 11, wherein an initial value of said upper frequency bound in said iterative process is about 6+1.5*[(HR/60)−1] Hz, wherein said HR is said heart rate in units of beats per minute.

13. The method of claim 1, wherein said iterative process is based on a comparison between a value of a physiological parameter as extracted from said filtered input signal and a value of said physiological parameter as extracted from a reference signal.

14. The method of claim 13, wherein said reference signal comprises an ECG signal.

15. The method of claim 13, wherein each iteration of said iterative process comprises:
if said comparison meets a predetermined criterion, then updating said upper frequency bound by calculating an average between a low threshold and a high threshold;
said thresholds being predetermined or set in a previous iteration of said iterative process.

16. The method of claim 13, wherein said physiological parameter is a ventricular ejection time (VET).

17. The method of claim 16, wherein said VET is averaged over a plurality of heart beats.

18. The method of claim 16, wherein said VET is extracted from an average heart beat morphology of the subject.

19. The method of claim 1, wherein said input radiofrequency signal is indicative of impedance of the organ.

20. The method of claim 1, wherein said input radiofrequency signal is indicative of hemodynamic reactance of the organ.

21. Apparatus for analyzing an input radiofrequency signal sensed from an organ of a subject, comprising:
an input unit for receiving the input radiofrequency signal;
a signal processing circuit configured for processing said input radiofrequency signal to provide a processed input signal, said processing unit comprising a phase shift determinator configured for determining a phase shift of said input signal relative to an output radiofrequency signal transmitted to the organ;
a filtering unit configured for filtering said processed signal using a dynamically variable band pass filter, to thereby provide a filtered signal; and
a data processor having a circuit configured for applying an iterative process to dynamically update an upper frequency bound of said filter in response to a change in a physiological condition of the subject, and for calculating at least one quantity based on said phase shift, wherein said at least one quantity is selected from the group consisting of a stroke volume, a cardiac output, a brain intra luminal blood volume and blood flow.

22. The apparatus of claim 21, wherein said physiological condition is a heart rate of the subject.

23. The apparatus of claim 22, wherein an initial value of said upper frequency bound in said iterative process is a linear function of said heart rate.

24. The apparatus of claim 23, wherein an initial value of said upper frequency bound in said iterative process is about 6+1.5*[(HR/60)−1] Hz, wherein said HR is said heart rate in units of beats per minute.

25. The apparatus of claim 21, wherein said signal processing unit comprises an envelope elimination unit designed and configured to reduce or eliminate amplitude modulation of said filtered signal, so as to provide a signal of substantially constant envelope.

26. The apparatus of claim 25, wherein said envelope elimination unit is designed and configured to maintain a phase modulation of said signal.

27. A system for monitoring at least one electrical property of an organ of a subject, comprising:
a radiofrequency generator for generating an output radiofrequency signal;
a plurality of electrodes, designed to be connectable to the skin of the subject, said electrodes being for transmitting said output radiofrequency signal to the organ and for sensing an input radiofrequency signal from the organ; and
the apparatus according to claim 21.

* * * * *